US007989675B2

(12) United States Patent
Welsh et al.

(10) Patent No.: US 7,989,675 B2
(45) Date of Patent: Aug. 2, 2011

(54) METHOD OF IDENTIFYING COMPOUNDS USING A TRANSGENIC PIG MODEL OF CYSTIC FIBROSIS

(75) Inventors: Michael J. Welsh, Riverside, IA (US); Christopher S. Rogers, North Liberty, IA (US); Randall Prather, Rocheport, MO (US); John Engelhardt, Iowa City, IA (US); Ziying Yan, Iowa City, IA (US)

(73) Assignees: University of Iowa Research Foundation, Iowa City, IA (US); The Curators of the University of Missouri, Columbus, MO (US)

(*) Notice: Subject to any disclaimer, the term of this patent is extended or adjusted under 35 U.S.C. 154(b) by 237 days.

(21) Appl. No.: 12/074,632

(22) Filed: Mar. 5, 2008

(65) Prior Publication Data

US 2009/0235368 A1 Sep. 17, 2009

Related U.S. Application Data

(60) Provisional application No. 60/966,971, filed on Aug. 30, 2007, provisional application No. 60/908,637, filed on Mar. 28, 2007.

(51) Int. Cl.
*G01N 33/00* (2006.01)
*A01K 67/00* (2006.01)
*A01K 67/027* (2006.01)

(52) U.S. Cl. .................................. 800/3; 800/9; 800/17

(58) Field of Classification Search .................. 800/3, 9, 800/17

See application file for complete search history.

(56) References Cited

U.S. PATENT DOCUMENTS

| | | | | |
|---|---|---|---|---|
| 6,215,041 | B1 | 4/2001 | Stice et al. | |
| 6,271,436 | B1 | 8/2001 | Piedrahita et al. | |
| 6,503,698 | B1 | 1/2003 | Dobrinsky et al. | |
| 6,700,037 | B2 | 3/2004 | Damiani et al. | |
| 7,291,461 | B2 * | 11/2007 | Welch et al. | 435/6 |
| 2005/0120400 | A1 | 6/2005 | Day et al. | |
| 2006/0041945 | A1 | 2/2006 | Robl et al. | |
| 2009/0241203 | A1 | 9/2009 | Welsh et al. | |

FOREIGN PATENT DOCUMENTS

| | | |
|---|---|---|
| WO | WO 96/07732 | 3/1996 |
| WO | WO 99/36510 | 7/1999 |
| WO | WO 01/03722 | 1/2001 |
| WO | WO 2005/104835 | 11/2005 |
| WO | WO 2008/121199 | 10/2008 |

OTHER PUBLICATIONS

Rogers (J. Clin. Investigation, Apr. 2008, vol. 118, No. 4, p. 1571-1577).*
Harris (Human Mol Genetics, 1997, vol. 6, No. 13, p. 2191-2193).*
Li (Reproductive Biol. & Endocrin., 2003, vol. 1, 83, p. 1-8).*
Sun (J. Clin. Investigation, Apr. 2008, vol. 118, No. 4, p. 1578-1583).*

(Continued)

*Primary Examiner* — Michael C. Wilson
(74) *Attorney, Agent, or Firm* — Clark & Elbing LLP

(57) ABSTRACT

The present invention provides transgenic, large non-human animal models of diseases and conditions, as well as methods of using such animal models in the identification and characterization of therapies for the diseases and conditions.

2 Claims, 20 Drawing Sheets
(14 of 20 Drawing Sheet(s) Filed in Color)

OTHER PUBLICATIONS

Rogers (Am J Physiol Lung Cell Mol Physiol, May 16, 2008, vol. 295, p. 240-263).*
Welsh (Transactions of the Am. Clin. And Climatological Assoc. 2009, vol. 120, p. 149-162).*
Meyerholz (Am. J. Pathol., Mar. 2010, vol. 176, No. 3, p. 1377-1389).*
Richt (Nature Biotech, Jan. 2007, vol. 25, No. 1, p. 132-139).*
van Heeckeren (Am J Physicol Lung Cell Mol Physiol, 2004, vol. 287, p. 944-952).*
U.S. Appl. No. 60/908,637, filed Mar. 28, 2007, Welsh et al.
U.S. Appl. No. 60/966,971, filed Aug. 30, 2007, Welsh et al.
U.S. Appl. No. 12/283,980, filed Sep. 17, 2008, Welsh et al.
Grosse-Hovest et al., "Cloned Transgenic Farm Animals Produce a Bispecific Antibody for T Cell-Mediated Tumor Cell Killing," Proc. Natl. Acad. Sci. U.S.A. 101:6858-6863, 2004.
Harris, "Towards an Ovine Model of Cystic Fibrosis," Hum. Mol. Genet. 6:2191-2193, 1997.
Hirata et al., "Efficient PRNP Gene Targeting in Bovine Fibroblasts by Adeno-Associated Virus Vectors," Cloning Stem Cells 6:31-36, 2004.
Hao et al., "Production of Endothelial Nitric Oxide Synthase (eNOS) Over-Expressing Piglets," Transgenic Res. 15:739-750, 2006.
Inoue et al., "High-Fidelity Correction of Mutations at Multiple Chromosomal Positions by Adeno-Associated Virus Vectors," J. Virol. 73:7376-7380, 1999.
Kelley et al, "In Vivo Activation of the Cystic Fibrosis Transmembrane Conductance Regulator Mutant Δ,F508 in Murine Nasal Epithelium," Proc. Natl. Acad. Sci. U.S.A. 94:2604-2608, 1997.
Lai et al., "Production of α-1,3-Galactosyltransferase Knockout Pigs by Nuclear Transfer Cloning," Science 295:1089-1092, 2002.
Lai et al., "Creating Genetically Modified Pigs by Using Nuclear Transfer," Reprod. Biol. Endocrinol. 1:1-6, 2003.
Lai et al., "Production of Cloned Pigs by Using Somatic Cells as Donors," Cloning and Stem Cells 5:233-241, 2003.
Lai et al., "A Method for Producing Cloned Pigs by Using Somatic Cells as Donors," Methods Mol. Biol. 254:149-163, 2004.
Lai et al., "Generation of Cloned Transgenic Pigs Rich in Omega-3 Fatty Acids," Nat. Biotechnol. 24:435-436, 2006.
Li et al., "Progress Toward Generating a Ferret Model of Cystic Fibrosis by Somatic Cell Nuclear Transfer," Reprod. Biol. Endocrinol. 1:1-8, 2003.
Li et al., "Cloned Transgenic Swine Via in Vitro Production and Cryopreservation," Biol. Reprod. 75:226-230, 2006.
Liu et al., "Targeted Correction of Single-Base-Pair Mutations with Adeno-Associated Virus Vectors under Nonselective Conditions," J. Virol. 78:4165-4175, 2004.
Liu et al., "Mild Processing Defect of Porcine ΔF508-CFTR Suggests that ΔF508 Pigs May not Develop Cystic Fibrosis Disease," Biochem. Biophys. Res. Comm. 373:113-118, 2008.
Ostedgaard et al., "Processing and Function of CFTR-ΔF508 are Species-Dependent," Proc. Natl. Acad. Sci. U.S.A. 104:15370-15375, 2007.
Park et al., "Production of Nuclear Transfer-Derived Swine that Express the Enhanced Green Fluorescent Protein," Animal Biotechnol. 12:173-181, 2001.
Park et al., "Developmental Potential of Porcine Nuclear Transfer Embryos Derived from Transgenic Fetal Fibroblasts Infected with the Gene for the Green Fluorescent Protein: Comparison of Different Fusion/Activation Conditions," Biol. Reprod. 65:1681-1685, 2001.
Prather et al., "Nuclear Remodeling and Reprogramming in Transgenic Pig Production," Exp. Biol. Med. 229:1120-1126, 2004.
Reynaert et al., "Morphological Changes in the Vas Deferens and Expression of the Cystic Fibrosis Transmembrane Conductance Regulator (CFTR) in Control, ΔF508 and Knock-Out CFTR Mice During Postnatal Life," Mol. Reprod. Dev. 55:125-135, 2000.
Rogers et al., University of Iowa, College of Medicine Research Week poster, Mar. 29, 2006 (also presented in substantially similar form on Feb. 23, 2006 at University of Iowa, Department of Internal Medicine Research Day, Feb. 23, 2006, with the exception of Figure 7).
Rogers et al., University of Iowa, Gene Therapy Center Retreat presentation, Apr. 26, 2006.
Rogers et al., "Gene Targeting of Pig CFTR: Progress Toward a Large Animal Model of Cystic Fibrosis," North American Cystic Fibrosis Meeting, 2006, Ped. Pulm. 41 S29, abstract 231, 2006.
Rogers et al., "Production of *CFTR*-Null and *CFTR*-ΔF508 Heterozygous Pigs by Adeno-Associated Virus-Mediated Gene Targeting and Somatic Cell Nuclear Transfer," J. Clin. Invest. 118:1571-1577, 2008.
Rogers et al., "The Porcine Lung as a Potential Model for Cystic Fibrosis," Am. J. Physiol. Lung Cell Mol. Physiol. 295:L240-L263, 2008.
Verkman, "From the Farm to the Lab: the Pig as New Model of Cystic Fibrosis," Am. J. Physiol. Lung Cell Mol. Physiol. 295:L238-L239, 2008.
Yan et al., "Ubiquitination of Both Adeno-Associated Virus Type 2 and 5 Capsid Proteins Affects the Transduction Efficiency of Recombinant Vectors," J. Virol. 76:2043-2053, 2002.
International Search Report from International Application No. PCT/US2008/002886, dated Aug. 21, 2008 (date of completion of the search) and Sep. 15, 2008 (date of mailing of report).
Written Opinion from International Application No. PCT/US2008/002886, dated Aug. 25, 2008 (date of completion of opinion) and Sep. 15, 2008 (date of mailing of opinion).
International Preliminary Report on Patentability from International Application No. PCT/US2008/002886, dated Aug. 25, 2008 (date of completion of opinion) and Sep. 29, 2009 (date of issuance of report).
Restriction Requirement dated Oct. 29, 2009 from U.S. Appl. No. 12/283,980.
Reply to Restriction Requirement dated Oct. 29, 2009 from U.S. Appl. No. 12/283,980, filed Jan. 29, 2010.
Information Disclosure Statement and Form PTO 1449 from U.S. Appl. No. 12/283,980, filed Jan. 29, 2010.
Office Action dated Mar. 2, 2010 from U.S. Appl. No. 12/283,980.
Reply to Office Action dated Mar. 2, 2010 from U.S. Appl. No. 12/283,980, filed Aug. 23, 2010.
Office Action dated Oct. 29, 2010 from U.S. Appl. No. 12/283,980.

* cited by examiner

METHOD OF IDENTIFYING COMPOUNDS USING A TRANSGENIC PIG MODEL OF CYSTIC FIBROSIS

CROSS-REFERENCE TO RELATED APPLICATIONS

This application claims the benefit of the filing date of U.S. provisional patent application No. 60/908,637, filed Mar. 28, 2007, and U.S. provisional patent application No. 60/966, 971, filed Aug. 30, 2007, the contents of each of which are incorporated herein by reference.

STATEMENT AS TO FEDERALLY SPONSORED RESEARCH

This invention was made with government support under grant number HL51670 awarded by the National Institutes of Health. The government has certain rights in this invention.

FIELD OF THE INVENTION

This invention relates to transgenic, non-human animal models of disease, cells that can be used to make such animals, and methods of using these animals and cells.

BACKGROUND OF THE INVENTION

Many human diseases and conditions are caused by gene mutations. Substantial effort has been directed towards the creation of transgenic animal models of such diseases and conditions, to facilitate the testing of approaches to treatment, as well as to gain a better understanding of disease pathology. Early transgenic animal technology focused on the mouse, while more recent efforts, which have been bolstered by the development of somatic cell nuclear transfer, have included larger animals, including pigs, cows, and goats. This technology has resulted in the production of, for example, pigs in which the gene encoding α-1,3-galactosyltransferase has been knocked out, in efforts to generate organs that can be used in xenotransplantation (see, e.g., Lai et al., Science 295:1089-1092, 2002). Additional applications of this technology include the production of large quantities of human proteins (e.g., therapeutic antibodies; see, e.g., Grosse-Hovest et al., Proc. Natl. Acad. Sci. U.S.A. 101(18):6858-6863, 2004). Substantial benefits may be obtained by the use of somatic cell nuclear transfer technology in the production of large animal models of human disease.

An example of a disease caused by gene mutations is cystic fibrosis (CF), which is an inherited disease that affects many organs of the body, including the lungs, pancreas, sweat glands, liver, and organs of the reproductive tract. The disease is characterized by abnormalities in fluid secretion, which can lead to diverse physiological problems. For example, in the lungs of CF patients, secreted mucus is unusually heavy and sticky, and thus tends to clog small air passages, making it difficult for patients to breath and leading to bacterial infection and inflammation. Repeated lung infections and blockages in CF patients can cause severe, permanent lung damage. Other features of CF arise from the clogging of ducts leading from the pancreas to the small intestine, which blocks the transport of critical digestive enzymes such as amylase, protease, and lipase. This can lead to problems including incomplete digestion, diarrhea, bowel blockage, and weight loss. Digestive complications of CF can also be caused by blockage of liver bile ducts. Due to these and other features of the disease, CF causes progressive disability in patients and ultimately leads to early death.

CF is caused by the presence of a mutation in the gene encoding the cystic fibrosis transmembrane conductance regulator (CFTR) protein, which is a chloride channel found in the membranes of epithelial cells lining passageways of the lungs, liver, pancreas, intestines, and digestive tract, and in the skin. The disease is autosomal recessive, and thus CF patients have mutations in both CFTR alleles, while asymptomatic CF carriers have mutations in only one allele. There are more than 1,200 different known mutations of the CFTR gene that can lead to cystic fibrosis in humans, with some mutations causing milder symptoms than others. However, about 70% of people with CF have the disease due to a particular gene mutation, a deletion of three nucleotides, leading to the loss of a phenylalanine that is normally present at position 508 of the CFTR protein. This form of the disease, often referred to as ΔF508 (CFTR-ΔF508, also called F508del-CFTR), is both the most common and the most severe form of the disease. The loss of phenylalanine at position 508 results in improper CFTR protein folding, which causes retention of the mutant protein in the ER and targets it for degradation before it even reaches the cell membrane. Additionally, this deletion alters channel gating, reducing the rate of channel opening.

There is no cure for CF. Current approaches to treatment include the use of mucous thinning drugs, digestive enzyme supplementation, bronchodilators, respiratory therapy, antibiotics, and lung transplantation. Even given the availability of these approaches to treatment, as the disease progresses, patients typically suffer from an increasingly poor quality of life. New approaches to treating diseases such as CF, which may be identified, for example, by the use of large animal models, are therefore needed for this and other devastating diseases.

SUMMARY OF THE INVENTION

The invention provides large, non-human animal models of human diseases or conditions, in which one or more genes associated with the diseases or conditions include one or more targeted mutations. The animals of the invention can be, for example, ungulates such as, e.g., pigs, cows, sheep, and goats. In one example, the disease or condition is cystic fibrosis and the gene including one or more mutations is a cystic fibrosis membrane transporter gene (CFTR).

The animal models of the invention can include the mutation(s) in one or both alleles of the gene in the genome of the transgenic animal, and the mutation(s) can result in full or partial inactivation of the gene(s). In one example, the mutation includes an insertion of an exogenous nucleic acid molecule and/or a transcription termination sequence. In another example, the mutation substantially eliminates expression of a functional gene product of the targeted gene in cells in which such expression normally takes place, absent the mutation. In the case of an animal with a mutation or mutations in both alleles of a gene, the mutation or mutations in each allele can be identical to one another or can be different.

The invention also provides isolated cells of transgenic, large non-human animal models of human diseases or conditions, in which one or more genes associated with the diseases or conditions include one or more targeted mutations. The animals can be, for example, ungulates, such as, e.g., pigs, cows, sheep, and goats. In one example, the disease or condition is cystic fibrosis and the gene including one or more mutations is a cystic fibrosis membrane transporter gene.

The invention further provides transgenic, large non-human animal models of human diseases and conditions (e.g., pigs), in which one or more endogenous genes associated with the diseases or conditions are knocked-out (i.e., genetically altered in such way as to inhibit the production or function of the product of the gene) and replaced with a homologous wild-type or mutated gene derived from a different animal (e.g., a human). In one example, a pig with its endogenous porcine CFTR knocked-out, expresses a human transgene encoding a CFTR gene, such as the CFTR-Δ508 gene.

Examples of CFTR mutations that can be included in the animals (and cells) of the invention include (i) class I mutations, which result in little or no mRNA production, and thus little or no protein production (e.g., nonsense mutation (e.g., G542X), a frameshift mutation (e.g., 394delTT), a splice junction mutation (e.g., 1717-1GtoA)), (ii) class II mutations, which result in a protein trafficking defect where CFTR is made, but fails to traffic to the cell membrane (e.g., F508del), (iii) class III mutations, which result in CFTR trafficking to the cell membrane, but failing to be properly regulated or responding to cAMP stimulation (e.g., G551D, which fails to respond to cAMP stimulation), (iv) class IV mutations, which result in a CFTR channel function defect (e.g., R117H), and (v) class V mutations, which cause CFTR synthesis defects, resulting in reduced synthesis or defective processing of normal CFTR (e.g., missense mutation (e.g., A455E), or a mutation introduced by alternative splicing (e.g., 3849+10 kbC→T). Additional mutations include 621+1→T, W1282X, R347P, S549I,N,R(A→C), R553X, and N1303K.

The cells of the invention can include the mutation(s) in one or both alleles of the genes in the genomes of the cells, and the mutation(s) can results in full or partial inactivation of the gene(s). In one example, the mutation includes an insertion of an exogenous nucleic acid molecule and/or a transcription termination sequence. In another example, the mutation substantially eliminates expression of a functional gene product of the targeted gene in cells in which such expression normally takes place, absent the mutation. In the case of a cell with a mutation or mutations in both alleles of a gene, the mutation or mutations in each allele can be identical to one another or can be different. In one example, the cells are fetal cells, such as fetal fibroblasts. Additional examples of cell types included in the invention are provided below.

The invention further provides methods of making transgenic, large non-human animal models of diseases or conditions, as described above and elsewhere herein. The methods can include the steps of: (i) introducing one or more mutations into an allele of one or more genes associated with a disease or condition in a cell (e.g., a fetal fibroblast) to generate a donor cell; (ii) introducing the nucleus of the donor cell into a recipient cell (e.g., an enucleated oocyte) to generate an embryo; and (iii) transferring the embryo into a surrogate female. The animals can be, for example, ungulates, such as, e.g., pigs, cows, sheep, and goats. In one example, the disease or condition is cystic fibrosis and the gene including one or more mutations is a cystic fibrosis membrane transporter gene. In a variation of these methods, the donor cell includes one or more mutations in one allele of a gene, and the method is carried out to introduce one or more mutations into the other allele. In another example, the methods further involve breeding an animal that is born from the surrogate female to obtain a homozygous mutant.

The invention also includes methods of identifying therapeutic agents that can be used in the treatment of diseases or conditions (e.g., cystic fibrosis). These methods involve administering one or more candidate therapeutic agents to a transgenic animal, as described above, and monitoring the animal for one or more symptoms of the disease or condition. Detection of improvement in a symptom of the disease or condition indicates the identification of a compound that can be used in the treatment of the disease or condition.

The invention further provides methods of targeting the introduction of mutations into pig cells. These methods involve the steps of providing pig cells (e.g., fetal fibroblasts), using an adeno-associated viral vector to deliver a gene targeting construct to the isolated pig cells, in the absence of cell detachment and reattachment, and selecting gene-targeted clones. The cells are in culture for 30 days or less (e.g., 20 days or less; see below) during the targeting construct delivery and selection steps. These methods can be used, for example, for the introduction of a mutation into a cystic fibrosis transmembrane conductance regulator gene (e.g., the ΔF508 mutation) in the pig cell. Information concerning other examples of mutations that can be used in the invention, as well as the use of the present methods to inactivate or replace genes (e.g., to replace pig genes with human genes), is provided below.

By "donor cell" is meant a cell from which a nucleus or chromatin material is derived, for use in nuclear transfer. As is discussed elsewhere herein, nuclear transfer can involve transfer of a nucleus or chromatin only, as isolated from a donor cell, or transfer of an entire donor cell including such a nucleus or chromatin material.

By "genetic modification," "mutation," or "disruption" of a gene (e.g., a CFTR gene) is meant one or more alterations in gene sequences (including coding sequences and non-coding sequences, such as introns, promoter sequences, and 5' and 3'-untranslated sequences) that alter the expression or activity of this gene by, for example, insertion (of, e.g., heterologous sequences, such as selectable markers, and/or termination signals), deletion, frame shift mutation, silent mutation, nonsense mutation, missense mutation, point mutation, or combinations thereof. In one example, the amino acid sequence encoded by the nucleic acid sequence has at least one amino acid altered as compared to a naturally-occurring sequence. Examples of mutations include the insertion of a polynucleotide into a gene, the deletion of one or more nucleotides from a gene, and the introduction of one or more base substitutions into a gene. Preferred modifications of CFTR sequences are those that lead to one or more features of CF in transgenic animals including a mutation in, or disruption of, both CFTR alleles. As is discussed elsewhere herein, the modifications in the two CFTR alleles of such animals can be identical or different. Further, the modifications can result in a complete lack of functional CFTR production (as in the human ΔF508 mutation), or can result in diminished functional CFTR production, as may be characteristic of less severe forms of the disease.

Examples of such mutations include but are not limited to: i) class I mutations, which result in little or no mRNA production, and thus little or no protein production (e.g., nonsense mutations, G542X; frameshift mutations, 394delTT; and splice junction mutations, 1717-1GtoA), ii) class II mutations, which result in a protein trafficking defect where CFTR is made, but fails to traffic to the cell membrane (e.g., F508del), iii) class III mutations, which are those in which CFTR traffics to the cell membrane, but fails to be properly regulated (e.g., G551D, which fails to respond to cAMP stimulation), iv) class IV mutations, which result in a CFTR channel function defect (e.g., R117H), and v) class V mutations, which cause CFTR synthesis defects, resulting in reduced synthesis or defective processing of normal CFTR (e.g., missense mutations, A455E; alternative splicing, 3849+10 kbCtoT).

In one example, a mutation is introduced by the insertion of a polynucleotide (e.g., a positive selection marker, such as an antibiotic resistance gene (e.g., a neomycin resistance gene)) into an endogenous gene. Optionally, a mutation that is introduced into such an endogenous gene reduces the expression of the gene. If desired, the polynucleotide may also contain recombinase sites flanking the positive selection marker, such as loxP sites, so that the positive selection marker may be removed by a recombinase (e.g., cre recombinase).

By "homologous" genes is meant a pair of genes from two animal species that encode proteins having similar functional and physical properties. The proteins encoded by homologous genes are often very similar in structure and function (although not always), and typically have a common evolutionary origin. The sequence identity is typically equal to or greater than 80% between two gene homologs. One example of a homologous gene pair is the porcine CFTR and human CFTR gene locus.

By "homozygous knock-out non-human mammal" is meant a mammal other than a human in which the two alleles of an endogenous gene (such as the CFTR gene) have been genetically targeted, resulting in a marked reduction or elimination of expression of a functional gene product, which is achieved by gene deletion or disruption. According to this invention, the genetic targeting event at both alleles may or may not be the same. Thus, a non-human mammal, in which the two alleles of an endogenous gene (such as a CFTR gene) have been genetically targeted by two different targeting vectors resulting in the null expression of the gene, would be considered as being a homozygous knock-out non-human mammal. An example of a "knock-in mutation" is one resulting in the insertion of a mutation into an endogenous gene, for example, introducing the ΔF508 or another CF mutation into a CFTR gene.

By animal "knock-out" is meant an animal (e.g., a pig or mouse; also see other animals described herein) having a genome in which the function of a gene has been disrupted, or "knocked-out." A common method of producing disabled genes using recombinant DNA technology involves inserting an antibiotic resistance gene into the normal DNA sequence of a clone of the gene of interest by homologous recombination. This disrupts the action of the gene, thereby preventing it from leading to the production of an active protein product. A cell (or cell nucleus) in which this transfer is successful can be injected into a recipient cell (e.g., an enucleated oocyte) to generate a transgenic animal by nuclear transfer. In another approach, the cell is injected into an animal embryo, producing a chimeric animal. These animals are bred to yield a strain in which all of the cells contain the knocked-out gene.

By "recipient cell" is meant a cell into which a donor cell, a donor cell nucleus, or donor cell chromatin is introduced. Preferably, recipient cells are enucleated prior to nuclear transfer. Examples of recipient cells include oocytes, fertilized zygotes, and two-cell embryos.

By "transgenic, large non-human animal" is meant any non-human animal that includes a genetic modification, as defined herein. Examples of such animals include animals other than mice such as, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). In addition to porcine ungulates, additional ungulates that can be used in the invention include bovine, ovine, and caprine ungulates. Thus, for example, the invention can include the use of cows (e.g., *Bos taurus* or *Bos indicus*), sheep, goats, buffalos, antelopes, oxen, horses, donkeys, mule, deer, elk, caribou, water buffalo, camels, llama, alpaca, and elephants.

The invention provides several advantages, as it provides large, non-human animal models that can be used in the identification and characterization of therapies for genetic diseases. One example of such a disease is cystic fibrosis which, as discussed above, is a devastating disease, leading to increased levels of disability and, eventually, early death. Despite progress in understanding and treating CF, the pathogenesis of the disease is not well understood and therapies remain inadequate. A major impediment to answering questions is the lack of an animal model that shows disease similar to that in humans. Availability of a CF pig will allow investigators to address key problems that have persisted unresolved for years. As a result, it will be possible to develop new treatments, therapies, and preventions.

Further, given the close physiological relationship between humans and large animals, such as pigs, there is an increased likelihood that results obtained using the animal models of the invention can be applied to humans, relative to other animal models (e.g., mice, which do not develop the airway and pancreatic disease typical of human CF). Specifically with respect to pigs, it is noted that pigs and humans have anatomical, histological, biochemical, and physiologic similarities. Further, pigs and humans possess similar abundance of submucosal glands and glycoprotein synthesis/secretion. In addition, pigs and humans have similar respiratory immune systems and pulmonary inflammatory responses, making the pig be a particularly good model for CF disease of humans. Further, the use of human sequences in large animals such as pigs, as in some examples of the invention, provides additional benefits of providing a system that is very similar to that of humans. The invention thus can be used to provide substantial benefits in the treatment of diseases and conditions caused by or associated with gene mutations, such as cystic fibrosis.

Other features and advantages of the invention will be apparent from the drawings, the detailed description, the experimental examples, and the claims.

BRIEF DESCRIPTION OF THE DRAWINGS

The application file contains drawings executed in color (FIGS. 2, 4, 5, 6, 7, 8, 10, 11, 12, 13, 14, 17 and 19). Copies of this patent or patent application with color drawings will be provided by the Office upon request and payment of the necessary fee.

Figure 4:
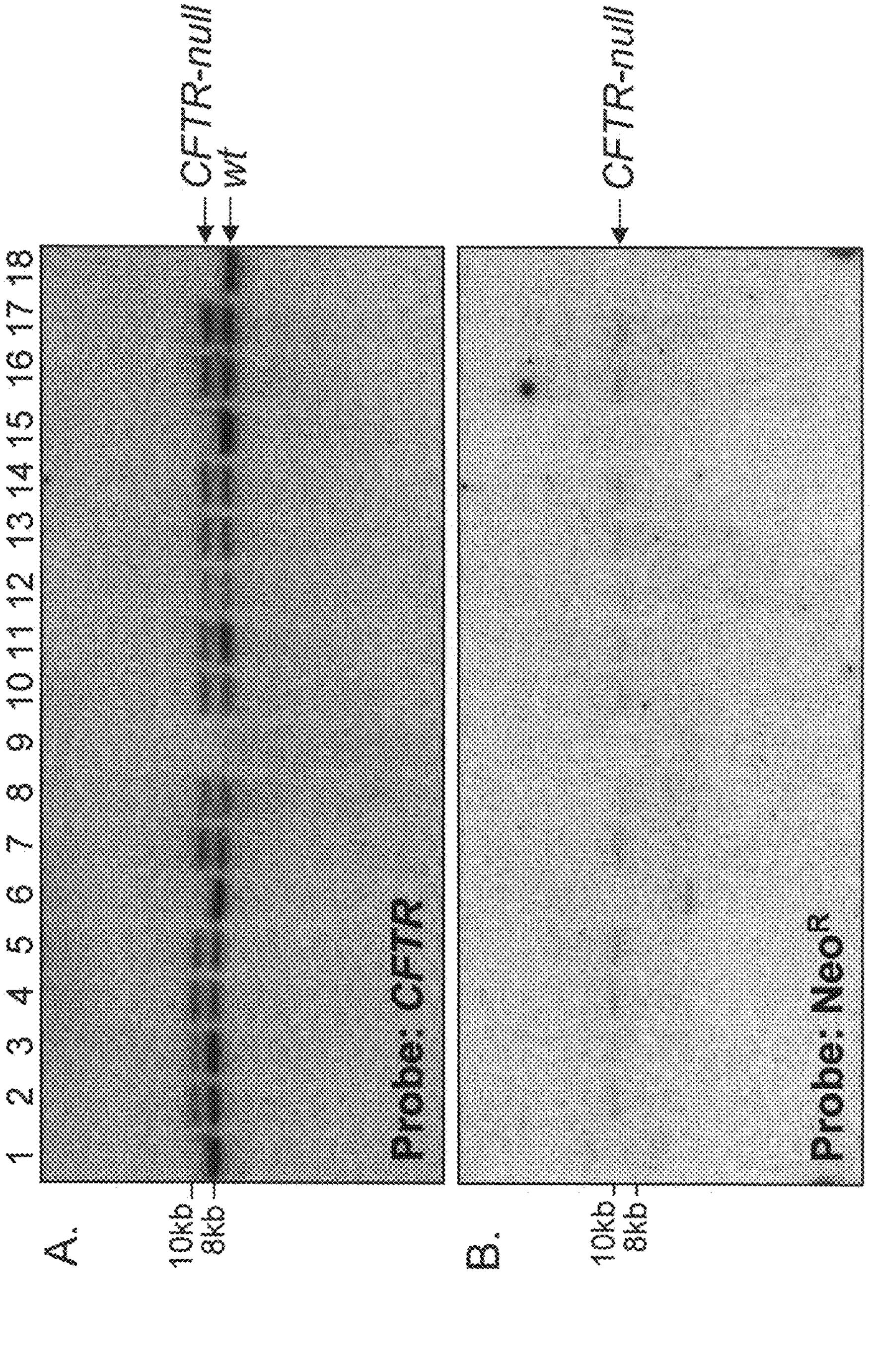
Figure 5:
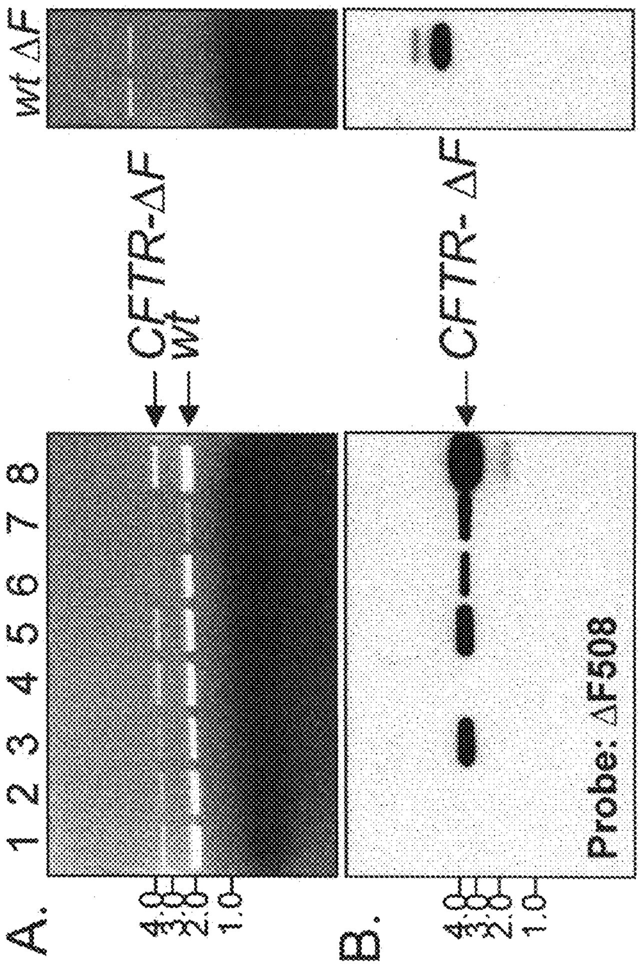

FIG. 4 is a genomic Southern blot of DNA from CFTR-null targeted pig fetal fibroblasts. A) BglII-digested genomic DNA was hybridized with a probe that detects pig CFTR downstream of the targeting vector boundary. CFTR-null-targeted allele yields a ~9.7 kb band and wild-type is ~7.9 kb. These blots also allowed us to identify wells containing monoclonal colonies and those containing more than one type of $G418^R$ colony. For example, wells 3 and 11 appeared to have more intense signals in the wild-type band than the targeted band, indicating that those wells likely contained one targeted clone and one or more random integration events. B) The same digested DNAs were hybridized with a $Neo^R$-specific probe. The CFTR-null-targeted band is at ~9.7 kb. Note that the band in lane 6 likely represents a random integration event, and lane 1 may have two random integration events. Wells 4, 5, 7, 8, 10, 12-14, 16, and 17 are examples of cells that may be ideal nuclear donors for generating a heterozygote animal FIG. 5 shows screening results from CFTR-ΔF508 targeted pig fetal fibroblasts. A) Example of PCR results. Primers amplified a 2.0 kb product from the wild-type allele and a 3.7 kb product from the CFTR-ΔF508 allele. B) Southern blot of the PCR gel using a ΔF508 allele-specific biotin-labeled oligonucleotide. This assay confirms some of the 3.7 kb products contained the ΔF508 mutation. Note that lanes 1, 2, and 4 contain clones that underwent homologous recombination but failed to carry the ΔF508 mutation. On the right, wells contained either wild-type CFTR or CFTR-ΔF508 plasmid DNA. This control is included to ensure that the assay Southern blot is specific to ΔF508.

Figure 6:
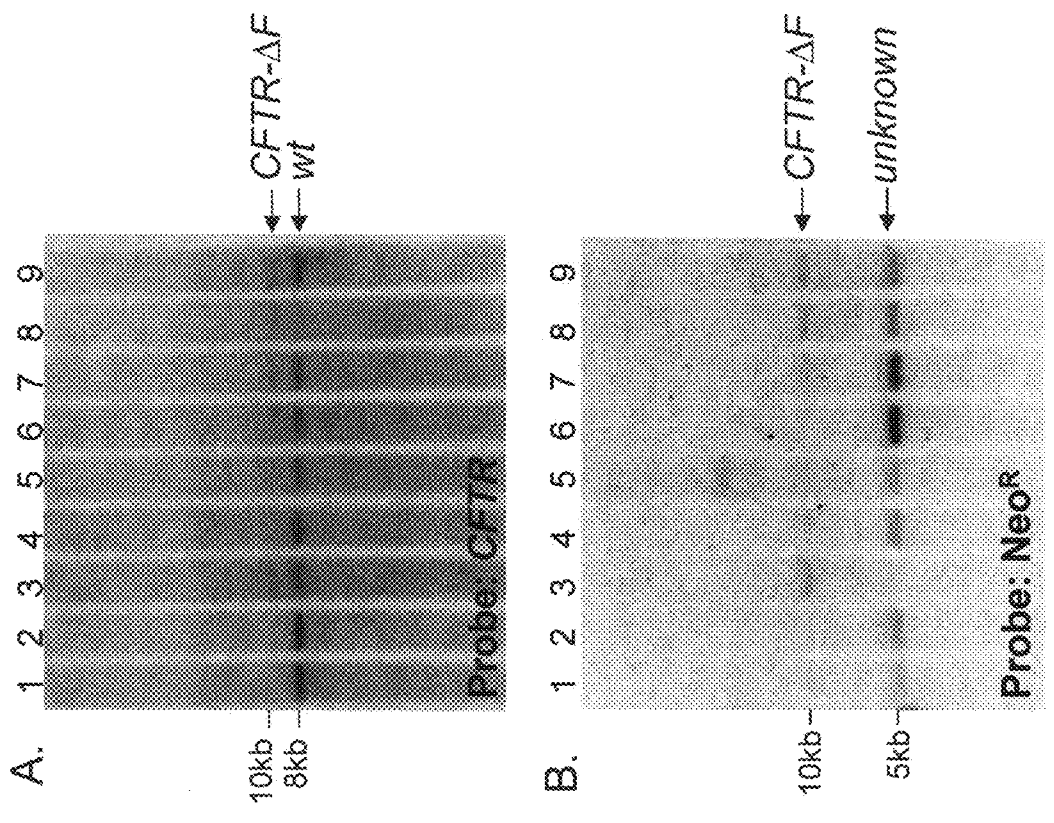

FIG. 6 is a Southern blot of amplified genomic DNA from CFTR-ΔF508 targeted pig fetal fibroblasts. In contrast to our experience with the CFTR-null targeting, the CFTR-ΔF508 targeted cells failed to proliferate after transfer to larger dishes. As a result, we were unable to obtain sufficient quantities of genomic DNA for a genomic Southern blot. Therefore, we used the relatively small amount of DNA for whole genome amplification. A) BglII-digested amplified genomic DNA was hybridized with a probe that detects pig CFTR downstream of the targeting vector boundary. The CFTR-ΔF508-targeted allele yields a ~9.7 kb band and the wild-type is ~7.9 kb. B) Digested DNAs from similar clones were hybridized with a $Neo^R$-specific probe. The CFTR-ΔF508-targeted band is at ~9.7 kb. Note that all lanes in this Southern blot contain an intense band at ~5 kb. This band was also present in non-infected fibroblast control DNA wells. This probe is possibly hybridizing to the endogenous PGK promoter sequence, because the probe includes some PGK promoter sequence. Consistent with this, the $Neo^R$-probed blot in FIG. 4A also contains a faint band at 5 kb in all samples if markedly overexposed.

Figure 7:
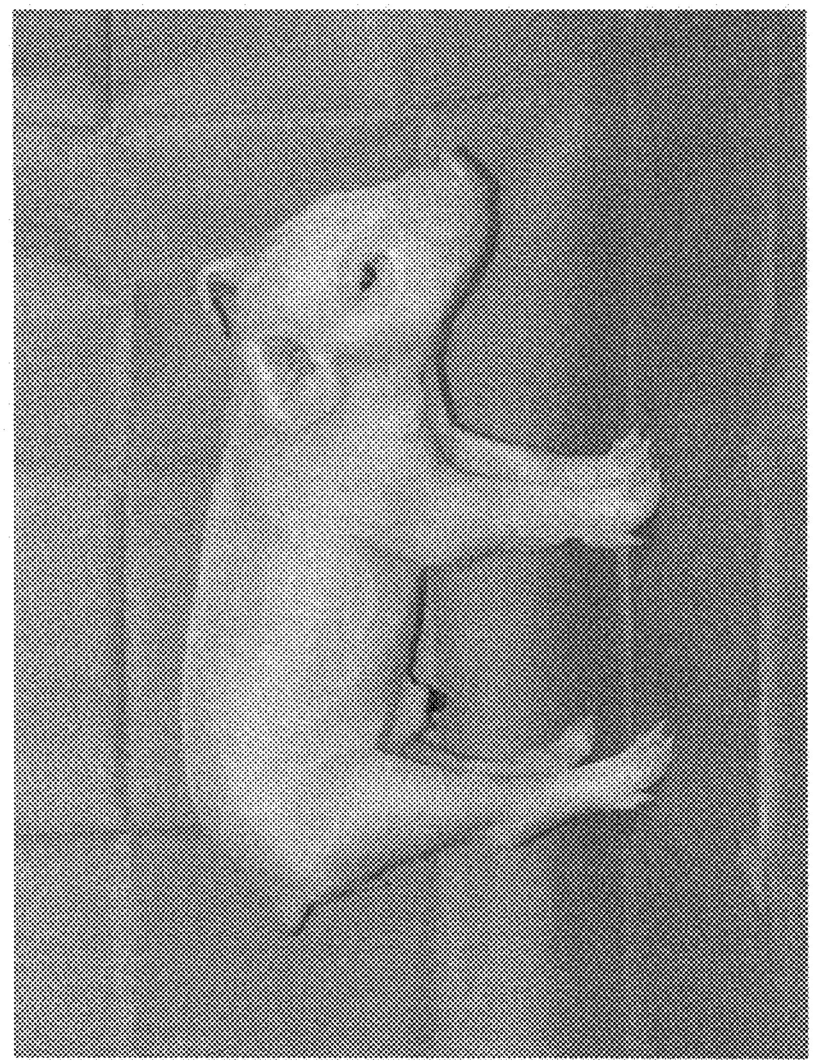

FIG. 7 is a photograph of the first CFTR+/− piglet taken at one day of age.

Figure 8:
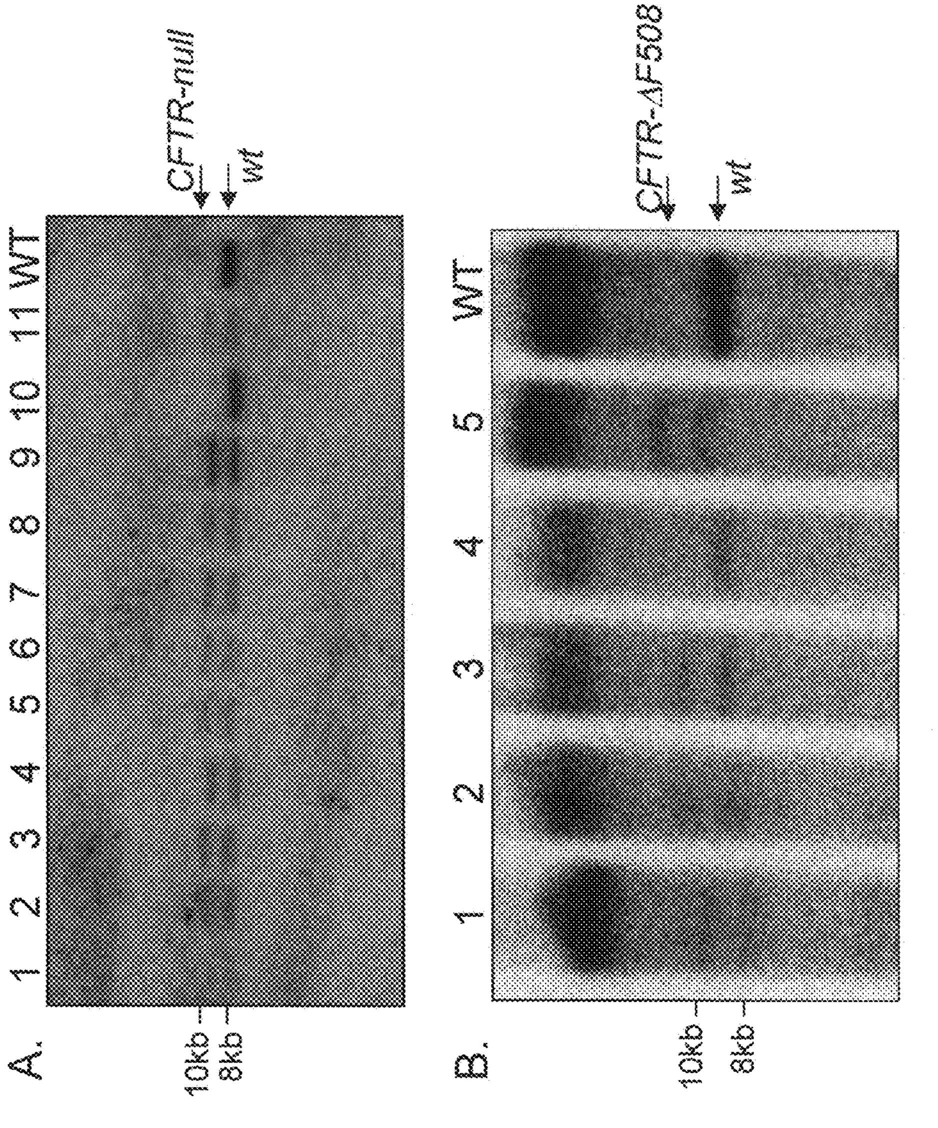

FIG. 8 is a Southern blot of genomic DNA from CFTR-targeted pigs. BglII-digested genomic DNA was hybridized with a probe that detects pig CFTR downstream of the targeting vector boundary, shown in FIG. 2. CFTR-null and CFTR-ΔF508-targeted alleles produced a ~9.7 kb band, and wild-type is ~7.9 kb. A) CFTR-null. Lanes 1-11 contain DNA from individual cloned pigs. Note that pig 10 was wild-type. WT well contains DNA from a wild-type control. B) CFTR-ΔF508. Lanes 1-5 contain DNA from individual cloned pigs. Note that pig 4 was wild-type. WT well contains DNA from a wild-type control.

Figure 9:
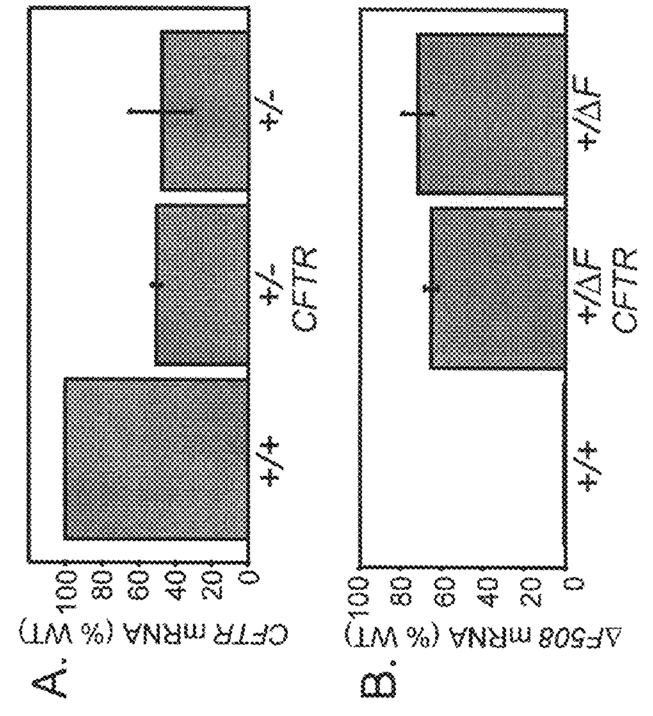

FIG. 9 shows CFTR mRNA expression in CFTR+/− and CFTR+/ΔF508 pigs. A) Quantitative RT-PCR was used to measure wild-type CFTR mRNA levels in rectal epithelial samples from CFTR+/− and wild-type pigs. B) Quantitative RT-PCR was used to measure ΔF508-CFTR mRNA relative to wild-type mRNA levels in CFTR+/ΔF508 and wild-type pigs. Error bars represent S.D.

Figure 10:
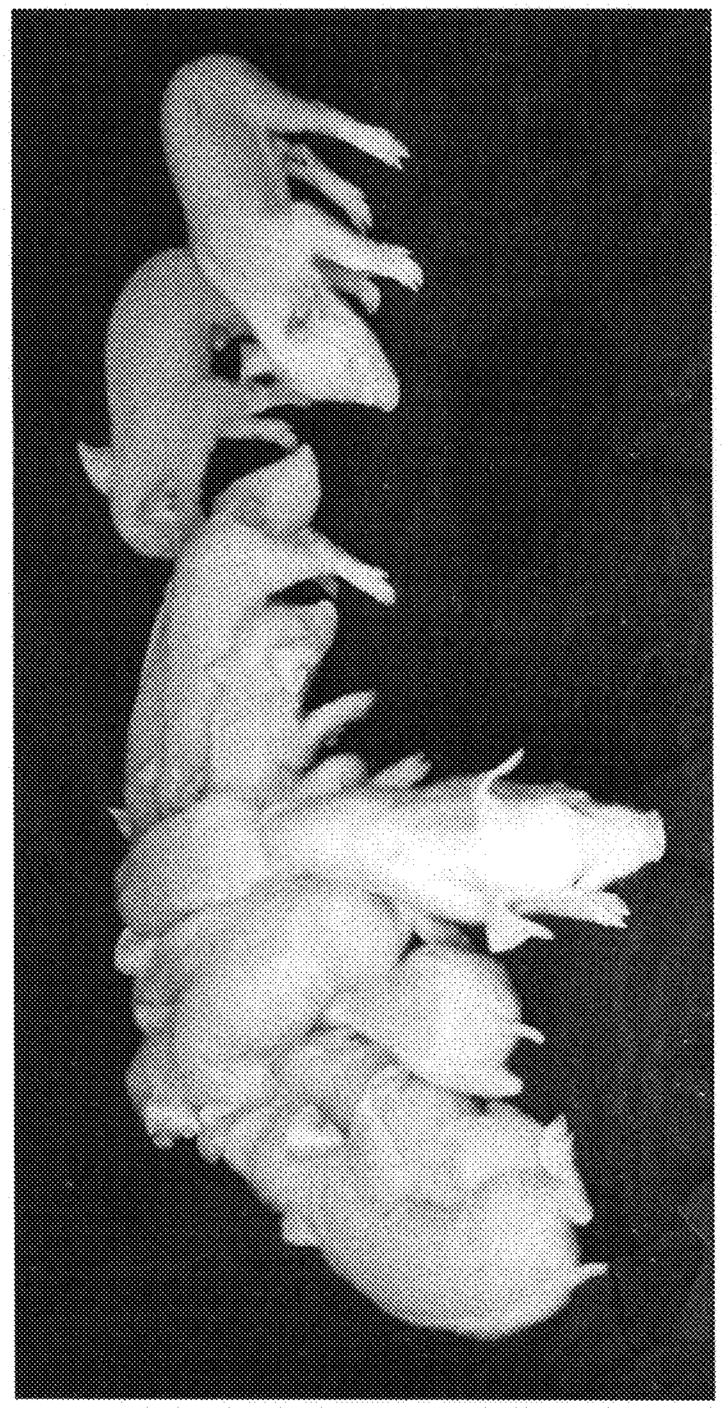

FIG. 10 is a photograph of CFTR+/+, +/−, and −/− piglets at one day of age.

Figure 11:
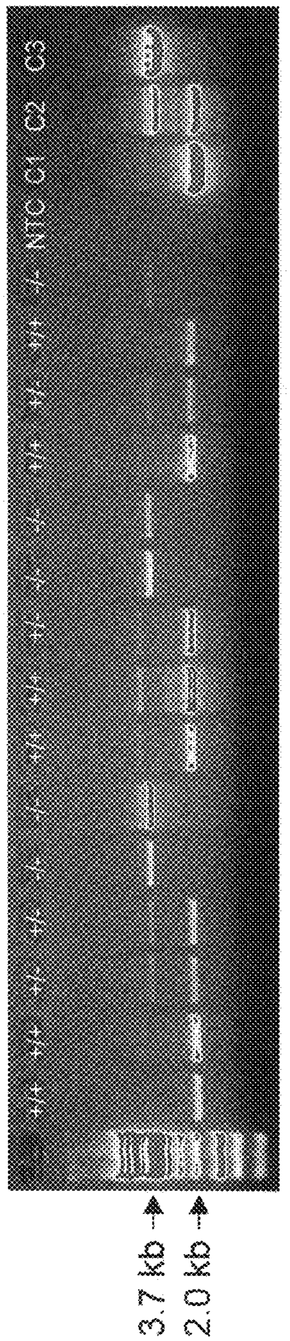

FIG. 11 shows piglet genotyping by PCR. This gel shows the genotyping results of 15 piglets. Wild-type CFTR yielded a product of 2.0 kb and targeted CFTR yielded a product of 3.7 kb. NTC is no template control. CFTR+/+control is in lane C1, CFTR+/− control is in lane C2, and CFTR −/− control is in lane C3.

Figure 12:
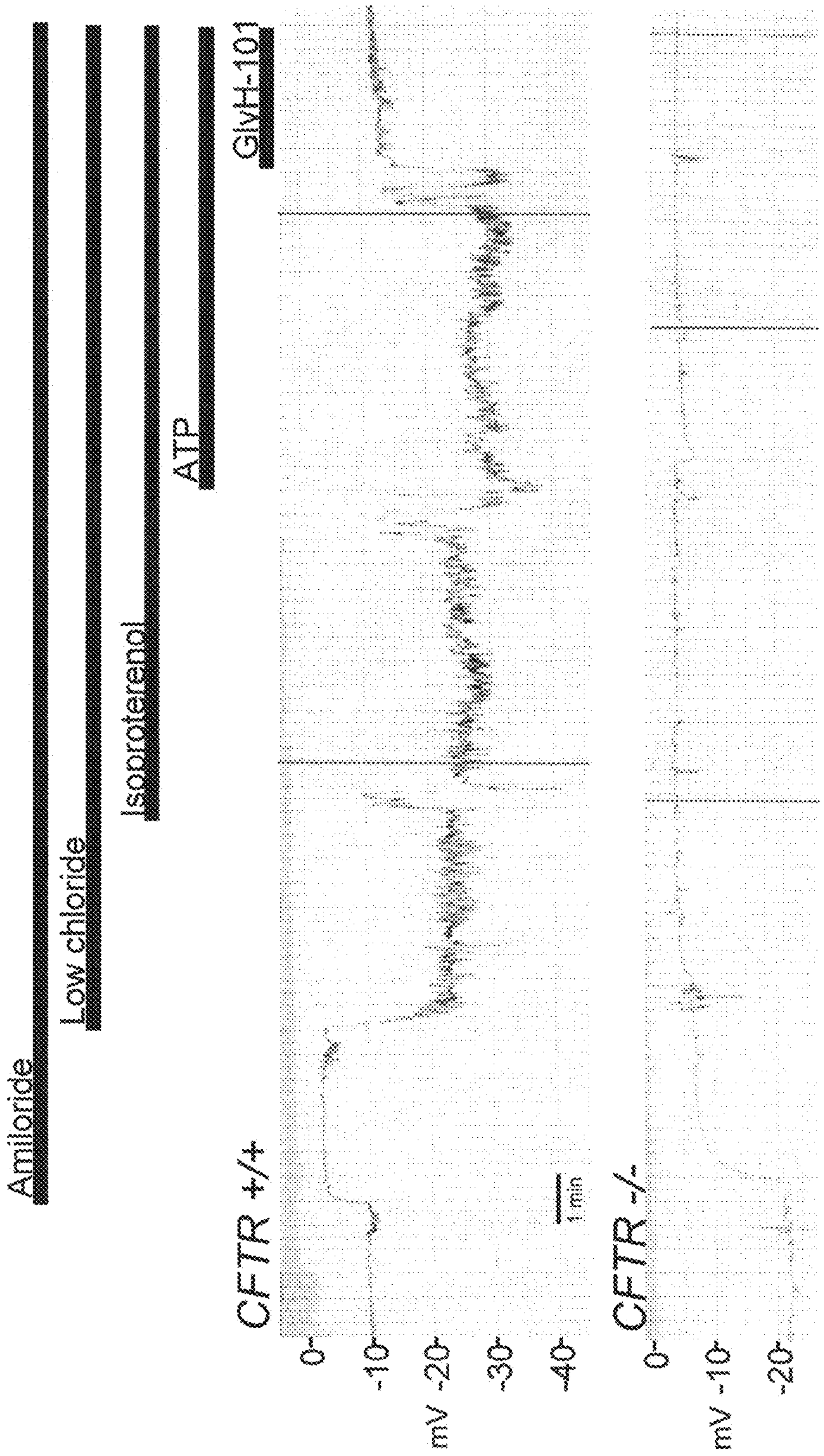

FIG. 12 shows nasal Vt in CFTR+/+ and CFTR −/− piglets. Amiloride, low chloride solution, isoproterenol, ATP, and CFTR inhibitor GlyH-101 were applied as indicated. Vertical (red) lines indicate positions where original traces were scanned and spliced together for the figure.

Figure 13:
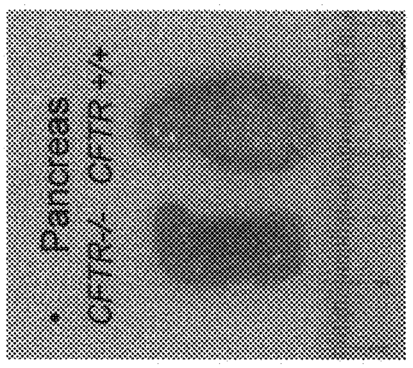

FIG. 13 is a photograph of pancreata from CFTR −/− and CFTR+/+ pigs.

Figure 14:
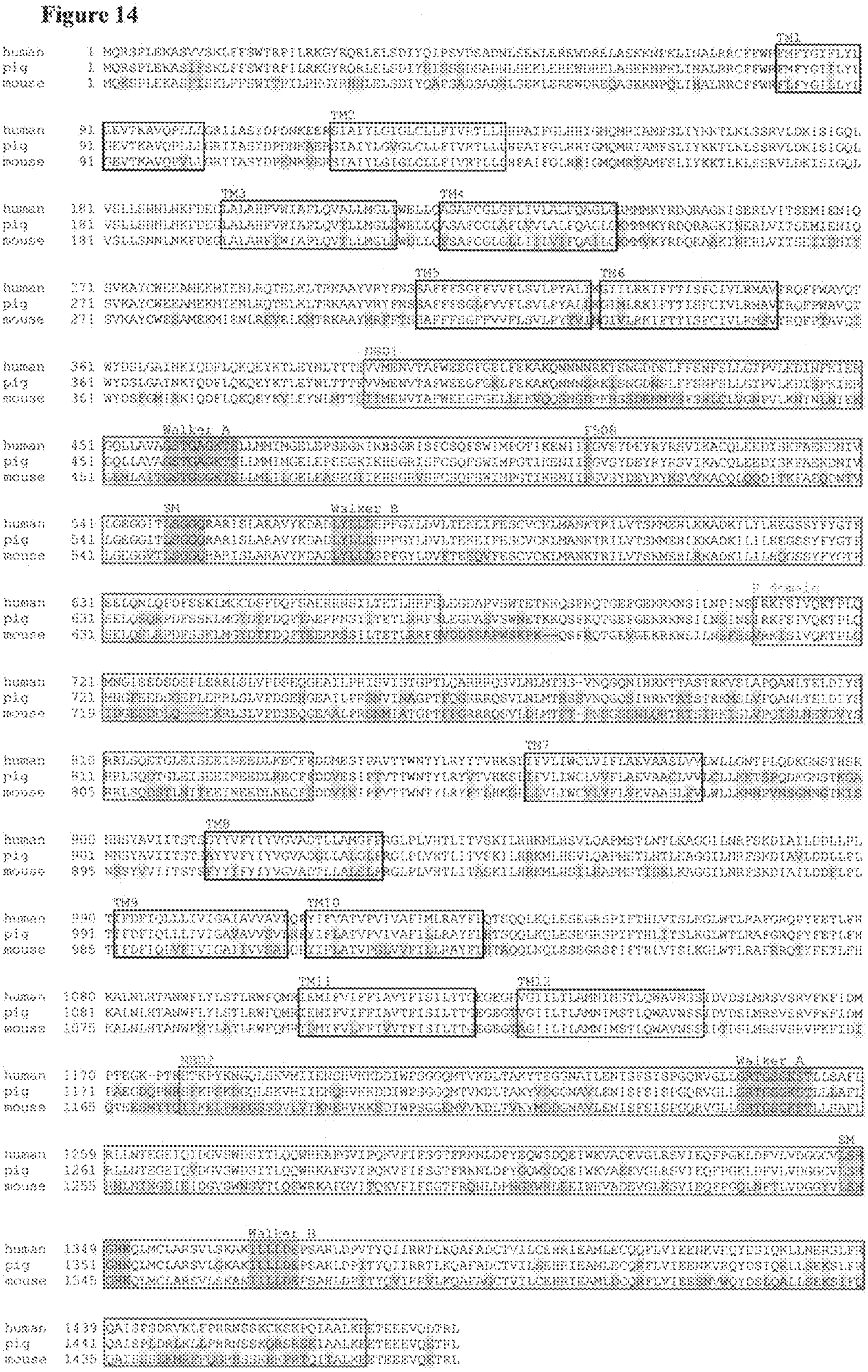

FIG. 14 is an amino acid sequence alignment of human, pig, and mouse CFTR. Transmembrane domains (TM), nucleotide-binding domains (NBD), and the R domain are boxed and labeled. Walker A and B motifs, signature motifs (SM), and F508 are shaded. The alignment was generated using ClustalW. The NBD boundaries are based on the NBD1 crystal with the NBD2 boundaries based on amino acids counting up from Walker A and down from Walker B.

Figure 15:
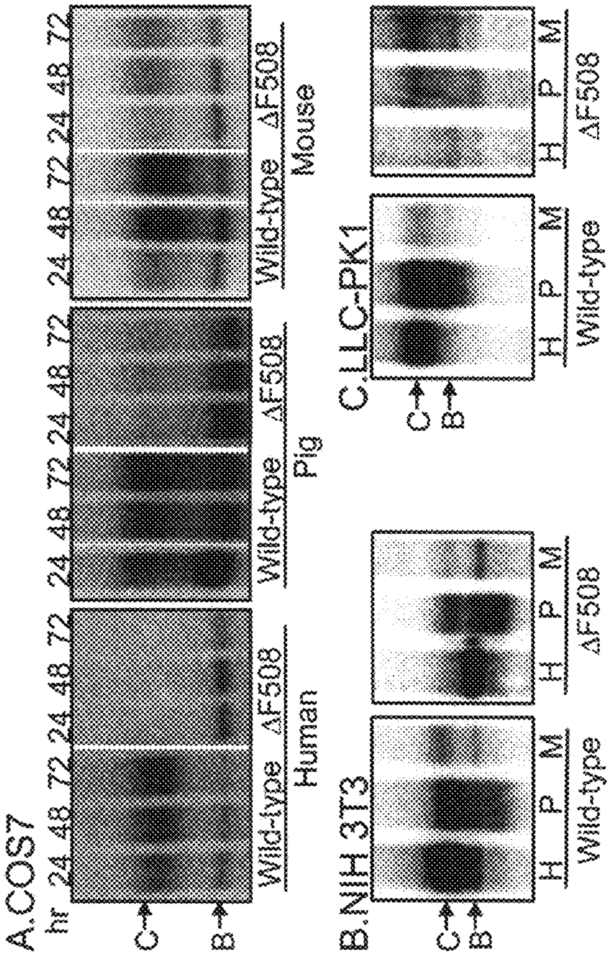

FIG. 15 shows that pig and mouse CFTR-ΔF508 produce some mature band C protein. The images show immunoprecipitated and in vitro phosphorylated wild-type and ΔF508 CFTR of human, pig, and mouse. A. Constructs were expressed for 24, 48, and 72 hours in COS7 cells. B and C. Constructs were expressed for 48 hours in NIH-3T3 (B) and LLC-PK1 (C) cell lines. H, human; P, pig; M, mouse. Bands B and C are indicated by arrows.

Figure 16:
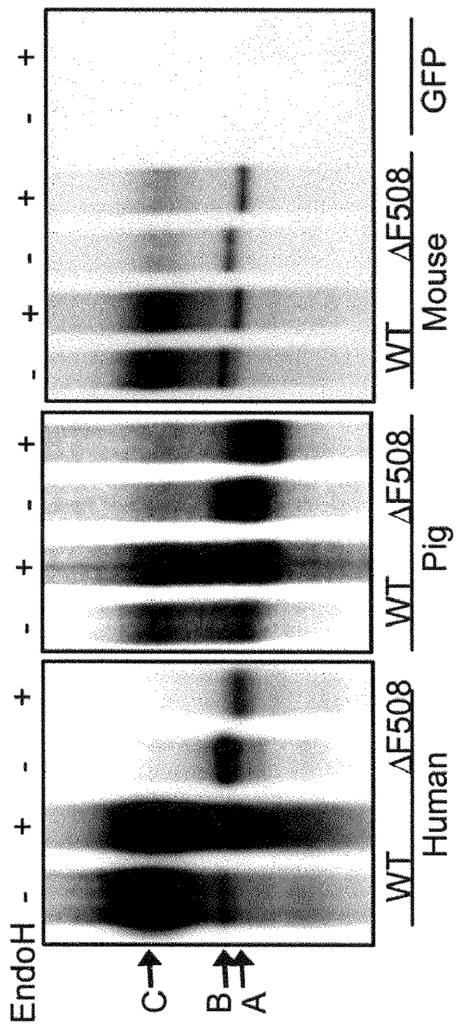

FIG. 16 shows that fully glycosylated pig and mouse ΔF508 are not endoglycosidase-H sensitive. The images show immunoprecipitated and in vitro phosphorylated human, pig, and mouse wild-type and ΔF508 CFTR incubated in the presence (+) or absence (−) of 10 mU of endoglycosidase H. Human CFTR was from electroporated COS7 cells; we expressed pig and mouse CFTR using adenoviral vectors. The last 2 lanes are COS7 cells infected with Ad-GFP. Bands A, B, and C are indicated by arrows.

Figure 17:
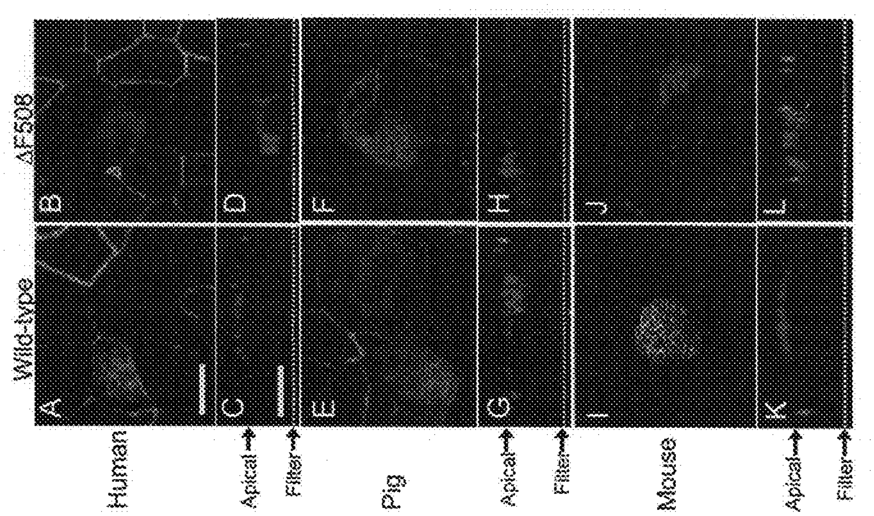

FIG. 17 shows that human, pig, and mouse wild-type CFTR and pig and mouse CFTR-ΔF508 are expressed on the apical surface of differentiated airway epithelia. Immunostaining of differentiated human CF airway epithelia expressing human, pig, and mouse wild-type and ΔF508 CFTR. Data are X-Y (A,B,E,F,I,J) and X-Z (C,D,G,H,K,L) confocal images. CFTR immunostaining is in green and ZO-1 (tight junction) in red. Apical membrane is shown by arrow and filter (at the basal membrane) is indicated by dotted line. In panel B, faint staining of CFTR-ΔF508 is visible beneath the apical surface. Bar indicates 10 μm.

Figure 18:
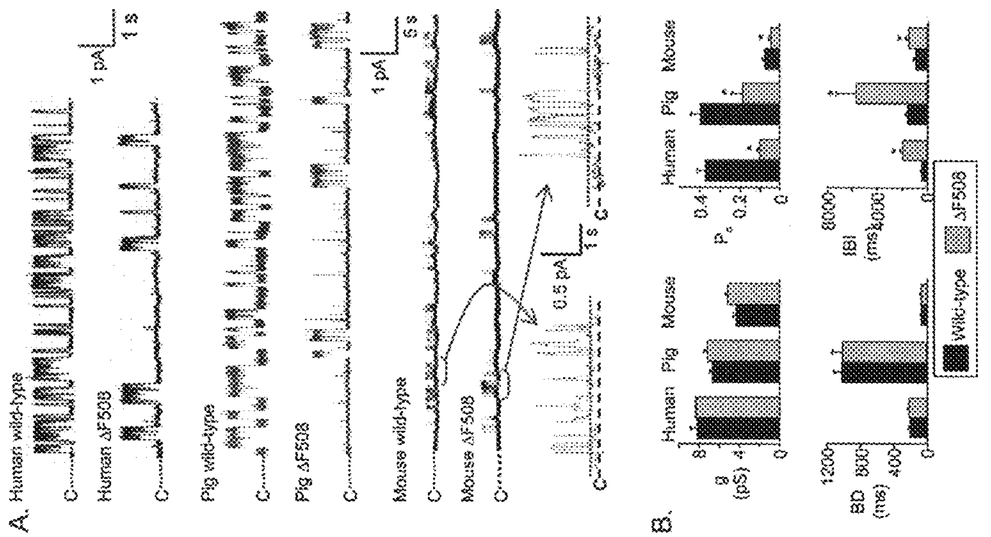

FIG. 18A shows single-channel currents from human, pig, and mouse wild-type and ΔF508 CFTR. Representative current traces from excised, inside-out patches of HeLa cells containing single channels of human, pig, and mouse wild-type and ΔF508 CFTR. Holding voltages were human at −80 mV, pig at −100 mV, mouse wild-type at −50 mV, and mouse ΔF508 at −80 mV. Human tracings were from cells incubated at reduced temperature and then studied at 37° C. and are taken from Teem et al. (Receptors Channels 4:63-72, 1996); pig and mouse channels were from cells incubated at 37° C. and studied at ~25° C. Expanded tracings on bottom show sub-conductance in mouse wild-type and ΔF508 CFTR. FIG. 18B shows the properties of wild-type and ΔF508-CFTR. Data are mean±SEM for single-channel conductance (g), open state probability ($P_o$), burst duration (BD), and interburst interval (IBI). n=4-5 membrane patches for each. Asterisks indicate $p<0.05$ compared to wild-type CFTR using Mann-Whitney Rank Sum test. Note that values for human CFTR and CFTR-ΔF508 were taken from Teem et al. (Receptors Channels 4:63-72, 1996).

Figure 19:
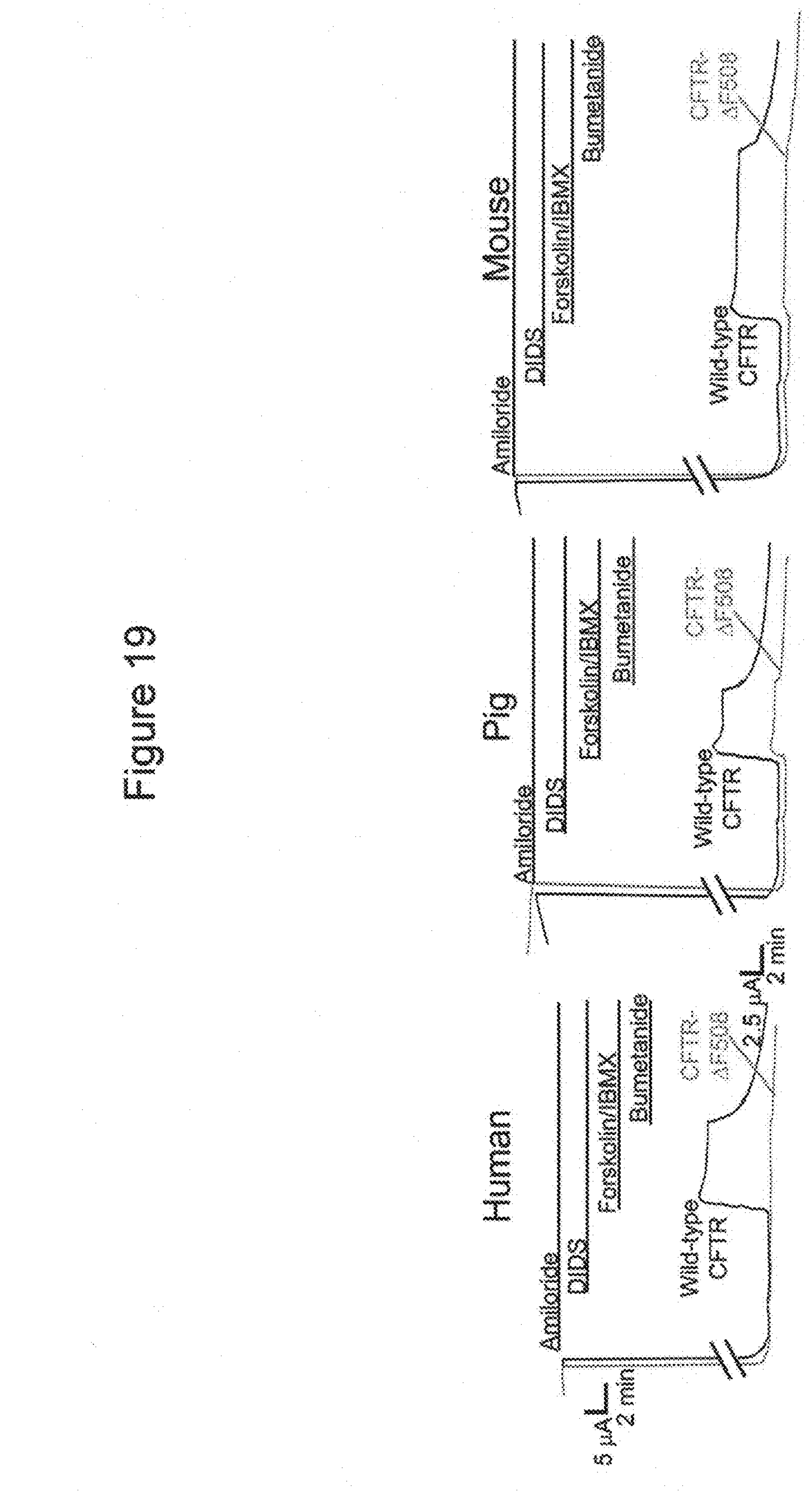

FIG. 19 shows transepithelial currents in human CF airway epithelia expressing human, pig, and mouse CFTR and CFTR-ΔF508. Examples of current traces of human, pig, and mouse wild-type CFTR and CFTR-ΔF508 expressed in differentiated human CF airway. Agents were present during times indicated by bars.

Figure 20:
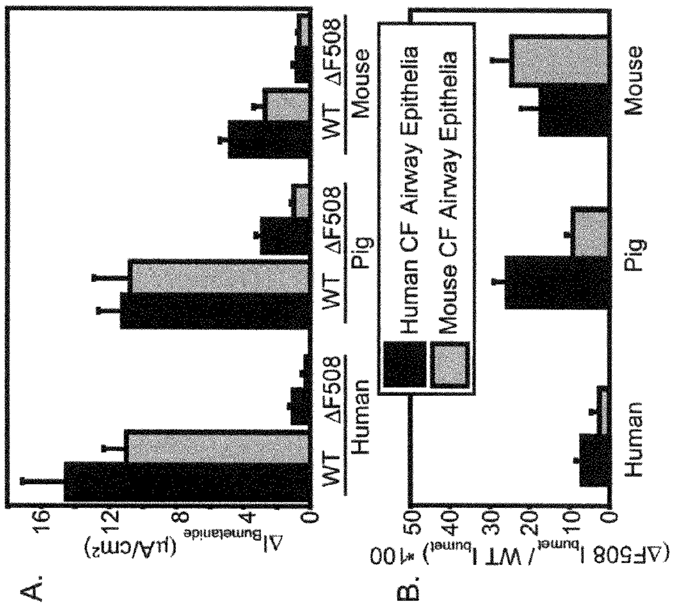

FIG. 20 shows the bumetanide-sensitive cAMP-stimulated current in differentiated CF airway epithelia. A. Currents in human and mouse airway epithelia expressing human, pig, and mouse wild-type CFTR and CFTR-ΔF508 CFTR after subtraction of currents from GFP-expressing control epithelia. B. Bumetanide-inhibited current in CF epithelia expressing CFTR-ΔF508 as a percentage of bumetanide-inhibited current in CF epithelia expressing wild-type CFTR of each species.

DETAILED DESCRIPTION OF THE INVENTION

The invention provides animal models of human disease (e.g., cystic fibrosis (CF)), which can be used in the identification and characterization of approaches for treating the diseases and conditions. As is discussed further below, the animal models of the invention are large, non-human animals, such as pigs, which have been genetically modified to include one or more mutations in a gene associated with a particular disease or condition (e.g., the cystic fibrosis transmembrane regulator (CFTR) gene in CF). The genetic modifications can result in the animals having one or more symptoms characteristic of the disease or condition. Animals exhibiting such symptoms are particularly advantageous in the development of therapeutic approaches, as candidate drugs and other approaches to treatment can be evaluated for effects on the symptoms in such animals. Thus, in addition to the animal models themselves, the invention also provides methods of using the animals for identifying and characterizing treatments. Further, the invention includes methods of making transgenic, large non-human animal models and cells that can be used in these methods. The animal models systems, methods, and cells of the invention are described further, below.

In addition to animals including knock-outs or mutations in endogenous genes, the invention also includes transgenic, large non-human animal models of human diseases and conditions (e.g., pigs), in which one or more endogenous genes associated with the diseases or conditions are knocked-out (i.e., genetically altered in such way as to inhibit the production or function of the products of these genes) and replaced with a comparable wild-type or mutated gene derived from a different animal (e.g., a human). In one example, a pig with its endogenous porcine CFTR knocked-out expresses a human transgene encoding a mutated CFTR protein, such as the CFTR-Δ508 gene (i.e., a CFTR−/−, hCFTR-ΔF508 pig). Alternatively, the human transgene may encode a normal, wild-type copy of a gene of interest (e.g., CFTR). These embodiments of the invention are especially useful for the generation of non-human animal models of human diseases and conditions that can be used to test existing and potential therapeutics that may only (or may preferentially) modulate or treat the disease when contacting, or being in the presence of, human copies of the disease gene or protein in question.

The invention is described herein in reference to animal models of CF, which are generated by mutation, deletion, or replacement of the CFTR gene. However, the methods of the invention are also applicable to the development of animal models of additional diseases and conditions, examples of which are provided below.

The transgenic animals of the invention can be made using the following general strategy. Briefly, the genome of a cell (e.g., a fetal fibroblast) from an animal of interest, such as a pig, is genetically modified by, for example, gene targeting by homologous recombination, to create a "donor cell." According to the methods of the invention, the genetic modification results in at least partial inactivation of a gene associated with a particular disease or condition (e.g., a CFTR gene in CF), as will be described in further detail below. The nucleus of such a genetically modified donor cell (or the entire donor cell, including the nucleus) is then transferred into a so-called "recipient cell," such as an enucleated oocyte. After activation and, typically, a brief period of in vitro culture, the resulting embryo is implanted into a surrogate female in which development of the embryo proceeds. Typically, the donor cell, oocyte, and surrogate female are of the same species, but the sources can be different species, as is known in the art.

Details of methods for making large genetically modified animals, such as pigs, according to the invention, are provided below. Additional information concerning methods for making genetically modified pigs and other large animals is known in the art and can also be used in the present invention (see, e.g., US 2005/0120400 A1; U.S. Pat. No. 5,995,577; WO 95/16670; WO 96/07732; WO 97/00669; WO 97 00668; WO 2005/104835; Lai et al., Reproductive Biology and Endocrinology 1:82, 2003; Hao et al., Transgenic Res. 15:739-750, 2006; Li et al., Biology of Reproduction 75:226-230, 2006; Lai et al., Nature Biotechnology 24(4):435-436, 2006; Lai et al., Methods in Molecular Biology 254(2):149-163, 2004; Lai et al., Cloning and Stem Cells 5(4):233-241, 2003; Park et al., Animal Biotechnology 12(2):173-181, 2001; Lai et al., Science 295:1089-1092, 2002; Park et al., Biology of Reproduction 65:1681-1685, 2001; the contents of each of which are incorporated herein by reference).

The transgenic animals of the invention can be any non-human mammals, including, for example, ungulates. Examples of ungulates that can be used in the invention include members of the orders Perissodactyla and Artiodactyla, such as any members of the family Suidae, and in particular any member of the genus *Sus*, such as *Sus scrofa*, which is also known as the domestic pig or a subspecies thereof (*Sus scrofa domestica*). In one specific example, the animal is a miniature swine that is a descendent from the miniature swine described by Sachs et al., Transplantation 22:559, 1976. In addition to porcine ungulates, additional ungulates that can be used in the invention include bovine, ovine, and caprine ungulates. Thus, for example, the invention can include the use of cows (e.g., *Bos taurus* or *Bos indicus*), sheep, goats, buffalos, antelopes, oxen, horses, donkeys, mule, deer, elk, caribou, water buffalo, camels, llama, alpaca, and elephants.

The invention includes animals in which only one allele of a targeted gene (e.g., CFTR) is disrupted, mutated, or replaced with the other allele remaining unaffected. These animals, which are referred to herein as “heterozygous” or “hemizygous” animals, can be used, for example, in breeding approaches to generate homozygous mutants, if desired, for example, in the case of diseases caused by homozygous recessive mutations. These animals can also be used as animal models themselves, in the case of diseases caused by autosomal dominant mutations.

Also included in the invention are homozygous mutant animals, in which both alleles of a target gene (e.g., CFTR) are disrupted or mutated, by the same or different mutations (or replaced with the same or different gene(s), optionally with the same or different mutations). In addition to being obtainable by breeding approaches involving hemizygous animals, homozygous mutant animals can also be obtained using an approach in which a cell (e.g., a fetal fibroblast) including a mutation in one allele, such as a cell obtained from an animal produced using the method summarized above, is subjected to gene targeting by homologous recombination to achieve modification of the remaining allele. The resulting donor cell can then be used as a source of a modified nucleus for nuclear transfer into a recipient cell, such as an enucleated oocyte, leading to the formation of a homozygous mutant embryo which, when implanted into a surrogate female, develops into a homozygous mutant animal.

A target gene (e.g., a CFTR gene) can be subject to genetic modification in any appropriate cell type of a species for which it is desired to create an animal model of a disease associated with mutation of the gene, according to the invention. As is understood in the art, it is necessary to be able to culture and carry out homologous recombination in a cell that is to be used as a donor cell. A particular example of such a cell, which is described in more detail below in connection with pigs, in the experimental examples, is the fetal fibroblast. These cells can be obtained using, for example, the approach described in U.S. Patent Application Publication 2005/0120400 and other references cited herein.

The invention also includes the use of other cell types that may be present in the cell preparations obtained using the method described in U.S. Patent Application Publication 2005/0120400. Additional examples of cells that can be used as donor cells in making the transgenic animals of the invention include other fetal cells, placental cells, or adult cells. Specific examples of such cells for gene targeting include differentiated cells such as fibroblasts, epithelial cells, neural cells, epidermal cells, keratinocytes, hematopoietic cells, melanocytes, chondrocytes, B-lymphocytes, T-lymphocytes, erythrocytes, macrophages, monocytes, placental, and muscle cells.

If a cell to be genetically altered is derived from an embryo or a fetus, the cell (e.g., a fetal cell or placental cell) can be isolated at any time during the gestation period until the birth of the animal, which may or may not be itself genetically altered. In the case of a pig, such cells can be obtained, for example, between 20 to 90 days of gestation, between 25 to 60 days of gestation, between 30 to 45 days of gestation, or between 35 to 40 (e.g., at 35 days) of gestation. The time periods for obtaining cells from other animals is known in the art (see, e.g., WO 2005/104835).

Gene targeting carried out to make the cells and animals of the invention can result in gene inactivation by disruption, removal, modification, or replacement of target gene sequences. For example, inactivation can take place by the insertion of a heterologous sequence and/or a stop codon into a target gene. A specific example of this type of inactivation, in the context of a CFTR gene, is described in the experimental examples, below. As is known in the art, inserted sequences can replace previously existing sequences in a gene or can be added to such sequences, depending on the design of the targeting construct. Also as is known in the art, the design of targeting constructs can be altered, depending upon whether it is desired to completely knock out the function of a gene or to maintain some level of reduced function. In the case of CFTR, for example, complete knock out of function is consistent with the most common form of CF (ΔF508; see above), but other, less dramatic changes may be desirable for the generation of models of disease maintaining some CFTR function. Such changes may be achieved by, for example, replacement with sequences that are identical to wild-type sequences, except for the presence of specific mutations giving rise to features of the target disease. In other approaches, coding sequences are not altered or are minimally altered and, rather, sequences impacting expression of a target gene, such as promoter sequences, are targeted. In any case, selectable marker insertion is often desirable to facilitate identification of cells in which targeting has occurred. If desired, such markers or other inserted sequences can later be removed by, e.g., cre-10× or similar systems.

A CFTR−/− (i.e., knock-out), hCFTR-ΔF508 pig can be made numerous ways, including, but not limited to: i) introducing a human CFTR-ΔF508 cDNA, partial human CFTR-ΔF508 gene, or entire human CFTR-ΔF508 gene into pig CFTR−/− cells, selecting for human CFTR-ΔF508 expression, and using these cells as nuclear donors in somatic cell nuclear transfer, and ii) introducing a human CFTR-ΔF508 cDNA, partial human CFTR-ΔF508 gene, or entire human CFTR-ΔF508 gene into pig CFTR−/− into matured oocytes, fertilizing, then transferring to a recipient female. The human CFTR sequence is described, for example, by Riordan et al., Science 245(4922):1066-1073, 1989 (erratum in Science 245 (4925):1437, 1989)). Human, pig, and mouse CFTR sequences are also provided in SEQ ID NOs:1-6.

As is known in the art, targeted gene modification requires the use of nucleic acid molecule constructs having regions of homology with a targeted gene (or flanking regions), such that integration of the construct into the genome alters expression of the gene, either by changing the sequence of the gene and/or the levels of expression of the gene. Thus, to alter a gene, a targeting construct is generally designed to contain three main regions: (i) a first region that is homologous to the locus to be targeted (e.g., the CFTR gene or a flanking sequence), (ii) a second region that is a heterologous polynucleotide sequence (e.g., encoding a selectable marker, such as an antibiotic resistance protein) that is to specifically replace a portion of the targeted locus or is inserted into the targeted locus, and (iii) a third region that, like the first region, is homologous to the targeted locus, but typically is not contiguous with the first region of the genome. Homologous recombination between the targeting construct and the targeted wild-type locus results in deletion of any locus sequences between the two regions of homology represented in the targeting vector and replacement of that sequence with, or insertion into that sequence of, a heterologous sequence that, for example, encodes a selectable marker. In the case of targeting transcriptionally inactive genes, such as, for example, the CFTR gene in fibroblasts, or a gene having only very low levels of transcription, the constructs of the invention can include a promoter, such as a PGK promoter, which drives expression of the selectable marker (e.g., Neo). Use of such promoters may not be required in cases in which transcriptionally active genes are targeted, if the design of the construct results in the marker being transcribed as directed by an endogenous promoter. Exemplary constructs and vectors for carrying out such targeted modification are described herein. However, other vectors that can be used in such approaches are known in the art and can readily be adapted for use in the invention.

In order to facilitate homologous recombination, the first and third regions of the targeting vectors (see above) include sequences that exhibit substantial identity to the genes to be targeted (or flanking regions). By "substantially identical" is meant having a sequence that is at least 80%, 90%, 95%, 98%, or 100% identical to that of another sequence. Sequence identity is typically measured using BLAST® (Basic Local Alignment Search Tool) or BLAST® 2 with the default parameters specified therein (see, Altschul et al., J. Mol. Biol. 215:403-410, 1990; Tatiana et al., FEMS Microbiol. Lett. 174:247-250, 1999). These software programs match similar sequences by assigning degrees of homology to various substitutions, deletions, and other modifications. Thus, sequences having at least 80%, 90%, 98%, 99%, or even 100% sequence identity with the targeted gene loci can be used in the invention to facilitate homologous recombination.

The total size of the two regions of homology (i.e., the first and third regions noted above) can be, for example, approximately 2-25 kilobases (e.g., 4-20, 5-15, or 6-10 kilobases), and the size of the second region that replaces a portion of the targeted locus can be, for example, approximately 0.5-5 kilobases (e.g., 1-4 or 3-4 kilobases). A specific example of such a construct is described below, in the experimental examples.

The targeting constructs can be included within any appropriate vectors, such as plasmid or viral vectors (e.g., adenovirus or adeno-associated virus vectors), which can be introduced into cells using standard methods including, for example, viral transduction, electroporation, or microinjection. One example employs an adeno-associated viral vector (AAV) (e.g., rAAV2, which can be made by standard methods using a pAV2 plasmid (ATCC 37216), rAAV1, and rAAV5).

The use of AAV to deliver the targeting construct offers many benefits. First, AAV1 (and other AAV serotypes) infects pig fetal fibroblasts with 95-100% efficiency. Second, AAV infection of pig fetal fibroblasts results in little or no cell toxicity. Third, AAV infection results in the delivery of a single-stranded gene targeting construct directly to the nucleus. Single-stranded gene targeting vectors are thought to yield more efficient gene targeting and result in a more favorable homologous recombination to non-homologous recombination ratio (Hendrie and Russell, Molecular Therapy 12(1):9-17, 2005).

The methods of the invention, employing AAV vectors, resulted in high levels of gene targeting efficiency in these somatic cells, as compared to prior methods. Central to the methods of the invention is the fact that the entire procedure was performed in a time-sensitive manner, because excessive cell culture time (more than 30 days) negatively impacts nuclear transfer efficiency (Lai et al., Cloning and Stem Cells 5(4):233-241, 2003). In one example, following fibroblast harvest from day 35 fetuses, the fetal fibroblast cells were frozen within 48 hours. The use of an AAV vector to deliver the gene targeting construct allowed targeting to begin 24 hours after thawing cells and required no cell detachment and re-attachment, which is required in other methods. Multiple cell detachment and re-attachment events (trypsinization) are thought to decrease the ability of a cell to serve as a nuclear donor in nuclear transfer. Further, G418 selection in 48 96-well plates prevents the need for the more conventional, time-consuming isolation of resistant clones with cloning rings. The screen for gene-targeted clones was designed such that all positive clones could be identified and frozen within a 3-5 day period. All clones were frozen by day 18, therefore the cells have been in culture approximately 20 days since being harvested from the fetus. This is an important aspect of the invention, because reduction of the time in culture increases the likelihood that cells used as nuclear donors are viable, normal, and euploid.

Accordingly, the invention provides a method of gene-targeting cells, such as pig cells (e.g., pig fetal fibroblasts), in which the number of days in culture (during which targeting and selection takes place) is less than 30 days, e.g., 25-29, 20-24, 19, 18, 17, 16, 15, or fewer days. To facilitate this method, the selection can take place in multi-well plates, as described further below. Further, the cells may be frozen shortly after harvest (e.g., within 24, 48, or 96 hours). After cell thawing (or after harvest, if the cells are not previously frozen), gene targeting with an AAV vector can be carried out within, for example, 12, 24, 36, or 48 hours, without the use of multiple detachment/re-attachment events, and selection can proceed in an expedited manner, such as by use of multi-well plates (e.g., 96-well plates), prior to freezing.

Other types of vectors, or more specifically other types of targeting construct delivery methods, are available, and were used during initial attempts to disrupt the pig CFTR gene. Cell transfection methods, including calcium phosphate, lipofection, electroporation, and nuclear injection can be used to deliver the targeting construct, though the disadvantages of inefficient transfection efficiency, cell toxicity, requirement of a pure (clean) targeting construct DNA sample, and poor ratio of homologous recombination to non-homologous recombination far outweigh the benefit of ease. If the gene is transcriptionally active in the cell being used, then a promoterless selectable marker strategy can be employed, so that antibiotic resistance will only be found in cell that have had a recombination event within a transcribed unit.

Genetically targeted cells are typically identified using a selectable marker, such as neomycin. If a cell already contains a selectable marker, however, a new targeting construct containing a different selectable marker can be used. Alternatively, if the same selectable marker is employed, cells can be selected in the second targeting round by raising the drug concentration (for example, by doubling the drug concentration), as is known in the art. As is noted above, targeting constructs can include selectable markers flanked by sites facilitating excision of the marker sequences. In one example, constructs can include loxP sites to facilitate the efficient deletion of the marker using the cre/lox system. Use of such systems is well known in the art, and a specific example of use of this system is provided below, in the experimental examples.

Upon obtaining cells in which a target gene (e.g., a CFTR gene) has been targeted (one or both alleles, as described above), nuclear transfer can be carried out. Optionally, the genetically modified nuclear donor cells can be frozen prior to nuclear transfer. Recipient cells that can be used in the invention are typically oocytes, fertilized zygotes, or two-cell embryos, all of which may or may not have been enucleated. Typically, the donor and the recipient cells are derived from the same species. However, it is possible to obtain development from embryos reconstructed using donor and recipient cells from different species.

Recipient oocytes can be obtained using methods that are known in the art or can be purchased from commercial sources (e.g., BoMed Inc., Madison, Wis.). As is known in the art, the donor nucleus or the donor cell itself can be injected into the recipient cell or injected into the perivitelline space, adjacent to the oocyte membrane. The nuclear transfer complex formed in this manner can be activated by standard methods, which may involve electrical fusion/activation or electrical fusion/chemical activation, as is described further below. Further processing of the nuclear transfer complex, including implantation of the complexes into surrogate mothers, is described further below.

The transgenic animals of the invention can be used in the identification and characterization of drug and other treatment methods for the disease or condition associated with mutation of the gene targeted according to the invention. In these methods, for example, a candidate therapeutic agent can be administered to an animal and the impact of the agent on a feature of the disease exhibited by the animal can be monitored. Optionally, the methods can also involve exposure of the animals to environmental or other conditions known to contribute to or exacerbate the disease or condition. For example, in the case of CF animal models having impaired respiratory function, the effect of the drug on such function can be assessed by measurement of standard respiratory parameters. In another example, in the case of animals exhibiting impaired digestion, due to blockage of pancreatic and/or liver ducts, the effect of a treatment on digestion can be determined.

With the porcine model of the invention, it is possible to test hypotheses that lead to new treatments and to evaluate potential therapies for CF lung disease. The porcine model also makes it possible to assess electrolyte transport by porcine airway epithelia in vitro and in vivo, the volume of airway surface liquid in vitro and in vivo, the ion composition of airway surface liquid in vitro and in vivo, the airway surface liquid pH in the airway, and electrolyte transport in the small airways. It is also possible to measure respiratory mucociliary transport in vitro and in vivo. For assessing inflammation, several tests and assays can be carried out, including (but not limited to) assays of key markers of inflammation in amniotic fluid, fetal lung liquid, and bronchoalveolar lavage by using lung tissue histochemistry, large-scale gene expression profiling of pulmonary tissues, cytokine and cell assays, and proteomics. It is also possible to raise CF and non-CF piglets in isolators under completely germ free conditions and to test for the development of pulmonary inflammation, and then selectively expose the piglets to inflammatory stimuli including bacteria and viruses. In addition, investigators can test how loss of CFTR function in airway epithelia results in altered NFKB signaling, the function of secreted epithelial antimicrobials/host defense proteins, and the consequences of loss of CFTR function in macrophages or neutrophils. The availability of the porcine CF model allows tests of the early manifestations of the CF, an important question that remains unanswered. The natural history of pulmonary infections in CF pigs can also be monitored, leading to a determination of whether the airway epithelia of CF pigs can be colonized by CF or porcine pathogens and/or non-pathogenic opportunistic organisms.

Although lung disease is the current main cause of mortality, patients suffer from CF disease in many other organs. Availability of a CF model allows new investigations and tests of therapeutics in the pancreas, intestine, sweat gland, liver, vas deferens, kidney, and other organs affected primarily or secondarily by CF. The screening methods of the invention can be carried out to test the efficacy of new compounds, combinations of new and old compounds, non-pharmaceutical treatments, and combinations of pharmaceutical and non-pharmaceutical treatments.

The invention has been described above in reference to mutation of the CFTR gene to generate non-human animal models of cystic fibrosis. As is stated above, the invention can also be used in the generation of transgenic, non-human animal models of other diseases and conditions associated with gene mutations. There are innumerable examples of such diseases and conditions known in the art, which can be included in this invention. Some specific examples are listed in the Table 1.

TABLE 1

| Disease | Gene | Reference |
|---|---|---|
| Hypercholesterolemia and atherosclerosis | LDLR and APOE | Lusis et al., Annu. Rev. Genomics Hum. Genet. 5: 189-218, 2004 |
| Cancer | p53, BRCA1 and 2 | Levine-AJ, Cell, 88: 323-331, 1997 Gudmundsdottir and Ashworth, Oncogene. 25(43): 5864-5874, 2006 |
| Huntington's disease | huntingtin | Walker, Lancet 369(9557): 218-28, 2007 |
| Duchenne muscular dystrophy | dystrophin | Deconinck and Dan. Pediatr Neurol. (1): 1-7, 2007 |
| Polycystic kidney disease | PKD1 and 2 | Gattone V., Current Opinion in Pharmacology 5: 535-542, 2005 |
| Sickle-cell disease | alpha/beta-globin | Steinberg MH, Trends Pharmacol. Sci. 27(4): 204-10, 2006 |
| Hemophilia A | Factor VIII | Bolton-Maggs and Pasi, Lancet 24; 361(9371): 1801-9, 2003 |
| Ataxia-telangiectasia | ATM | Concannon and Gatti, Hum. Mutat. 10(2): 100-7, 1997 |
| Retinoblastoma | RB1 | Lohmann, Hum. Mutat. 14(4): 283-8, 1999 |

Possible mutations to these disease genes include knock-outs (by, e.g., insertion of a selection cassette), knock-ins (e.g., by point mutations that correspond to human disease mutations), and, in the case of Huntington's disease (and any other trinucleotide repeat expansion disorder family members), an expansion of the trinucleotide repeat to pathogenic sizes.

The following Examples are meant to illustrate the invention and are not meant to limit the scope of the invention in any way.

EXPERIMENTAL EXAMPLES

We wished to generate pigs with two different alterations in their CFTR gene, a null allele and the ΔF508 mutation. A null allele would lack any CFTR function; it should therefore provide a valuable model for assessing the porcine CF phenotype, for comparing the consequences of other CF-associated mutations, for exploring pathogenesis, and for evaluating many therapeutic strategies. The ΔF508 mutation deletes Phe508 and is the most common CF-associated mutation, accounting for ~70% of CF alleles (Zielenski et al., Annu. Rev. Genet. 29:777-807, 1995). In humans, this mutation disrupts processing of the protein, so that nearly all CFTR- ΔF508 is retained in the endoplasmic reticulum (ER) and degraded, preventing maturation to the plasma membrane. In addition, this deletion reduces the activity of single CFTR channels and shortens their lifetime on the cell surface (Dalemans et al., Nature 354:526-528, 1991; Teem et al., Receptors Channels 4:63-72, 1996; Skach, Kidney Int. 57:825-831, 2000). Earlier work showed that reducing the incubation temperature and other interventions allowed some of the mutant protein to escape the ER and traffic to the cell surface, where it retained significant activity (Denning et al., Nature 358: 761-764, 1992). These findings plus the prevalence of the ΔF508 mutation have driven efforts to correct the CFTR-ΔF508 defects (Lukacs et al., N. Engl. J. Med. 349:1401-1404, 2003; Verkman et al., Curr. Pharm. Des. 12:2235-2247, 2006). We have found that porcine CFTR-ΔF508 showed at least partial processing in vitro (Ostedgaard et al., Proc. Natl. Acad. Sci. U.S.A. 104:15370-15375, 2007; also see below). A pig with the ΔF508 mutation could be of value for understanding the mechanisms responsible for the CFTR-ΔF508 biosynthetic defects in vivo and for developing pharmacological agents to correct the CFTR-ΔF508 biosynthetic defects. To begin developing these porcine models of CF, we combined gene targeting and SCNT.

The following experimental examples describe the generation of cystic fibrosis pig models (CFTR-null and CFTR-ΔF508 alleles), an interspecies analysis of the ΔF508 mutation, and approaches to making pigs expressing human CFTR sequences (e.g., human ΔF508 CFTR).

I. Cystic Fibrosis Pig

Results

Fetal Pig Fibroblasts Express Little CFTR

Figure 1:
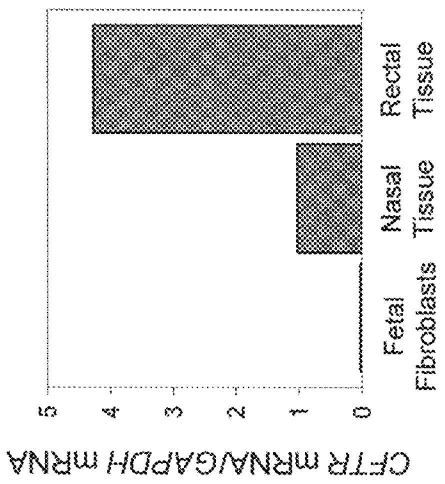
FIG. 1 is a graph showing CFTR expression in pig fetal fibroblasts. Data are quantitative RT-PCR of pig CFTR mRNA relative to GAPDH in primary pig fetal fibroblasts, nasal epithelia, and rectal epithelia. Similar results were obtained on two other occasions.

We worked with fetal fibroblasts from domestic pigs (*Sus scrofa*) since they have been used successfully for transgenic SCNT (Park et al., Animal Biotechnology 12(2):173-181, 2001). Because a promoter-trap strategy was previously used in porcine fibroblasts (Lai et al., Science 295:1089-1092, 2002), we asked if CFTR is expressed in fetal fibroblasts. We used quantitative RT-PCR and compared the results to transcript levels in nasal and rectal epithelia, which are known to express CFTR at low levels (Trapnell et al., Proc. Natl. Acad. Sci. U.S.A. 88:6565-6569, 1991). FIG. 1 shows that the primary fibroblasts produced very little CFTR mRNA. This result prevented the use of a promoter-trap strategy as was done for the only other gene targeted in pigs (Lai et al., Science 295:1089-1092, 2002; Dai et al., Nat. Biotechnol. 20:251-255, 2002).

Developing Vectors to Target the Pig CFTR Gene

Figure 2:
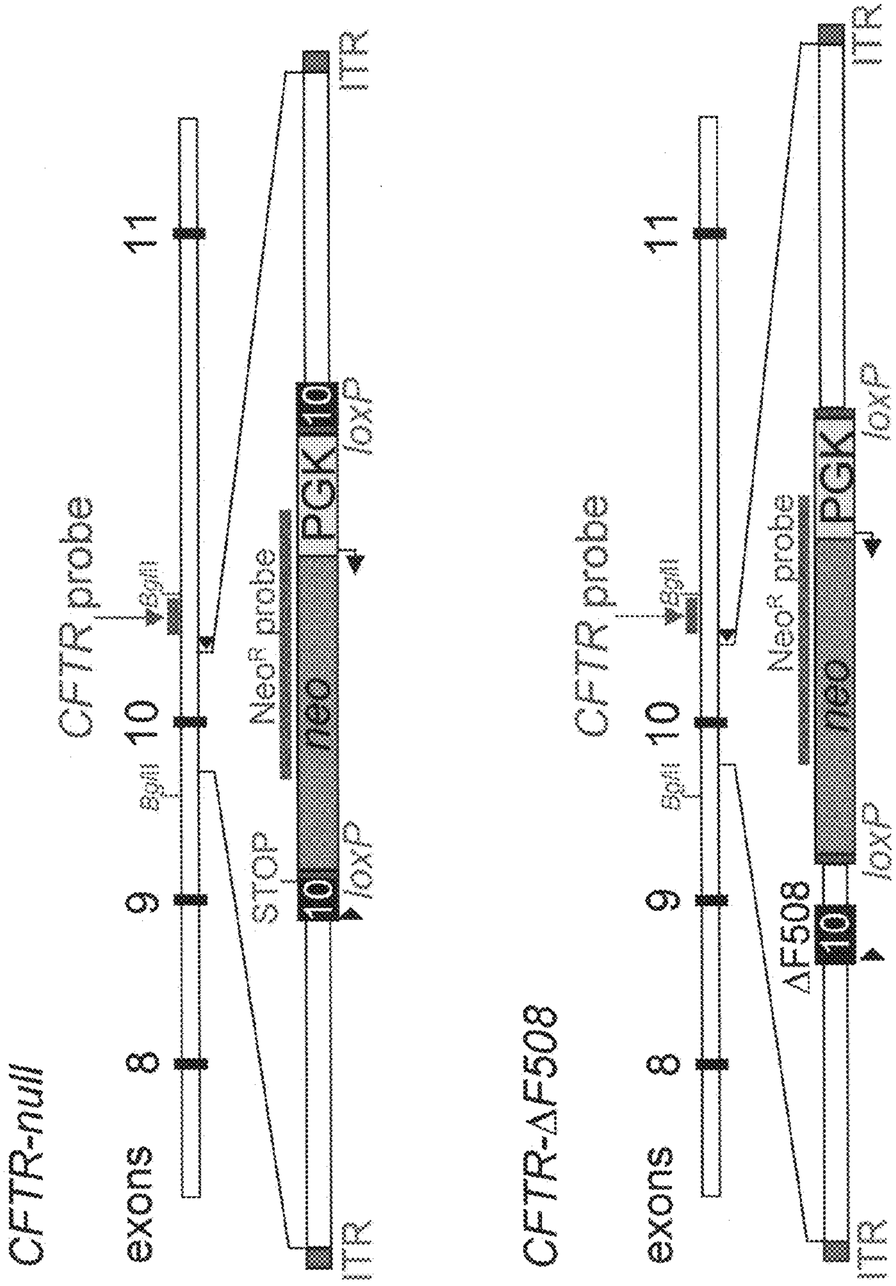
FIG. 2 is a schematic representation of targeting constructs for homologous recombination for CFTR-null and CFTR-ΔF508. Exons 8-11 of pig CFTR are depicted in black boxes. $Neo^R$ contains a neomycin resistance cDNA driven by the PGK promoter and flanked by loxP sites. The engineered stop codon is indicated in the CFTR-null targeting vector. The positions of probes for $Neo^R$ and CFTR Southern blots are indicated. PCR screen primers are depicted as arrowheads.

We designed a "null" targeting construct to disrupt CFTR exon 10 with a neomycin resistance cassette ($Neo^R$) (FIG. 2). Because CFTR can exhibit some alternative splicing, we chose to disrupt exon 10, which encodes a portion of nucleotide binding domain 1; this exon is required for CFTR function. We also included an engineered stop codon at position 508. Therefore, F508X would be expected to trigger nonsense-mediated mRNA decay as well as prematurely interrupt any translation of CFTR. The ΔF508 targeting vector was designed to delete residue Phe508 (FIG. 2). We also inserted a $Neo^R$ in the intron downstream of exon 10 as a positive selection marker. In this vector, $Neo^R$ was flanked by loxP sites so that it could be removed at a later time if it was found to markedly reduce the level of the CFTR-ΔF508 mRNA, a situation encountered in some attempts to make a CFTR-ΔF508 mouse (Colledge et al., Nat. Genet. 10:445-452, 1995; Zeiher et al., J. Clin. Invest. 96:2051-5064, 1995).

We initially used nuclear microinjection and then electroporation to deliver the null targeting vector to fetal fibro blasts. However, we recovered no clones with homologous recombination. We then investigated AAV-mediated gene targeting, which has been used to deliver targeting vectors to cell lines and primary cells (Inoue et al., J. Virol. 73:7376-7380, 1999; Hirata et al., Nat. Biotechnol. 20:735-738, 2002; Porteus et al., Mol. Cell. Biol. 23:3558-3565, 2003; Russell et al., Nat. Genet. 18:325-330, 1998). Using an AAV vector has the advantage that it delivers single-stranded DNA to the nucleus, the amount of DNA per cell is small, and it can infect many cell types (Hendrie et al., Mol. Ther. 12:9-17, 2005). To first determine which AAV serotypes can infect pig fetal fibroblasts, we infected them with eGFP-expressing AAV1, 2, and 5 (each with AAV2 ITRs). Each AAV infected the cells with at least 50-80% efficiency, however, AAV1 appeared to infect nearly 100% of cells. Because of rAAV genome size constraints, the total length of the targeting vectors was limited to 4.5 kb. $Neo^R$ was centrally located in both vectors (FIG. 2).

AAV Vectors Introduced the CFTR-Null and CFTR-ΔF508 Alleles

We obtained fetal fibroblasts from males so that all of our clones would be male, which would allow us to more rapidly expand the number of animals. Primary cultures of pig fetal fibroblasts were infected with AAV1 carrying the null targeting vector. After 24 hours, cells were transferred to a series of 96-well plates. Approximately two weeks later, cells in each well of the 96-well plates were "replicated" by splitting among three plates: 96-well culture plates for cell expansion, 96-well culture plates for potential cryopreservation, and 96-well PCR plates for cell lysis.

Figure 3:
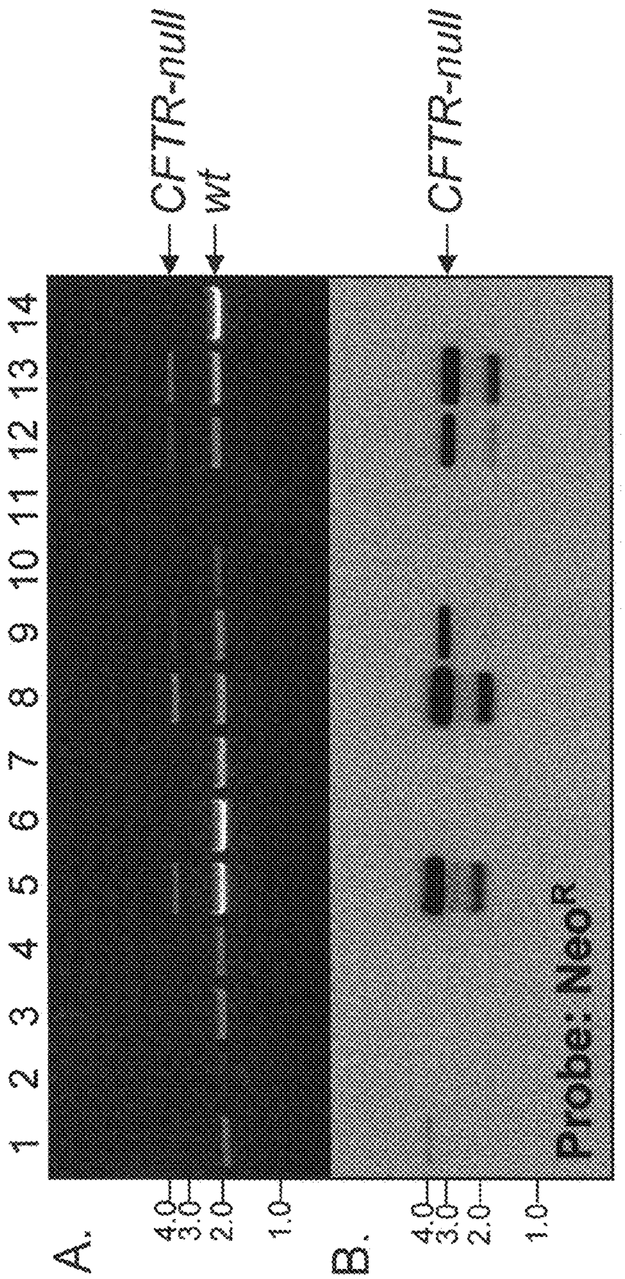
FIG. 3 shows screening results from CFTR-null targeted pig fetal fibroblasts. A) Example of PCR results. Primers amplified a 2.0 kb product from the wild-type allele and 3.7 kb product from the CFTR-null allele. Lanes 5, 8, 9, 12, and 13 are examples of PCR-positive clones. B) Southern blot of the PCR gel using a $Neo^R$-specific biotin-labeled oligonucleotide. This assay confirms that the 3.7 kb product contains the $Neo^R$ sequence. The weaker hybridization signal at 2.0 kb appears to be an artifact, with some of the targeted band co-migrating with the wild-type product. Note the differences in intensity of the two bands in panel A relative to panel B.

We screened cell lysates by PCR to identify wells containing gene-targeted clones (FIG. 3A) and then hybridized with a $Neo^R$-specific probe to test for inclusion of this marker (FIG. 3B). We then froze positive clones; by that time, cells had been in culture 15-17 days. We also passaged positive clones from the "cell expansion" plates to generate DNA for genotype determination. Southern blots with CFTR- and $Neo^R$ specific probes identified clones with a targeted CFTR allele that were free of random integration (FIG. 4). On average, 75% of PCR-positive clones were also positive by Southern blot and were clonal.

We used identical procedures to introduce the CFTR-ΔF508 construct and screen for homologous recombinants. We identified numerous PCR-positive clones (FIG. 5A), that were confirmed by Southern blotting with a ΔF508 allele-specific probe (FIG. 5B). Eighteen of 25 (72%) PCR-positive clones contained the F508 deletion. The other 28% failed to contain ΔF508, suggesting that gene targeting had occurred, but crossing over was downstream of F508. Subsequent Southern blots revealed CFTR-ΔF508 targeted clones (FIGS. 6A and 6B).

Variability in Homologous Recombination Depended on the Donor

Over the course of these studies, we targeted the CFTR gene in fibroblasts derived from several fetuses. The fetuses were all siblings harvested from the same uterus at the same time. Yet, surprisingly, we saw a striking fetus-to-fetus variability in targeting frequency (Table 2, below). Even when fibroblasts from different fetuses were infected and screened at the same time, with the same reagents, and by the same people, pronounced differences occurred; an example is fetus 5 vs. fetus 7 in Table 2. These results suggest the difference was not due to experimental process.

TABLE 2

| Donor | G418-resistant (%) | Targeted/G418-resistant (%) |
|---|---|---|
| 9 | 0.13 | 0.03 |
| 5 | 0.09 | 10.93 |
| 7 | 0.09 | 0.07 |
| 2 | 0.17 | 7.29 |
| 3 | 0.18 | 7.22 |
| 4 | 0.15 | 0.027 |

CFTR targeting data from donor cells derived from multiple fetuses. "Donor" refers to the number of the donor for the fibroblasts. The percentage of G418-resistant cells was determined by dividing the number of G418-resistant clones by the number of AAV-infected cells * 100. Targeted clones are those that were PCR-positive for homologous recombination.

SCNT Produced Gene-Targeted Piglets

To produce heterozygote pigs, we used the CFTR-null targeted fetal fibroblasts as nuclear donors for transfer to enucleated oocytes. Then to each of eight surrogate females, we transferred between 94 and 144 SCNT embryos. At 117-118 days of gestation (full term), we delivered piglets by Cesarean section. Five surrogates produced ten males; three surrogates did not produce offspring. FIG. 7 shows the first CFTR+/− piglet. Southern blots revealed that nine of the ten offspring were CFTR-null heterozygotes, and one was wild-type (FIG. 8). The CFTR+/− males reached sexual maturity, and they sired numerous litters of heterozygote offspring, both males and females.

In addition, each of four surrogates received 103-185 CFTR-ΔF508 SCNT embryos. Five males were recovered from three surrogates on days 116-117. Southern blots revealed that four were CFTR-ΔF508 heterozygotes and one was a wild-type. The CFTR-ΔF508 males have not yet reached sexual maturity. All of the CFTR+/− and CFTR+/ΔF508 were phenotypically normal.

The ΔF508 Allele, but not the Null Allele, Generated mRNA

We asked whether the targeted alleles were transcriptionally active in an epithelium where CFTR is normally expressed. We biopsied rectal epithelia and measured CFTR mRNA using quantitative RT-PCR. In CFTR+/− animals, mRNA was present at ~50% of wild-type levels (FIG. 9A). We cannot be certain that the remaining mRNA arose from the non-targeted allele, however the result is consistent with disruption of one CFTR allele and nonsense-mediated mRNA decay.

To assess the influence of the $Neo^R$ cassette that resides in the intron downstream of exon 10, we used probes specific for wild-type CFTR and CFTR-ΔF508. CFTR-ΔF508 mRNA was present at 65-70% of wild-type levels (FIG. 9B). This expression level suggests that the retained $Neo^R$ cassette has only minimal effects on transcription. Moreover, this amount of transcript is likely sufficient to produce relatively normal amounts of CFTR-ΔF508 protein.

Mating of CFTR+/− Males and CFTR+/− Females

The CFTR+/− males and CFTR+/− females reached sexual maturity and were mated. To date, the sows have delivered two litters with a total of 16 piglets.

FIG. 10 shows some of the piglets at one day of age. The piglets were active and could not be distinguished by appearance or behavior, a situation that is similar to humans with cystic fibrosis (CF), who appear identical at birth to those without CF.

Genotyping by PCR showed that the two litters had 8 CFTR+/+, 3 CFTR+/−, and 5 CFTR−/− piglets (FIG. 11).

We assessed electrolyte transport in wild-type and CFTR−/− piglet airway epithelia by measuring the transepithelial voltage (Vt) across nasal epithelia; we used methods identical to those used in humans (FIG. 12). As expected, amiloride inhibited Vt in both sets of piglets indicating the presence of ENaC $Na^+$ channels. To test for the presence of CFTR $Cl^-$ channels, we reduced the $Cl^-$ concentration on the apical surface. The wild-type Vt hyperpolarized as observed in non-CF humans. However, in the CFTR−/− piglets, Vt did not change, a finding identical to the result in CF humans. This result indicates that CFTR function is absent in the CF piglets. Adding isoproterenol, to increase intracellular levels of cAMP, failed to hyperpolarize Vt, and application of ATP, to increase the intracellular $Ca^{2+}$ concentration, had only small effects on Vt in animals of both genotypes. These results indicate that the CFTR−/− piglets do not have a prominent alternative $Cl^-$ channel. In contrast, CFTR−/− mice have a markedly increased alternative $Cl^-$ channel that has been hypothesized to explain the fact that CF mice do not develop lung disease. Finally, addition of the CFTR inhibitor GlyH-101 inhibited Vt in non-CF, but not CF piglets. Together, these data indicate that CFTR is absent from the nasal epithelia in CFTR−/− piglets. Importantly, the CF piglets show electrolyte transport similar to that in humans with CF and different from that in CF mice.

On gross inspection, the pancreas from the CFTR−/− piglets was smaller, showed less distinct lobulation, and was redder than that from a CFTR+/+ piglet (FIG. 13). Of note, humans with severe CFTR mutations uniformly develop pancreatic insufficiency, whereas CFTR−/− mice do not develop pancreatic disease.

The CFTR−/− piglets developed meconium ileus, which occurs in 15% of humans with CF. In humans, meconium ileus is associated with severe mutations in the CFTR gene. Of note, meconium ileus does not occur in CFTR−/− mice.

For unknown reasons, CF mice, but not CF humans, have white teeth. The color of the teeth in CFTR+/+ and CFTR−/− piglets was identical, indicating that in this respect, the CF pigs are like humans rather than mice.

These results indicate that CF pigs have a phenotype like that in humans with CF, including electrolyte transport in airway epithelia, pancreatic disease, meconium ileus, and tooth color. Importantly, in each of these cases, they are different from CF mice. These data suggest that CFTR−/− pigs will serve as an ideal model in which to study the pathogenesis of CF and to develop new treatments, as described herein.

Materials of Methods

Fetal Fibroblasts

Fetal fibroblasts were isolated from day 35 fetuses as previously described (Lai et al., Cloning Stem Cells 5:233-241, 2003). Cells were grown at 39° C. in F10 media (Invitrogen) containing 20% FCS and 30 μg/ml gentamicin. Fetus gender was determined by PCR amplification of the Y-chromosome-specific Sry gene (Pomp et al., J. Anim. Sci. 73:1408-1415, 1995).

Targeting Vector Construction

Genomic clone: Genomic DNA was isolated (Puregene, Gentra) from pig fetal fibroblasts. A 5683 bp PCR product including CFTR exon 10 and flanking intronic sequence was amplified from pig fetal fibroblast genomic DNA using primers GC1F and GC8R (for primer sequences see Table 3, below) and a high fidelity polymerase (PfuUltra, Stratagene). Primers were designed based on the domestic pig genomic sequence from the NIH Intramural Sequencing Center (NISC) Comparative Vertebrate Sequencing Project (Genbank: AC092478 and AC092497). This PCR product was subcloned into pCR-Blunt II-TOPO (Invitrogen), verified by sequencing (using primers GC1F-GC8R), and served as the template for PCR amplification of 5' and 3' targeting arms. This plasmid is referred to as pG16.

CFTR-KO construction: Using PCR, the 5' and 3' homologous recombination arms were amplified from pG16 and sequentially subcloned upstream and downstream of the $Neo^R$ cassette in pPGK-Neo-I (a generous gift from Tim Ley, Washington University; Genbank Accession Number AF335419) such that the $Neo^R$ cassette is in the opposite orientation to the CFTR sequence. Primers: 5' arm: G16-Neo5'F and G16-Neo5'R; 3' arm: G16-Neo3'F and G16-Neo3'$^R$. The $Neo^R$ cassette consists of a $Neo^R$ cDNA driven by the PGK promoter and is flanked by loxP sites. In the resulting construct, the $Neo^R$ cassette disrupts CFTR exon 10 immediately after an in-frame stop codon that was introduced to follow isoleucine 507. Thymidine 1531 is effectively deleted, becoming the first nucleotide of the stop codon. This targeting construct is referred to as pG16-Neo.

CFTR-ΔF508 construction: The CFTR-ΔF508 targeting vector was constructed in a similar way using the following primers: 5' arm: dF-Neo 5'F-XhoI and dF-Neo 5'R-EcoRV; 3' arm: dF-Neo 3'F-BamHI and dF-Neo 3'R-HindIII. The nucleotides encoding F508 were subsequently deleted from exon 10 using PCR mutagenesis. This targeting construct is referred to as pdF-Neo.

TABLE 3

Primers

| Name | Sequence (5'-3') |
|---|---|
| GC1F | TTTCTCTTCTGCCTATTTCCC (SEQ ID NO: 7) |
| GC1R | AGAAAACACTGAAGGATGCCT (SEQ ID NO: 8) |
| GC2F | GTTTCAAATAGTTACTCAGTTTGA (SEQ ID NO: 9) |
| GC2R | CCTCCAACTGACACTAATCTTCTCA (SEQ ID NO: 10) |
| GC3F | GTAGAGCTGTCAGAGAAGTAA (SEQ ID NO: 11) |
| GC3R | AAGCCACAGAAGCATATGCAT (SEQ ID NO: 12) |
| GC4F | AATCACTCTCAGGATGCACAT (SEQ ID NO: 13) |
| GC5F | ATACTCAGAACAGGAAGTGCT (SEQ ID NO: 14) |
| GC5R | ATAGCATAAGCTTCACTGTGC (SEQ ID NO: 15) |
| GC6F | TGTCAGTAGAGAATTAGAGATTA (SEQ ID NO: 16) |
| GC6R | GCACTACTCACCTACATCCA (SEQ ID NO: 17) |
| GC7F | ACCTGGAAGTTGGAACACTCA (SEQ ID NO: 18) |
| GC7R | GAAGACCCTTTACCTTCTTCTA (SEQ ID NO: 19) |
| GC8F | CATCCAGCTGCAAACAACATT (SEQ ID NO: 20) |
| GC8R | AATTATGCCAAACTCCATCTTAT (SEQ ID NO: 21) |
| Ex10a5F | AGAATTTCATTCTGCTCTCAGT (SEQ ID NO: 22) |

Quantitative RT-PCR primers and probes
Pig CFTR and GAPDH expression in fetal fibroblasts, nasal and rectal tissue (FIG. 1) and CFTR expression in CFTR +/− pigs (FIG. 9A).

| CFTR primers and probe | |
|---|---|
| pCFTR-1819F (anneals within exon 18) | AGTGGGCTGTAAACTCCAGTATAGA (SEQ ID NO: 23) |
| pCFTR-1819R (anneals withinin exon 19) | CCTTCTGCCGGCATATCAATAAACT (SEQ ID NO: 24) |
| pCFTR-1819 probe (spans exon 18/19 junction) | FAM-ATCGCATCAAGCTATCC-NFQ (SEQ ID NO: 25) |
| **GAPDH primers and probe** | |
| pGAPDH-TM-F | AAGCTCATTTCCTCGTACGACAAT (SEQ ID NO: 26) |
| pGAPDH-TM-R | GGAGGCCATGTGGACCAT (SEQ ID NO: 27) |
| pGAPDH-TM probe | FAM-TCCACCACCCTGTTGCT-NFQ (SEQ ID NO: 28) |

TABLE 3-continued

| Primers | |
|---|---|
| Name | Sequence (5'-3') |
| Pig CFTR and ΔF508-CFTR expression in CFTR +/ΔF508 pigs (FIG. 9B). Primers are the same for both, probes are allele specific. | |
| CFTR primers and probe | |
| pCFTR-TM-F | TCATGCCGGGCACCATTAAA (SEQ ID NO: 29) |
| pCFTR-TM-R | CGCTTTGATGACACTCCTGTATCTA (SEQ ID NO: 30) |
| pCFTR-TM probe | FAM-ACACCAAAGATGATGTTTTC-NFQ (SEQ ID NO: 31) |
| ΔF508 primers and probe | |
| delF-TM-Forward | TCATGCCGGGCACCATTAAA (SEQ ID NO: 32) |
| delF-TM-Reverse | CGCTTTGATGACACTCCTGTATCTA (SEQ ID NO: 33) |
| delF-TM-Probe | FAM-GAAACACCAATGATGTTTTC-NFQ (SEQ ID NO: 34) |

PCR Primers and Probes. All DNA sequences are 5'-3'.
FAM: 6-carboxyfluorescein;
NFQ: Non Fluorescent Quencher AAV Production The targeting vector sequences were amplified from pG16-Neo and pdF-Neo by PCR to include flanking SbfI sites and were subcloned into the rAAV2 proviral plasmid, pAV2 (ATCC 37216). Because of AAV genome size constraints, the total length of the targeting vectors is ~4.5 kb with the NeoR cassettes centrally located (G16-Neo: 5' targeting arm=1510 bp; 3' targeting arm=1274 bp; NeoR cassette=1706 bp. dF-Neo: 5' targeting arm=1475 bp; 3' targeting arm=1296 bp; NeoR cassette=1706 bp). pAV2-G16-Neo was grown in SURE2 cells (Stratagene) and purified via a $CsCl_2$ method (Sambrook, Fritz, and Maniatis, Molecular Cloning: A Laboratory Manual, $2^{nd}$ edition, Cold Spring Harbor Laboratory Press, Plainview, N.Y., 1989). rAAV1 (with AAV2 ITRs) was prepared as previously described (Yan et al., J. Virol. 76:2043-2053, 2002). Helper-free virus stocks were treated with nuclease and purified by high-performance liquid chromatography. Physical titers of rAAV were determined by slot blot hybridization. These viruses are referred to as AAV-G16-Neo and AAV-dF-Neo.

Infection and Selection $1.5\times10^6$ fetal fibroblasts were thawed and plated on a 100 mm collagen-coated culture dish. 24 hours later, cells were infected with AAV-G16-Neo or AAV-dF-Neo (200 µl, $2.5\times10^{12}$ particles/ml). 24 hours later, cells were trypsinized and transferred to 48 96-well, collagen-coated plates (BD Biosciences). 48 hours later, G418 (100 µg/ml) was added to the cell media. 10 days later, each well was trypsinized (60 µl trypsin, 0.5% EDTA) and split among 3 different vessels. For cell freezing, ⅓ of the cells were transferred to 96-well collagen-coated culture dishes and returned to the incubator for growth. For cell propagation, ⅓ of the cells were transferred to 96-well collagen-coated culture dishes and returned to the incubator for growth. For PCR screening, ⅓ of the cells were transferred to 96-well PCR plates.

PCR Screen and PCR Southern Blot

Cells in the 96-well PCR plates were spun down and resuspended in lysis buffer (50 mM KCl, 1.5 mM $MgCl_2$, 10 mM Tris-Cl, pH 8.5, 0.5% Nonidet P40, 0.5% Tween, 400 µg/ml Proteinase K) (McCreath et al., Nature 405:1066-1069, 2000). Most wells (~70%) contained only dead cell debris following selection, but all wells were processed to minimize human error. The cells were lysed for 30 min at 65° C., followed by 10 min at 95° C. 1 µl of lysate was used in a 50 µl PCR reaction. PCR conditions: 2 min at 95° C., 30 cycles of 95° C. for 20 sec, 56° C. for 20 sec, and 68° C. for 4 min, then 68° C. for 5 min. Primers Ex10a5F and GC7R are expected to amplify a 2.0 kb product from wild-type alleles and a 3.7 kb product from G16-Neo targeted alleles. PCR products were electrophoresed on 1.0% E-Gel 96 gels (Invitrogen). Positive PCR reactions were also electrophoresed on standard 1.0% agarose gels and transferred to a nylon membrane. The membranes were probed with biotin-labeled Neo-specific or ΔF508-allele-specific oligonucleotides and detected by chemiluminescence (North2South, Pierce).

Processing Screen-Positive Cells

Following identification of PCR-positive clones, the corresponding cells from the "freezing" plate were grown to confluence (~10,000 cells). Cells were detached with 60 µl trypsin and 20 µl of detached cells were placed into each of 3 cryovials. Three hundred µl freezing media was added to each cryovial and the vials were transferred to an isopropanol cryofreezing container at −70° C. After 24 hours, the vials were transferred to liquid nitrogen. The corresponding cells from the propagation plate were transferred to 24-well plates, and subsequently to 6-well and 100 mm culture dishes. The sequential transfer to increasingly larger culture dishes was carried out to achieve consistent cell growth and viability.

Southern Blotting

For CFTR-KO targeting, genomic DNA was isolated from 100 mm dishes (Gentra) and 10 µg was digested with BglII overnight. For CFTR-ΔF508 targeting, genomic DNA was isolated from 24-well dishes. Ten ng was used for whole genome amplification (Repli-G, Qiagen) and 25 µg amplified DNA was digested with BglII overnight. Genomic digests were electrophoresed on a 0.7% agarose gel and transferred to a positively charged nylon membrane (Roche) by using an alkaline transfer procedure. Blots were pre-hybridized for 15 min at 65° C. in Rapid-hyb buffer (Amersham). The blot was then hybridized in Rapid-hyb buffer with a $^{32}P$-labeled probe specific for a region of CFTR that is outside of the targeting vector boundaries. For Neo-specific probing, blots were either stripped, or, in most cases, the BglII digest and Southern blot procedure was repeated using a $^{32}P$-labeled Neo-specific probe.

Preparation of Donor Cells for SCNT

Frozen aliquots of CFTR-targeted cells were thawed at 37° C. and pre-warmed in F-10 medium (Invitrogen) with 20% fetal calf serum (FCS). The cells were washed twice by centrifugation and cultured (F-10, Invitrogen; 20% FCS, Hyclone; gentamicin, 2.5 ng/ml FGF and G418, Invitrogen) for 1-2 days in 24-well collagen-coated plates (35-4408, Biocoat cellware). Confluent cells were dispersed with 0.05% trypsin/EDTA for 3-5 min at 38.5° C. and 500 μL F-10 with 20% FBS, followed by centrifugation twice at 3000 rpm for 5 min. The supernatant was removed, and the cells were resuspended in micromanipulation medium (25 mM HEPES, TCM199, Gibco; 0.3% BSA).

Oocyte Maturation and SCNT

Oocytes were received from BoMed, Inc (Madison, Wis.) ~24 hours after placing them into maturation medium, and were then transferred to a 4-well dish and cultured for a total maturation of 42-44 hours at 38.5° C. in a humidified atmosphere of 5% $CO_2$ in air. After 42-44 h of in vitro maturation, oocytes were stripped of their cumulus cells by gentle vortexing in 0.5 mg/mL hyaluronidase. After removal of the cumulus cells, oocytes with good morphology and a visible polar body (metaphase II) were selected and kept in micromanipulation medium at 38.5° C. until SCNT.

SCNT was performed essentially as previously described (Lai et al., Science 295:1089-1092, 2002; Lai et al., Nat. Biotechnol. 24:435-436, 2006) in micromanipulation medium supplemented with 7.5 μg/mL cytochalasin B. The metaphase II chromosomes and the polar body were aspirated by inserting a micropipette through the zona pellucida and aspirating the polar body and the adjacent cytoplasm into the pipette. Next a donor cell was aspirated into the same pipette, the pipette was inserted into the previously made hole in the zona pellucida, and the cell deposited under the zona pellucida. The nuclear transfer complex was fused in a medium with a low $Ca^{2+}$ concentration (0.3 M mannitol, 0.1 mM $CaCl_2.2H_2O$, 0.1 mM $MgCl_2.6H2O$ and 0.5 mM HEPES), activated with 200 μM thimerosal for 10 min in the dark, and then rinsed and treated with 8 mM dithiothreitol (DTT) for 30 min. Finally the oocytes were rinsed to remove any traces of DTT (Lai et al., Nat. Biotechnol. 24:435-436, 2006). Following fusion/activation, oocytes were washed three times with PZM3 as previously described for 30 min (Im et al., Theriogenology 61:1125-1135, 2004). Those that had fused were cultured for 15-21 hours until surgical embryo transfer to a surrogate.

Surrogate Preparation and Embryo Transfer

The embryonic cleavage rate was examined before transferring the reconstructed embryos into recipients. The recipients were synchronized by administering 18-20 mg Regumate and hCG as previously described (Lai et al., Cloning Stem Cells 5:233-241, 2003). Twelve surrogates on the first day of estrus (designated day 0) or the first day after standing estrus were used. Embryo transfer was performed surgically as previously described (Lai et al., Cloning Stem Cells 5:233-241, 2003) and 94 to 185 embryos were inserted into one oviduct through the ovarian fimbria. Surrogates were checked for pregnancy by abdominal ultrasound examination after day 21 and then checked weekly throughout gestation, and were allowed to go to term. A cesarean section was performed to recover the piglets on day 116-118. After delivery the piglets were provided medical care, fed colostrums, and initially raised on a commercial pig milk replacer until mature enough to be placed on standard pig diets.

Rectal Biopsy

Pigs were lightly anesthetized with ketamine (20 mg/kg) and acepromazine (0.2 mg/kg). A 10 cm anoscope was partially inserted in the rectum and rectal tissue was collected using gastrointestinal biopsy forceps (2.2 mm). Tissue samples were immediately placed in RNAlater (Ambion). Recovery from anesthesia was monitored continuously until the pigs returned to normal activity (2-4 hours).

Quantitative RT-PCR

Quantitative RT-PCR using TaqMan chemistry and an ABI 7500 Fast Real-time PCR System was used to measure pig CFTR mRNA. Briefly, total RNA was isolated from fibroblasts or nasal and rectal biopsy tissue (RNeasy, Qiagen). First-strand cDNA was synthesized with random primers (SuperScript III, Invitrogen). Sequence-specific primers and probes for pig CFTR and GAPDH were designed and ordered using Assays-by-design (Applied Biosystems). For measuring total CFTR mRNA primer/probe sets spanning exons 18 and 19 of CFTR and GAPDH were used in separate reactions. For measuring ΔF508 mRNA levels, one primer set and two probes (F508 and ΔF508) were used in separate reactions. Primer and probe sequences are included in Table 2. TaqMan Fast Universal PCR Master Mix was used for all reactions. The reaction volume was 20 μl (10 μl of 2× Master Mix without UNG, 1 μl of 20× target primer and probe, 8 μl of Nuclease-free water, and 1 μl of cDNA sample). The reaction plates were covered with optical film and centrifuged briefly. The thermocycler conditions were as follows: 20 sec at 95° C., 40 cycles of 95° C. for 3 sec and 60° C. for 30 sec. All experiments were run in triplicate. Because the efficiencies of CFTR and GAPDH amplification were not equal, the relative quantification of transcript levels was performed using the standard curve method.

II. The ΔF508 Mutation—an Interspecies Analysis

The ΔF508 mutation confers at least three defects on human CFTR: it reduces channel activity, it impairs processing, and it reduces the protein's stability at the cell surface. The ΔF508 mutation inhibits gating of CFTR channels from three species (i.e., mouse, pig, and human) studied by the same mechanism, a reduced opening rate. In contrast, the characteristic processing defect observed in human CFTR-ΔF508 is less severe in pig and mouse proteins. This conclusion is supported by our finding that the mouse and pig proteins showed complex glycosylation, were readily excised for patch-clamp experiments at 37° C., immunocytochemistry localized some of the protein to the apical membrane of airway epithelia, and corrected the Cl_ transport defect in CF airway epithelia more than did human CFTR-ΔF508. This shows that there is a gradient in the severity of the ΔF508 processing defect, with human worse than pig, and pig somewhat worse than mouse. Additionally, this also shows that the processing defect and the functional defect in CFTR-ΔF508 arise from different causes.

Vectors and Expression

Human, pig, and mouse CFTR cDNA (SEQ ID NOs:1, 3, and 5) were amplified from *Homo sapiens*, domestic pig (*Sus scrofa*), and domestic mouse (*mus musculus*). We subcloned all three CFTR cDNAs into pcDNA3.1 (Invitrogen) and recombinant adenoviruses. For recombinant adenovirus of mouse CFTR, we had to remove intron 11 which had been inserted previously to stabilize the vector.

For protein processing studies, COS7 cells were electroporated; 3T3 and LLC-PK1 cells were transfected with plasmid and Lipofectamine 2000. For deglycosylation studies, COS7 cells were electroporated with human CFTR or infected with adenovirus encoding pig or mouse CFTR. For patch-clamp studies, HeLa cells were infected with adenovirus encoding mouse CFTR or transfected using a hybrid vaccinia virus system encoding pig CFTR. Expression in human and mouse airway epithelia was with recombinant adenoviruses. Murine tracheal epithelia were cultured from ΔF508/ΔF508 transgenic mice (CFTR$^{tm1Kth}$) or CFTR null mice expressing the intestinal FABP-CFTR (CFTR$^{tm1Unc/FABP-CFTR}$). In the absence of gene transfer, there were no cAMP-stimulated $Cl^-$ currents in either mouse genotype.

Biochemical Studies

COS7 cells were solubilized in lysis buffer with 1% TX-100 and proteinase inhibitors. CFTR was immunoprecipitated with M3A7 antibody (Upstate Technology) and then in vitro phosphorylated as described previously. Note that the consensus phosphorylation sites and N-glycosylation sites are conserved in all three species (FIG. 14). Processing studies in NIH-3T3 and LLC-PK1 cells were carried out similarly to those in COS7 cells. For deglycosylation studies, membranes were isolated from COS7 cells and solubilized in LB plus 1% NP40 (Pierce). Supernatants were divided, immunoprecipitated, and resuspended with or without endoglycosidase H. Following incubation, precipitates were in vitro phosphorylated.

Immunocytochemistry

Three days following gene transfer, epithelia were fixed, permeabilized, and incubated with a mixture of anti-CFTR antibodies (M3A7, MM13-4 (Upstate Biotechnology) and 13-1 (R&D Systems) and anti-ZO-1 (Zymed) primary antibodies, followed by Alexa Fluor-conjugated secondary antibodies (Molecular Probes) and examined by confocal laser scanning microscopy.

Electrophysiology

For Ussing chamber studies, transepithelial $Cl^-$ current was measured 3 days following gene transfer using a $Cl^-$ concentration gradient as previously described. For patch-clamp studies CFTR currents were studied in excised, inside-out membrane patches of HeLa cells as previously described. Channels were activated with the catalytic subunit of PKA and Mg-ATP; PKA was present in all cytosolic solutions that contained ATP. Holding voltage was −50 to −100 mV. Experiments were performed at 23-26° C. Data acquisition, processing, and analysis were performed as previously described. Data are mean±SEM unless otherwise stated. $P<0.05$ was considered statistically significant.

Sequence of Pig CFTR

We cloned the pig CFTR cDNA and used it to predict the amino acid sequence (FIG. 14). The pig CFTR amino acid sequence is nearly 93% identical to that of human CFTR. For comparison, mouse CFTR shows 78% identity to human CFTR. The region immediately surrounding F508 is highly conserved.

Glycosylation of Human, Pig, and Mouse CFTR-ΔF508

The pattern of human CFTR glycosylation changes as the protein migrates from the ER to the Golgi complex. The nascent protein lacking glycosylation is called "band A." In the ER, CFTR undergoes core glycosylation and migrates more slowly during electrophoresis as "band B." In the Golgi complex, more extensive glycosylation occurs, which further slows and broadens the electrophoretic migration of the "band C" form. Differences in glycosylation do not appear to affect function, but do provide a convenient way to assess the biosynthetic processing of CFTR. When we expressed wild-type human, pig, and mouse CFTR in the monkey kidney cell line COS7, we observed the typical appearance of bands B and C (FIG. 15A). Human CFTR-ΔF508 produced band B, but not band C, consistent with defective exit from the ER. This result agrees with many previous reports in several different cell lines. Surprisingly, in addition to band B, mouse CFTR-ΔF508 generated a significant proportion of band C protein. Pig CFTR-ΔF508 also produced a small amount of band C. These results suggested that some mouse and pig mutant protein may have trafficked to the Golgi complex.

To learn whether the differences between the three species of CFTR-ΔF508 depended on the primate COS7 cell line, we expressed the constructs in the mouse NIH-3T3 fibroblast line and the pig LLC-PK1 kidney cell line (FIGS. 15B and C), as well as human HEK-293T cells (not shown). In each of these cell lines, human CFTR-ΔF508 generated only the band B form, whereas pig and mouse CFTR-ΔF508 produced both band B and some fully glycosylated protein, consistent with our studies in COS7 cells. We also noted that some of the wild-type and ΔF508 pig CFTR migrated slightly more rapidly than band B of either human or mouse.

To confirm that the high molecular mass C forms of pig and mouse CFTR-ΔF508 were due to complex glycosylation, we used endoglycosidase H digestion. Endoglycosidase H removes carbohydrate from proteins that contain only the sugar added in the ER, but it does not delete complex glycosylation added in the Golgi complex. Endoglycosidase H treatment shifted the migration of the band B form of all the proteins to the unglycosylated form (FIG. 16). However, like the band C form of the wild-type CFTRs, the fully glycosylated mouse and pig CFTR-ΔF508 were resistant to endoglycosidase H, confirming that these proteins were glycosylated in the Golgi complex.

Expression of Human, Pig, and Mouse CFTR-ΔF508 at the Cell Surface

To determine if the human, pig and mouse CFTR-ΔF508 were localized at the apical membrane of airway, we expressed the proteins in well-differentiated human CF airway epithelia and examined them with confocal immunocytochemistry. Consistent with earlier studies, wild-type human CFTR localized at the apical membrane and human CFTR-ΔF508 appeared to be expressed diffusely throughout the cell (FIG. 17). As expected from the biochemical studies, both pig and mouse wild-type were localized to the apical membrane. However, in contrast to human CFTR-ΔF508, both the pig and mouse mutants were also present in the apical portion of the airway cells.

Single Channel Gating of Human, Pig, and Mouse CFTR-ΔF508

Most, although not all studies indicate that human CFTR-ΔF508 manifests a channel gating defect that reduces activity. To learn whether the ΔF508 mutation compromises the channel activity in pig and mouse CFTR, we studied excised, inside-out patches of membrane containing CFTR channels. We readily detected channels in patches taken from cells expressing pig and mouse CFTR-ΔF508 grown at 37° C., consistent with the conclusion that pig and mouse CFTR-ΔF508 are able to reach the cell membrane under physiological conditions. This contrasts with human CFTR-ΔF508, which must be incubated at lowered temperatures to produce significant amounts of cell surface protein. Phosphorylation by the catalytic domain of cAMP-dependent protein kinase (PKA) and cytosolic ATP were required for activity of all versions studied. The single channel conductances for the wild-type channels were human (8.3 pS)>pig (6.7 pS)>mouse (4.3 pS), and they were not significantly altered by the ΔF508 mutation (FIGS. 18A and 18B). Lansdell et al. (J. Physiol. 508:379-392, 1998) reported that heavily filtering currents recorded from mouse CFTR revealed a subconductance state that was ~10% the amplitude of the full conductance. With heavy filtering, we also observed the subconductance in both wild-type and ΔF508 channels (FIG. 18A).

In the presence of PKA and 1 mM ATP, the open state probability ($P_o$) of wild-type CFTR varied in the order, pig (0.39)≈human (0.37)>mouse (0.08) (FIG. 18B); the values for human were taken from our earlier study. In assessing mouse $P_o$, we did not take into account the subconductance state; as reported by Lansdell et al., it was very difficult to study due to its small single-channel conductance. The ΔF508 mutation reduced the $P_o$ of human CFTR to 27%, pig CFTR to 46%, and mouse CFTR to 50% of the corresponding wild-type channel (FIGS. 18A and 18B). The cause of the reduced $P_o$ was a decrease in the rate of channel opening without a significant alteration of burst duration (FIG. 18B). Thus, in all three species, the ΔF508 mutation altered gating by a similar mechanism.

Transepithelial $Cl^-$ Current Generated by Human, Mouse, and Pig CFTR-ΔF508

Because both pig and mouse CFTR-ΔF508 were partially processed through the Golgi complex and likely targeted to the apical membrane, and because they both retained partial $Cl^-$ channel activity, we predicted they would generate transepithelial $Cl^-$ currents when expressed in well-differentiated CF airway epithelia. To assay transepithelial $Cl^-$ transport, we mounted epithelia in modified Ussing chambers and measured transepithelial $Cl^-$ current. We first inhibited $Na^+$ current with amiloride, which hyperpolarizes the apical membrane voltage, increasing the driving force for $Cl^-$ secretion through CFTR. Then, we increased CFTR activity by elevating cellular levels of cAMP with forskolin and IBMX. Finally, we reduced transepithelial $Cl^-$ current by inhibiting the $Na^+$—$K^+$—$Cl^-$ cotransporter with basolateral bumetanide; the resulting change in current provides a good measure of the $Cl^-$ current. We chose bumetamide rather than CFTR inhibitors, because they can have different efficacy on CFTR from different species.

Expressing wild-type human CFTR produced significant transepithelial $Cl^-$ current (FIGS. 19 and 20), as previously described. The same was true for wild-type pig and mouse CFTR. As expected, human CFTR-ΔF508 failed to generate much current. However, relative to the wild-type current of each species, both pig and mouse CFTR-ΔF508 produced substantial transepithelial $Cl^-$ currents (FIG. 20B). To determine if these results were limited to expression in human epithelia, we repeated the study using airway epithelia derived from CF mice; the results were qualitatively similar (FIGS. 20A and 20B). Thus, pig and mouse CFTR-ΔF508 generated transepithelial $Cl^-$ currents in CF airway epithelia from two different species. These results indicate that some pig and mouse CFTR-ΔF508 was present and active in the apical membrane of airway epithelia.

III. A Transgenic, Non-Human Animal Model of Cystic Fibrosis Using Transgenic Human CFTR-ΔF508

The above-mentioned defects between mutant mouse, pig, and human CFTR illustrate the need for the generation of a transgenic non-human animal model of CF that contains a CFTR-ΔF508 mutation that closely mimics the functional and processing characteristics of the human CFTR-ΔF508. The generation of a large animal, such as a pig, in which the endogenous CFTR gene is knocked-out and a human CFTR-ΔF508 transgene is introduced allows for the study of the causative factor of human CF without suffering from experimental artifacts introduced by the different physical and functional characteristics of the endogenous CFTR of the animal. Such models also facilitate the identification, characterization, and development of approaches (e.g., small molecule-based drugs) that can be used in CF therapy.

Generation of a CFTR−/− Knock-Out, Human CFTR (hCFTR) Transgenic Pig

A yeast artificial chromosome (YAC) containing the entire 230 kb human CFTR gene (wild-type or F508del) plus upstream and downstream sequences is introduced into pig CFTR−/− fetal fibroblasts. One specific example is YAC37AB12 (Anand et al., Genomics 9(1):124-130, 1991). This YAC has been used to complement null CF mice (Manson et al., EMBO 16(14):4238-4249, 1997) and to express human CFTR in Chinese hamster ovary cells (Mogayzel et al., Human Molecular Genetics 6(1):59-68, 1997). Any mutations, such as the CF F508del mutation, are introduced into the YAC by site-directed techniques that are well known in the art. YAC delivery is accomplished, for example, via nuclear microinjection, lipid-mediated transfection, or fusion of fibroblasts with yeast spheroplasts. Since the human CFTR-expressing YAC contains an antibiotic selection marker (different from the marker used to make the CFTR−/− cells), cells positive for YAC transgenesis are screened by antibiotic selection. Resistant cells are then screened by PCR, Southern blot, fluorescence in situ hybridization (FISH), and/or fiber-FISH to assess human CFTR integration, copy number, and integrity. These procedures are optimized to minimize the number of fibroblast doublings and time in culture. Cells deemed appropriate for nuclear transfer are then transferred to enucleated oocytes, fused, and electrically stimulated, and transferred to recipient females.

Alternatives to the YAC approach include the use of a minigene, which is a DNA sequence containing the human CFTR promoter and the entire cDNA (CDS and 5' and 3' UTRs) with the first one, two, or three introns still intact. This approach results in human CFTR that still has normal endogenous levels of expression without the large size of the entire gene (<40 kb vs. >300 kb). Additionally, human CFTR cDNA is introduced (i.e., no introns) with either a CFTR promoter, a promoter with CFTR-like tissue expression (e.g., cytokeratin 18 promoter), or a constitutive promoter such as the CMV promoter. In another alternative, the human CFTR and necessary regulation, selection, and tracking elements (e.g., promoter, antibiotic resistance gene, GFP, luciferase) are introduced into a pig fibroblast or fertilized embryo by means of a viral vector, such as a retrovirus or lentivirus. Each of these methods results in the random integration of the wild-type or mutated human CFTR gene in the pig genome, the exact location of which can be later identified.

Other Embodiments

All publications, patents, and other citations noted in this specification are incorporated herein by reference as if each individual publication, patent, or other citation were specifically and individually indicated to be incorporated by reference. Although the invention has been described above in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

Use in the claims and elsewhere herein of singular forms, such as "a" and "the," does not exclude indication of the corresponding plural form, unless the context indicates to the contrary. Thus, for example, if a claim indicates the presence of "a" mutation in "a" gene, it can be interpreted as covering one or more mutations, in one or more genes, unless otherwise indicated.

Other embodiments are within the following claims.

What is claimed is:

1. A method of identifying a therapeutic agent that can be used in the treatment of cystic fibrosis, the method comprising administering a candidate therapeutic agent to a transgenic pig whose genome has a homozygous disruption in a cystic fibrosis membrane transporter (CFTR) gene, wherein the pig has a symptom of cystic fibrosis, and monitoring the pig for a symptom of cystic fibrosis, wherein detection of improvement in a symptom of cystic fibrosis indicates the identification of a compound that can be used in the treatment of cystic fibrosis.

2. The method of claim 1, wherein the symptom of cystic fibrosis is monitored in the lung, pancreas, intestine, liver, or kidney of the pig.

* * * * *

SEQUENCE LISTING

<160> NUMBER OF SEQ ID NOS: 34

<210> SEQ ID NO 1
<211> LENGTH: 6132
<212> TYPE: DNA
<213> ORGANISM: Homo sapiens

<400> SEQUENCE: 1
aattggaagc aaatgacatc acagcaggtc agagaaaaag ggttgagcgg caggcaccca 60
gagtagtagg tctttggcat taggagcttg agcccagacg gccctagcag ggaccccagc 120
gcccgagaga ccatgcagag gtcgcctctg gaaaaggcca gcgttgtctc caaacttttt 180
ttcagctgga ccagaccaat tttgaggaaa ggatacagac agcgcctgga attgtcagac 240
atataccaaa tcccttctgt tgattctgct gacaatctat ctgaaaaatt ggaaagagaa 300
tgggatagag agctggcttc aaagaaaaat cctaaactca ttaatgccct tcggcgatgt 360
tttttctgga gatttatgtt ctatggaatc tttttatatt taggggaagt caccaaagca 420
gtacagcctc tcttactggg aagaatcata gcttcctatg acccggataa caaggaggaa 480
cgctctatcg cgatttatct aggcataggc ttatgccttc tctttattgt gaggacactg 540
ctcctacacc cagccatttt tggccttcat cacattggaa tgcagatgag aatagctatg 600
tttagtttga tttataagaa gactttaaag ctgtcaagcc gtgttctaga taaaataagt 660
attggacaac ttgttagtct cctttccaac aacctgaaca aatttgatga aggacttgca 720
ttggcacatt tcgtgtggat cgctcctttg caagtggcac tcctcatggg gctaatctgg 780
gagttgttac aggcgtctgc cttctgtgga cttggtttcc tgatagtcct tgcccttttt 840
caggctgggc tagggagaat gatgatgaag tacagagatc agagagctgg gaagatcagt 900
gaaagacttg tgattacctc agaaatgatt gaaaatatcc aatctgttaa ggcatactgc 960
tgggaagaag caatggaaaa aatgattgaa aacttaagac aaacagaact gaaactgact 1020
cggaaggcag cctatgtgag atacttcaat agctcagcct tcttcttctc agggttcttt 1080
gtggtgtttt tatctgtgct tccctatgca ctaatcaaag gaatcatcct ccggaaaata 1140
ttcaccacca tctcattctg cattgttctg cgcatggcgg tcactcggca atttccctgg 1200
gctgtacaaa catggtatga ctctcttgga gcaataaaca aaatacagga tttcttacaa 1260
aagcaagaat ataagacatt ggaatataac ttaacgacta cagaagtagt gatggagaat 1320
gtaacagcct tctgggagga gggatttggg gaattatttg agaaagcaaa acaaaacaat 1380
aacaatagaa aaacttctaa tggtgatgac agcctcttct tcagtaattt ctcacttctt 1440
ggtactcctg tcctgaaaga tattaatttc aagatagaaa gaggacagtt gttggcggtt 1500
gctggatcca ctggagcagg caagacttca cttctaatgg tgattatggg agaactggag 1560
ccttcagagg gtaaaattaa gcacagtgga agaatttcat tctgttctca gttttcctgg 1620
attatgcctg gcaccattaa agaaaatatc atctttggtg tttcctatga tgaatataga 1680
tacagaagcg tcatcaaagc atgccaacta gaagaggaca tctccaagtt tgcagagaaa 1740
gacaatatag ttcttggaga aggtggaatc acactgagtg gaggtcaacg agcaagaatt 1800
tctttagcaa gagcagtata caaagatgct gatttgtatt tattagactc tccttttgga 1860
tacctagatg ttttaacaga aaaagaaata tttgaaagct gtgtctgtaa actgatggct 1920
aacaaaacta ggattttggt cacttctaaa atggaacatt taaagaaagc tgacaaaata 1980
ttaattttgc atgaaggtag cagctatttt tatgggacat tttcagaact ccaaaatcta 2040

```
cagccagact ttagctcaaa actcatggga tgtgattctt tcgaccaatt tagtgcagaa   2100
agaagaaatt caatcctaac tgagacctta caccgtttct cattagaagg agatgctcct   2160
gtctcctgga cagaaacaaa aaaacaatct tttaaacaga ctggagagtt tggggaaaaa   2220
aggaagaatt ctattctcaa tccaatcaac tctatacgaa aattttccat tgtgcaaaag   2280
actcccttac aaatgaatgg catcgaagag gattctgatg agcctttaga gagaaggctg   2340
tccttagtac cagattctga gcagggagag gcgatactgc ctcgcatcag cgtgatcagc   2400
actggcccca cgcttcaggc acgaaggagg cagtctgtcc tgaacctgat gacacactca   2460
gttaaccaag gtcagaacat tcaccgaaag acaacagcat ccacacgaaa agtgtcactg   2520
gcccctcagg caaacttgac tgaactggat atatattcaa gaaggttatc tcaagaaact   2580
ggcttggaaa taagtgaaga aattaacgaa gaagacttaa aggagtgctt ttttgatgat   2640
atggagagca taccagcagt gactacatgg aacacatacc ttcgatatat tactgtccac   2700
aagagcttaa tttttgtgct aatttggtgc ttagtaattt ttctggcaga ggtggctgct   2760
tctttggttg tgctgtggct ccttggaaac actcctcttc aagacaaagg gaatagtact   2820
catagtagaa ataacagcta tgcagtgatt atcaccagca ccagttcgta ttatgtgttt   2880
tacatttacg tgggagtagc cgacactttg cttgctatgg gattcttcag aggtctacca   2940
ctggtgcata ctctaatcac agtgtcgaaa attttacacc acaaaatgtt acattctgtt   3000
cttcaagcac ctatgtcaac cctcaacacg ttgaaagcag gtgggattct taatagattc   3060
tccaaagata tagcaatttt ggatgacctt ctgcctctta ccatatttga cttcatccag   3120
ttgttattaa ttgtgattgg agctatagca gttgtcgcag ttttacaacc ctacatcttt   3180
gttgcaacag tgccagtgat agtggctttt attatgttga gagcatattt cctccaaacc   3240
tcacagcaac tcaaacaact ggaatctgaa ggcaggagtc caattttcac tcatcttgtt   3300
acaagcttaa aaggactatg gacacttcgt gccttcggac ggcagcctta ctttgaaact   3360
ctgttccaca aagctctgaa tttacatact gccaactggt tcttgtacct gtcaacactg   3420
cgctggttcc aaatgagaat agaaatgatt tttgtcatct tcttcattgc tgttaccttc   3480
atttccattt taacaacagg agaaggagaa ggaagagttg gtattatcct gactttagcc   3540
atgaatatca tgagtacatt gcagtgggct gtaaactcca gcatagatgt ggatagcttg   3600
atgcgatctg tgagccgagt ctttaagttc attgacatgc caacagaagg taaacctacc   3660
aagtcaacca aaccatacaa gaatggccaa ctctcgaaag ttatgattat tgagaattca   3720
cacgtgaaga aagatgacat ctggccctca gggggccaaa tgactgtcaa agatctcaca   3780
gcaaaataca cagaaggtgg aaatgccata ttagagaaca tttccttctc aataagtcct   3840
ggccagaggg tgggcctctt gggaagaact ggatcaggga agagtacttt gttatcagct   3900
tttttgagac tactgaacac tgaaggagaa atccagatcg atggtgtgtc ttgggattca   3960
ataactttgc aacagtggag gaaagccttt ggagtgatac cacagaaagt atttattttt   4020
tctggaacat ttagaaaaaa cttggatccc tatgaacagt ggagtgatca agaaatatgg   4080
aaagttgcag atgaggttgg gctcagatct gtgatagaac agtttcctgg gaagcttgac   4140
tttgtccttg tggatggggg ctgtgtccta agccatggcc acaagcagtt gatgtgcttg   4200
gctagatctg ttctcagtaa ggcgaagatc ttgctgcttg atgaacccag tgctcatttg   4260
gatccagtaa cataccaaat aattagaaga actctaaaac aagcatttgc tgattgcaca   4320
gtaattctct gtgaacacag gatagaagca atgctggaat gccaacaatt tttggtcata   4380
gaagagaaca aagtgcggca gtacgattcc atccagaaac tgctgaacga gaggagcctc   4440
```

```
ttccggcaag ccatcagccc ctccgacagg gtgaagctct ttccccaccg gaactcaagc   4500

aagtgcaagt ctaagcccca gattgctgct ctgaaagagg agacagaaga agaggtgcaa   4560

gatacaaggc tttagagagc agcataaatg ttgacatggg acatttgctc atggaattgg   4620

agctcgtggg acagtcacct catggaattg gagctcgtgg aacagttacc tctgcctcag   4680

aaaacaagga tgaattaagt tttttttaa aaaagaaaca tttggtaagg ggaattgagg   4740

acactgatat gggtcttgat aaatggcttc ctggcaatag tcaaattgtg tgaaaggtac   4800

ttcaaatcct tgaagattta ccacttgtgt tttgcaagcc agattttcct gaaaaccctt   4860

gccatgtgct agtaattgga aaggcagctc taaatgtcaa tcagcctagt tgatcagctt   4920

attgtctagt gaaactcgtt aatttgtagt gttggagaag aactgaaatc atacttctta   4980

gggttatgat taagtaatga taactggaaa cttcagcggt ttatataagc ttgtattcct   5040

ttttctctcc tctccccatg atgtttagaa acacaactat attgtttgct aagcattcca   5100

actatctcat ttccaagcaa gtattagaat accacaggaa ccacaagact gcacatcaaa   5160

atatgcccca ttcaacatct agtgagcagt caggaaagag aacttccaga tcctggaaat   5220

cagggttagt attgtccagg tctaccaaaa atctcaatat ttcagataat cacaatacat   5280

cccttacctg ggaaagggct gttataatct ttcacagggg acaggatggt tcccttgatg   5340

aagaagttga tatgcctttt cccaactcca gaaagtgaca agctcacaga cctttgaact   5400

agagtttagc tggaaaagta tgttagtgca aattgtcaca ggacagccct tctttccaca   5460

gaagctccag gtagagggtg tgtaagtaga taggccatgg gcactgtggg tagacacaca   5520

tgaagtccaa gcatttagat gtataggttg atggtggtat gttttcaggc tagatgtatg   5580

tacttcatgc tgtctacact aagagagaat gagagacaca ctgaagaagc accaatcatg   5640

aattagtttt atatgcttct gttttataat tttgtgaagc aaaatttttt ctctaggaaa   5700

tatttatttt aataatgttt caaacatata taacaatgct gtattttaaa agaatgatta   5760

tgaattacat ttgtataaaa taatttttat atttgaaata ttgacttttt atggcactag   5820

tatttctatg aaatattatg ttaaaactgg gacaggggag aacctagggt gatattaacc   5880

aggggccatg aatcaccttt tggtctggag ggaagccttg gggctgatgc agttgttgcc   5940

cacagctgta tgattcccag ccagcacagc ctcttagatg cagttctgaa gaagatggta   6000

ccaccagtct gactgtttcc atcaagggta cactgccttc tcaactccaa actgactctt   6060

aagaagactg cattatattt attactgtaa gaaaatatca cttgtcaata aaatccatac   6120

atttgtgtga aa                                                        6132
```

<210> SEQ ID NO 2
<211> LENGTH: 1480
<212> TYPE: PRT
<213> ORGANISM: Homo sapiens

<400> SEQUENCE: 2

```
Met Gln Arg Ser Pro Leu Glu Lys Ala Ser Val Val Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr Gln Ile Pro Ser Val Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80
```

-continued

```
Phe Met Phe Tyr Gly Ile Phe Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110

Asn Lys Glu Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Ala Leu Leu Met Gly Leu Ile Trp Glu Leu Leu Gln Ala Ser Ala Phe
    210                 215                 220

Cys Gly Leu Gly Phe Leu Ile Val Leu Ala Leu Phe Gln Ala Gly Leu
225                 230                 235                 240

Gly Arg Met Met Met Lys Tyr Arg Asp Gln Arg Ala Gly Lys Ile Ser
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Phe Phe Val Val Phe Leu
305                 310                 315                 320

Ser Val Leu Pro Tyr Ala Leu Ile Lys Gly Ile Ile Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Glu Leu Phe Glu Lys Ala Lys Gln Asn Asn
                405                 410                 415

Asn Asn Arg Lys Thr Ser Asn Gly Asp Asp Ser Leu Phe Phe Ser Asn
            420                 425                 430

Phe Ser Leu Leu Gly Thr Pro Val Leu Lys Asp Ile Asn Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510
```

```
Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540

Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu Asn Glu Gly Ser Ser
    610                 615                 620

Tyr Phe Tyr Gly Thr Phe Ser Glu Leu Gln Asn Leu Gln Pro Asp Phe
625                 630                 635                 640

Ser Ser Lys Leu Met Gly Cys Asp Ser Phe Asp Gln Phe Ser Ala Glu
                645                 650                 655

Arg Arg Asn Ser Ile Leu Thr Glu Thr Leu His Arg Phe Ser Leu Glu
            660                 665                 670

Gly Asp Ala Pro Val Ser Trp Thr Glu Thr Lys Lys Gln Ser Phe Lys
        675                 680                 685

Gln Thr Gly Glu Phe Gly Glu Lys Arg Lys Asn Ser Ile Leu Asn Pro
    690                 695                 700

Ile Asn Ser Ile Arg Lys Phe Ser Ile Val Gln Lys Thr Pro Leu Gln
705                 710                 715                 720

Met Asn Gly Ile Glu Glu Asp Ser Asp Glu Pro Leu Glu Arg Arg Leu
                725                 730                 735

Ser Leu Val Pro Asp Ser Glu Gln Gly Glu Ala Ile Leu Pro Arg Ile
            740                 745                 750

Ser Val Ile Ser Thr Gly Pro Thr Leu Gln Ala Arg Arg Arg Gln Ser
        755                 760                 765

Val Leu Asn Leu Met Thr His Ser Val Asn Gln Gly Gln Asn Ile His
    770                 775                 780

Arg Lys Thr Thr Ala Ser Thr Arg Lys Val Ser Leu Ala Pro Gln Ala
785                 790                 795                 800

Asn Leu Thr Glu Leu Asp Ile Tyr Ser Arg Arg Leu Ser Gln Glu Thr
                805                 810                 815

Gly Leu Glu Ile Ser Glu Glu Ile Asn Glu Glu Asp Leu Lys Glu Cys
            820                 825                 830

Leu Phe Asp Asp Met Glu Ser Ile Pro Ala Val Thr Thr Trp Asn Thr
        835                 840                 845

Tyr Leu Arg Tyr Ile Thr Val His Lys Ser Leu Ile Phe Val Leu Ile
    850                 855                 860

Trp Cys Leu Val Ile Phe Leu Ala Glu Val Ala Ala Ser Leu Val Val
865                 870                 875                 880

Leu Trp Leu Leu Gly Asn Thr Pro Leu Gln Asp Lys Gly Asn Ser Thr
                885                 890                 895

His Ser Arg Asn Asn Ser Tyr Ala Val Ile Ile Thr Ser Thr Ser Ser
            900                 905                 910

Tyr Tyr Val Phe Tyr Ile Tyr Val Gly Val Ala Asp Thr Leu Leu Ala
        915                 920                 925

Met Gly Phe Phe Arg Gly Leu Pro Leu Val His Thr Leu Ile Thr Val
    930                 935                 940
```

-continued

```
Ser Lys Ile Leu His His Lys Met Leu His Ser Val Leu Gln Ala Pro
945                 950                 955                 960

Met Ser Thr Leu Asn Thr Leu Lys Ala Gly Gly Ile Leu Asn Arg Phe
                965                 970                 975

Ser Lys Asp Ile Ala Ile Leu Asp Asp Leu Leu Pro Leu Thr Ile Phe
            980                 985                 990

Asp Phe Ile Gln Leu Leu Leu Ile  Val Ile Gly Ala Ile  Ala Val Val
        995                 1000                 1005

Ala Val  Leu Gln Pro Tyr Ile  Phe Val Ala Thr Val  Pro Val Ile
    1010                 1015                 1020

Val Ala  Phe Ile Met Leu Arg  Ala Tyr Phe Leu Gln  Thr Ser Gln
    1025                 1030                 1035

Gln Leu  Lys Gln Leu Glu Ser  Glu Gly Arg Ser Pro  Ile Phe Thr
    1040                 1045                 1050

His Leu  Val Thr Ser Leu Lys  Gly Leu Trp Thr Leu  Arg Ala Phe
    1055                 1060                 1065

Gly Arg  Gln Pro Tyr Phe Glu  Thr Leu Phe His Lys  Ala Leu Asn
    1070                 1075                 1080

Leu His  Thr Ala Asn Trp Phe  Leu Tyr Leu Ser Thr  Leu Arg Trp
    1085                 1090                 1095

Phe Gln  Met Arg Ile Glu Met  Ile Phe Val Ile Phe  Phe Ile Ala
    1100                 1105                 1110

Val Thr  Phe Ile Ser Ile Leu  Thr Thr Gly Glu Gly  Glu Gly Arg
    1115                 1120                 1125

Val Gly  Ile Ile Leu Thr Leu  Ala Met Asn Ile Met  Ser Thr Leu
    1130                 1135                 1140

Gln Trp  Ala Val Asn Ser Ser  Ile Asp Val Asp Ser  Leu Met Arg
    1145                 1150                 1155

Ser Val  Ser Arg Val Phe Lys  Phe Ile Asp Met Pro  Thr Glu Gly
    1160                 1165                 1170

Lys Pro  Thr Lys Ser Thr Lys  Pro Tyr Lys Asn Gly  Gln Leu Ser
    1175                 1180                 1185

Lys Val  Met Ile Ile Glu Asn  Ser His Val Lys Lys  Asp Asp Ile
    1190                 1195                 1200

Trp Pro  Ser Gly Gly Gln Met  Thr Val Lys Asp Leu  Thr Ala Lys
    1205                 1210                 1215

Tyr Thr  Glu Gly Gly Asn Ala  Ile Leu Glu Asn Ile  Ser Phe Ser
    1220                 1225                 1230

Ile Ser  Pro Gly Gln Arg Val  Gly Leu Leu Gly Arg  Thr Gly Ser
    1235                 1240                 1245

Gly Lys  Ser Thr Leu Leu Ser  Ala Phe Leu Arg Leu  Leu Asn Thr
    1250                 1255                 1260

Glu Gly  Glu Ile Gln Ile Asp  Gly Val Ser Trp Asp  Ser Ile Thr
    1265                 1270                 1275

Leu Gln  Gln Trp Arg Lys Ala  Phe Gly Val Ile Pro  Gln Lys Val
    1280                 1285                 1290

Phe Ile  Phe Ser Gly Thr Phe  Arg Lys Asn Leu Asp  Pro Tyr Glu
    1295                 1300                 1305

Gln Trp  Ser Asp Gln Glu Ile  Trp Lys Val Ala Asp  Glu Val Gly
    1310                 1315                 1320

Leu Arg  Ser Val Ile Glu Gln  Phe Pro Gly Lys Leu  Asp Phe Val
    1325                 1330                 1335

Leu Val  Asp Gly Gly Cys Val  Leu Ser His Gly His  Lys Gln Leu
    1340                 1345                 1350
```

-continued

```
Met Cys  Leu Ala Arg Ser Val  Leu Ser Lys Ala Lys  Ile Leu Leu
    1355                 1360                 1365

Leu Asp  Glu Pro Ser Ala His  Leu Asp Pro Val Thr  Tyr Gln Ile
    1370                 1375                 1380

Ile Arg  Arg Thr Leu Lys Gln  Ala Phe Ala Asp Cys  Thr Val Ile
    1385                 1390                 1395

Leu Cys  Glu His Arg Ile Glu  Ala Met Leu Glu Cys  Gln Gln Phe
    1400                 1405                 1410

Leu Val  Ile Glu Glu Asn Lys  Val Arg Gln Tyr Asp  Ser Ile Gln
    1415                 1420                 1425

Lys Leu  Leu Asn Glu Arg Ser  Leu Phe Arg Gln Ala  Ile Ser Pro
    1430                 1435                 1440

Ser Asp  Arg Val Lys Leu Phe  Pro His Arg Asn Ser  Ser Lys Cys
    1445                 1450                 1455

Lys Ser  Lys Pro Gln Ile Ala  Ala Leu Lys Glu Glu  Thr Glu Glu
    1460                 1465                 1470

Glu Val  Gln Asp Thr Arg Leu
    1475                 1480
```

<210> SEQ ID NO 3
<211> LENGTH: 6299
<212> TYPE: DNA
<213> ORGANISM: Mus musculus

<400> SEQUENCE: 3

```
aattggaagc aaatgacatc acctcaggtc tgagtaaaag ggacgagcca aaagcattga     60
cctggtcctg gatatccaga tgtcgagtcc aacctgaatt tagccgaaca cagacctcat    120
tgctcacgga gacatcatgc agaagtcgcc tttggagaaa gccagcttta tctccaaact    180
cttcttcagc tggaccacac caattttgag gaaagggtac agacaccact tggagttgtc    240
agacatatac caagcccctt ctgctgattc agctgaccac ttgtctgaaa aactagaaag    300
agaatgggac agagaacaag cttcaaaaaa gaatccccag cttatccacg cccttcggcg    360
atgctttttc tggagattcc tcttctatgg aattttgcta tacctagggg aagtcaccaa    420
ggctgtccag cctgtcttgc taggaagaat catagcatcc tatgatccag aaaacaaggt    480
ggaacgttcc attgccattt accttggcat aggcttatgc cttctcttca ttgtcaggac    540
actgcttctt cacccagcta tttttggcct tcatcgcatt ggaatgcaga tgagaacagc    600
tatgtttagc ttgatttata agaagacttt aaagttgtca agccgcgttc ttgataaaat    660
aagtattgga caacttgtta gtcttctttc caacaacctg aacaaatttg atgaaggact    720
tgccttggca cattttatat ggattgctcc tttacaagtg actcttctga tggggcttct    780
ctgggacttg ttacagttct cagccttctg tggccttggt ttactgataa tcctggttat    840
ttttcaagct atcctaggga agatgatggt gaagtacaga gatcaaagag ctgcaaagat    900
caatgaaaga ctcgtgatca catcagaaat tattgataat atctattctg ttaaggcata    960
ttgttgggaa tcagcgatgg agaaaatgat tgaaaacttg agagaggtgg agctgaaaat   1020
gacccggaag gcggcctata tgaggttctt cactagctct gccttcttct tttcagggtt   1080
ctttgtagtc tttctatctg tgcttcccta cacagtcatc aacggaatcg tcctacgaaa   1140
aatattcaca accatttcat tctgcattgt cctacgtatg tcagtcacgc ggcagttccc   1200
cactgccgta cagatatggt atgattcttt tggaatgata agaaaaatac aggatttcct   1260
gcagaaacaa gagtataaag tactggagta taacttaatg accacaggca taatcatgga   1320
aaatgtaaca gcattttggg aggagggatt tggggaatta ctgcagaaag cacaacaaag   1380
```

caatggtgac agaaaacatt ccagtgatga gaacaatgtc agtttcagtc atctctgcct 1440
tgtgggaaat cctgtgctga aaaacatcaa tttgaatata gagaaaggag agatgttggc 1500
tattactgga tctactggac taggaaagac atcactcctg atgttgattt tgggagaact 1560
ggaagcttca gagggaatta ttaagcacag tggaagagtt tcattctgct ctcaattttc 1620
ttggattatg ccgggtacta tcaaagaaaa tatcatcttt ggtgtttcct atgatgagta 1680
cagatataag agtgttgtca aagcttgcca actacagcag gacatcacca agtttgcaga 1740
acaagacaac acagttcttg gagaaggtgg agtcacactg agtggaggtc agcgtgcaag 1800
gatttcttta gcaagagcag tatataaaga tgctgatttg tacctattag attccccttt 1860
tggatatcta gatgttttta ctgaagaaca agtatttgaa agctgtgttt gtaaattgat 1920
ggccaacaaa actaggattt tggttacatc taaaatggaa cacttaagga aagctgacaa 1980
aatactaatt ttgcatcagg ggactagcta tttttatggg acattttctg agctacaaag 2040
tctacgtccg agcttcagtt cgaaactcat ggggtatgat acttttgacc agtttactga 2100
ggaaagaaga agttcaattc taactgagac cttacgcagg ttctcagtag acgattcctc 2160
tgccccgtgg agcaaaccca aacagtcgtt tagacagact ggagaggtgg gagaaaaaag 2220
gaagaactct attctaaatt cattcagctc tgtaaggaaa atttccattg tgcaaaagac 2280
tccattatgt atcgatggag agtctgatga tctccaagaa aagagactgt ccctagttcc 2340
ggattctgaa caggggggagg ctgctctgcc gcgcagcaac atgatcgcca ccggccccac 2400
atttccaggc agaagaagac agtctgtttt ggatctgatg acgttcacac ccaactcagg 2460
ctccagcaat cttcagagga ccagaacttc tattcgaaaa atctccttag tccctcagat 2520
aagcttaaat gaagtggatg tatattcaag gagattatcg caagatagca cactgaacat 2580
cactgaagaa attaacgaag aagatttaaa ggagtgtttt cttgatgatg tgatcaagat 2640
acccccggtg acaacatgga acacatacct acgatatttt actctccata aaggcttact 2700
gctagtgctg atttggtgcg tactggtttt tctggttgag gtggctgctt ctttatttgt 2760
gttatggttg cttaaaaaca accctgttaa cagtggaaac aatggtacta aaatttccaa 2820
tagctcctac gttgtgatca tcaccagtac cagtttctat tatatttttt acatttacgt 2880
gggagtggct gacactttgc ttgccctgag cctcttcaga ggtttgccgc tggtgcatac 2940
gttaatcaca gcatcaaaaa ttttgcacag gaaaatgtta cactccattc ttcacgcccc 3000
tatgtcgacc atcagcaagc tgaaagcagg tgggattctt aacagattct ccaaagatat 3060
agcaattttg gatgactttc tgcctcttac catttttgac ttcattcagt tggtgttcat 3120
tgtgattgga gctataatag tcgtctcggc attacaaccc tacatcttcc tagcaacggt 3180
gccagggcta gtagtcttta ttttactgag ggcctacttc cttcatacag cacagcagct 3240
caaacaactg gaatctgaag gcaggagtcc aattttcacc caccttgtga caagcttaaa 3300
aggactctgg acacttcgag ccttccgacg ccagacttac tttgaaactc tgttccacaa 3360
agctctgaat ttgcacactg ccaactggtt tatgtatctg gcaaccttgc gctggttcca 3420
aatgagaata gacatgatat ttgtcctctt cttcattgtt gttaccttca tctccatttt 3480
aacaacaggt gaaggagaag gaacagctgg tattattcta actttagcta tgaatatcat 3540
gagtactttg cagtgggctg tgaactcaag cattgataca gatagcttga tgcgatctgt 3600
gagcagagtg tttaagttta ttgatataca aacagaagaa agtatgtaca cacagataat 3660
taaagaacta cctagagaag gatcatctga cgttttagtc attaagaatg agcatgtgaa 3720
gaaaagtgat atctggccct ctggaggcga aatggttgtc aaagacctta ctgtgaaata 3780

-continued

```
catggatgat ggaaatgccg tattagagaa catttctttt tcaataagtc ctggacagag   3840
ggtggggctc ttaggaagaa ctggatcagg aaaaagtact ttgctttcag catttttacg   3900
aatgttgaac attaaaggtg atatagagat tgatggtgtc tcatggaatt cagtgacctt   3960
acaagaatgg aggaaagctt tcggagtgat aacacagaaa gtatttatct tttctggaac   4020
attcagacaa aacctggatc ccaatggaaa atggaaagat gaagaaatat ggaaagttgc   4080
agatgaggtt ggactcaagt ctgtaataga gcagtttcct ggacagctca actttaccct   4140
tgtggatggg ggttatgtgc taagccatgg ccataagcaa ttaatgtgct tggcccgatc   4200
agttctcagt aaggccaaga tcatactgct tgatgagccc agtgcccatc tagaccccat   4260
aacataccaa gtcattcgac gagttctaaa acaagccttc gctggttgca cagtcatcct   4320
ctgtgaacac aggatagaag cgatgttgga ttgccagcga tttttggtca tagaagagag   4380
caatgtctgg cagtacgact ccccttcaggc acttctgagt gagaagagta tcttccagca   4440
ggccattagc tcctcggaaa agatgaggtt cttccagggc cgccactcca gcaagcacaa   4500
gcctcggacg caaattactg ctctgaaaga ggagacagaa gaagaagttc aagaaacccg   4560
tctctagtgc tgggatgctg aggaagcaac tcagtgcgca ctgagtccat tcccagaacc   4620
catgcagaat gaaaaaagcc aggcatttcc catgcttcta accccagtgc tgggacacag   4680
agacaggtgg atccctgggg ctctgtggca agtgatccta gcccacaaag agagttccag   4740
gctgggcacc tgagggacaa tacctgtgga tatactcttg cttccacatg caagtacata   4800
tacacatgca tgcacattag tggacataca cacagaaaag caaagaagaa ggaaagaggg   4860
aagaaaatag tgcaaataat tgcaaaacga tcatgtatgg agtctgctca tggacttaga   4920
ggaggtgaac tctactacct gtgcctttga agggtgaagc ctgcgacttg ctctttaaga   4980
gactgttttg gaagagagtt caaaaacgtt catatgggta tgggtaactg actttccagc   5040
agtagtcaaa ttgtttgaac ttcagatagt tgataatgac cacttgtgta ttgcaaggca   5100
gatttttctg aaaacatttg cccccctaata gtagctgaaa aagcagctat aaatgccaac   5160
caggttagtc attcggctta ttgttcagta cagctggtta atttgcatta ttgaagaact   5220
gaaattatag tgcttagata tagaacaaag taaagagaac taaaaacagt gtcttatata   5280
actcaaagcc caacttactt tcctctaaga tatgtattgc cttctataca ttttctgccc   5340
cattccaagc aaatgttaga atattataca aaatactggg tggtattgat tgaaagatgc   5400
ccgacatctg gtgatctagt aacccatcag gattaaggat atccaggtct tggaaattaa   5460
ggttaagacc atctagcctt actaccgtac agctaaacat tcttattacc agaataagac   5520
ctaggaaaaa gaactgtttc agtcccataa agtggcctgg ataatttcct tgatatggaa   5580
atcgacacac ttatgttccc agaaagcaac agatctttaa gacttctgaa gtgaaggaag   5640
gttgtgttag tgcaaactag tgcagcccag tgccaggtcc aggagttaac atgtagacag   5700
gccatggact gtgtgggtag atgctcatgg aaatgtgcag tagtatgttc atgtgctctc   5760
agctagctgt gtgtacttca aactgtctcc acagagttgt tggggagaca ctctgaaaaa   5820
gaattaattg tgaattagtt ttatatactt tgttttataa tttgtgatgc aaatgaaaat   5880
ttctctggga aatatttatt ttagtaataa tgtttcaaac tatatataac aatgctgtat   5940
tttaagaatg attacataat gacttatatt tgtataaaat aatttttata tttgaaatgt   6000
taacttttta tagcactagc tattttaaaa caggggagtg aggaggacag ggatgataag   6060
gatcattcaa cttcatgttg tgaagacgag ctgatgtaaa tcttgtaccc atctgtgtgg   6120
ttctcagaca acacatgctc tcttttaatg cagctttgaa gaagatggta ccaaaggtta   6180
```

-continued

```
agacggcccc ctgatgggca catcaacttc tgaactgcaa actaagcttt agaggaatgt   6240

attatattta ttactgtaat agaatatcat gtgtcaataa aatcctttta tttgtgtga    6299


<210> SEQ ID NO 4
<211> LENGTH: 1476
<212> TYPE: PRT
<213> ORGANISM: Mus musculus

<400> SEQUENCE: 4

Met Gln Lys Ser Pro Leu Glu Lys Ala Ser Phe Ile Ser Lys Leu Phe
1               5                   10                  15

Phe Ser Trp Thr Thr Pro Ile Leu Arg Lys Gly Tyr Arg His His Leu
            20                  25                  30

Glu Leu Ser Asp Ile Tyr Gln Ala Pro Ser Ala Asp Ser Ala Asp His
        35                  40                  45

Leu Ser Glu Lys Leu Glu Arg Glu Trp Asp Arg Glu Gln Ala Ser Lys
    50                  55                  60

Lys Asn Pro Gln Leu Ile His Ala Leu Arg Arg Cys Phe Phe Trp Arg
65                  70                  75                  80

Phe Leu Phe Tyr Gly Ile Leu Leu Tyr Leu Gly Glu Val Thr Lys Ala
                85                  90                  95

Val Gln Pro Val Leu Leu Gly Arg Ile Ile Ala Ser Tyr Asp Pro Glu
            100                 105                 110

Asn Lys Val Glu Arg Ser Ile Ala Ile Tyr Leu Gly Ile Gly Leu Cys
        115                 120                 125

Leu Leu Phe Ile Val Arg Thr Leu Leu Leu His Pro Ala Ile Phe Gly
    130                 135                 140

Leu His Arg Ile Gly Met Gln Met Arg Thr Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Ile Trp Ile Ala Pro Leu Gln Val
        195                 200                 205

Thr Leu Leu Met Gly Leu Leu Trp Asp Leu Leu Gln Phe Ser Ala Phe
    210                 215                 220

Cys Gly Leu Gly Leu Leu Ile Ile Leu Val Ile Phe Gln Ala Ile Leu
225                 230                 235                 240

Gly Lys Met Met Val Lys Tyr Arg Asp Gln Arg Ala Ala Lys Ile Asn
                245                 250                 255

Glu Arg Leu Val Ile Thr Ser Glu Ile Ile Asp Asn Ile Tyr Ser Val
            260                 265                 270

Lys Ala Tyr Cys Trp Glu Ser Ala Met Glu Lys Met Ile Glu Asn Leu
        275                 280                 285

Arg Glu Val Glu Leu Lys Met Thr Arg Lys Ala Ala Tyr Met Arg Phe
    290                 295                 300

Phe Thr Ser Ser Ala Phe Phe Phe Ser Gly Phe Phe Val Val Phe Leu
305                 310                 315                 320

Ser Val Leu Pro Tyr Thr Val Ile Asn Gly Ile Val Leu Arg Lys Ile
                325                 330                 335

Phe Thr Thr Ile Ser Phe Cys Ile Val Leu Arg Met Ser Val Thr Arg
            340                 345                 350

Gln Phe Pro Thr Ala Val Gln Ile Trp Tyr Asp Ser Phe Gly Met Ile
        355                 360                 365
```

-continued

```
Arg Lys Ile Gln Asp Phe Leu Gln Lys Gln Glu Tyr Lys Val Leu Glu
    370                 375                 380

Tyr Asn Leu Met Thr Thr Gly Ile Ile Met Glu Asn Val Thr Ala Phe
385                 390                 395                 400

Trp Glu Glu Gly Phe Gly Glu Leu Leu Gln Lys Ala Gln Gln Ser Asn
                405                 410                 415

Gly Asp Arg Lys His Ser Ser Asp Glu Asn Asn Val Ser Phe Ser His
            420                 425                 430

Leu Cys Leu Val Gly Asn Pro Val Leu Lys Asn Ile Asn Leu Asn Ile
        435                 440                 445

Glu Lys Gly Glu Met Leu Ala Ile Thr Gly Ser Thr Gly Leu Gly Lys
    450                 455                 460

Thr Ser Leu Leu Met Leu Ile Leu Gly Glu Leu Glu Ala Ser Glu Gly
465                 470                 475                 480

Ile Ile Lys His Ser Gly Arg Val Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Lys Ser Val Val Lys Ala Cys Gln Leu Gln Gln
        515                 520                 525

Asp Ile Thr Lys Phe Ala Glu Gln Asp Asn Thr Val Leu Gly Glu Gly
    530                 535                 540

Gly Val Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Phe Thr Glu Glu Gln Val Phe Glu Ser Cys Val Cys
            580                 585                 590

Lys Leu Met Ala Asn Lys Thr Arg Ile Leu Val Thr Ser Lys Met Glu
        595                 600                 605

His Leu Arg Lys Ala Asp Lys Ile Leu Ile Leu His Gln Gly Thr Ser
    610                 615                 620

Tyr Phe Tyr Gly Thr Phe Ser Glu Leu Gln Ser Leu Arg Pro Ser Phe
625                 630                 635                 640

Ser Ser Lys Leu Met Gly Tyr Asp Thr Phe Asp Gln Phe Thr Glu Glu
                645                 650                 655

Arg Arg Ser Ser Ile Leu Thr Glu Thr Leu Arg Arg Phe Ser Val Asp
            660                 665                 670

Asp Ser Ser Ala Pro Trp Ser Lys Pro Lys Gln Ser Phe Arg Gln Thr
        675                 680                 685

Gly Glu Val Gly Glu Lys Arg Lys Asn Ser Ile Leu Asn Ser Phe Ser
    690                 695                 700

Ser Val Arg Lys Ile Ser Ile Val Gln Lys Thr Pro Leu Cys Ile Asp
705                 710                 715                 720

Gly Glu Ser Asp Asp Leu Gln Glu Lys Arg Leu Ser Leu Val Pro Asp
                725                 730                 735

Ser Glu Gln Gly Glu Ala Ala Leu Pro Arg Ser Asn Met Ile Ala Thr
            740                 745                 750

Gly Pro Thr Phe Pro Gly Arg Arg Arg Gln Ser Val Leu Asp Leu Met
        755                 760                 765

Thr Phe Thr Pro Asn Ser Gly Ser Ser Asn Leu Gln Arg Thr Arg Thr
    770                 775                 780

Ser Ile Arg Lys Ile Ser Leu Val Pro Gln Ile Ser Leu Asn Glu Val
785                 790                 795                 800
```

-continued

```
Asp Val Tyr Ser Arg Arg Leu Ser Gln Asp Ser Thr Leu Asn Ile Thr
                805                 810                 815

Glu Glu Ile Asn Glu Glu Asp Leu Lys Glu Cys Phe Leu Asp Asp Val
            820                 825                 830

Ile Lys Ile Pro Pro Val Thr Thr Trp Asn Thr Tyr Leu Arg Tyr Phe
        835                 840                 845

Thr Leu His Lys Gly Leu Leu Leu Val Leu Ile Trp Cys Val Leu Val
    850                 855                 860

Phe Leu Val Glu Val Ala Ala Ser Leu Phe Val Leu Trp Leu Leu Lys
865                 870                 875                 880

Asn Asn Pro Val Asn Ser Gly Asn Asn Gly Thr Lys Ile Ser Asn Ser
                885                 890                 895

Ser Tyr Val Val Ile Ile Thr Ser Thr Ser Phe Tyr Tyr Ile Phe Tyr
            900                 905                 910

Ile Tyr Val Gly Val Ala Asp Thr Leu Leu Ala Leu Ser Leu Phe Arg
        915                 920                 925

Gly Leu Pro Leu Val His Thr Leu Ile Thr Ala Ser Lys Ile Leu His
    930                 935                 940

Arg Lys Met Leu His Ser Ile Leu His Ala Pro Met Ser Thr Ile Ser
945                 950                 955                 960

Lys Leu Lys Ala Gly Gly Ile Leu Asn Arg Phe Ser Lys Asp Ile Ala
                965                 970                 975

Ile Leu Asp Asp Phe Leu Pro Leu Thr Ile Phe Asp Phe Ile Gln Leu
            980                 985                 990

Val Phe Ile Val Ile Gly Ala Ile  Ile Val Val Ser Ala  Leu Gln Pro
        995                 1000                1005

Tyr Ile  Phe Leu Ala Thr Val  Pro Gly Leu Val Val  Phe Ile Leu
    1010                1015                1020

Leu Arg  Ala Tyr Phe Leu His  Thr Ala Gln Gln Leu  Lys Gln Leu
    1025                1030                1035

Glu Ser  Glu Gly Arg Ser Pro  Ile Phe Thr His Leu  Val Thr Ser
    1040                1045                1050

Leu Lys  Gly Leu Trp Thr Leu  Arg Ala Phe Arg Arg  Gln Thr Tyr
    1055                1060                1065

Phe Glu  Thr Leu Phe His Lys  Ala Leu Asn Leu His  Thr Ala Asn
    1070                1075                1080

Trp Phe  Met Tyr Leu Ala Thr  Leu Arg Trp Phe Gln  Met Arg Ile
    1085                1090                1095

Asp Met  Ile Phe Val Leu Phe  Phe Ile Val Val Thr  Phe Ile Ser
    1100                1105                1110

Ile Leu  Thr Thr Gly Glu Gly  Glu Gly Thr Ala Gly  Ile Ile Leu
    1115                1120                1125

Thr Leu  Ala Met Asn Ile Met  Ser Thr Leu Gln Trp  Ala Val Asn
    1130                1135                1140

Ser Ser  Ile Asp Thr Asp Ser  Leu Met Arg Ser Val  Ser Arg Val
    1145                1150                1155

Phe Lys  Phe Ile Asp Ile Gln  Thr Glu Glu Ser Met  Tyr Thr Gln
    1160                1165                1170

Ile Ile  Lys Glu Leu Pro Arg  Glu Gly Ser Ser Asp  Val Leu Val
    1175                1180                1185

Ile Lys  Asn Glu His Val Lys  Lys Ser Asp Ile Trp  Pro Ser Gly
    1190                1195                1200

Gly Glu  Met Val Val Lys Asp  Leu Thr Val Lys Tyr  Met Asp Asp
    1205                1210                1215
```

```
Gly Asn  Ala Val Leu Glu Asn  Ile Ser Phe Ser Ile  Ser Pro Gly
    1220                 1225                 1230

Gln Arg  Val Gly Leu Leu Gly  Arg Thr Gly Ser Gly  Lys Ser Thr
    1235                 1240                 1245

Leu Leu  Ser Ala Phe Leu Arg  Met Leu Asn Ile Lys  Gly Asp Ile
    1250                 1255                 1260

Glu Ile  Asp Gly Val Ser Trp  Asn Ser Val Thr Leu  Gln Glu Trp
    1265                 1270                 1275

Arg Lys  Ala Phe Gly Val Ile  Thr Gln Lys Val Phe  Ile Phe Ser
    1280                 1285                 1290

Gly Thr  Phe Arg Gln Asn Leu  Asp Pro Asn Gly Lys  Trp Lys Asp
    1295                 1300                 1305

Glu Glu  Ile Trp Lys Val Ala  Asp Glu Val Gly Leu  Lys Ser Val
    1310                 1315                 1320

Ile Glu  Gln Phe Pro Gly Gln  Leu Asn Phe Thr Leu  Val Asp Gly
    1325                 1330                 1335

Gly Tyr  Val Leu Ser His Gly  His Lys Gln Leu Met  Cys Leu Ala
    1340                 1345                 1350

Arg Ser  Val Leu Ser Lys Ala  Lys Ile Ile Leu Leu  Asp Glu Pro
    1355                 1360                 1365

Ser Ala  His Leu Asp Pro Ile  Thr Tyr Gln Val Ile  Arg Arg Val
    1370                 1375                 1380

Leu Lys  Gln Ala Phe Ala Gly  Cys Thr Val Ile Leu  Cys Glu His
    1385                 1390                 1395

Arg Ile  Glu Ala Met Leu Asp  Cys Gln Arg Phe Leu  Val Ile Glu
    1400                 1405                 1410

Glu Ser  Asn Val Trp Gln Tyr  Asp Ser Leu Gln Ala  Leu Leu Ser
    1415                 1420                 1425

Glu Lys  Ser Ile Phe Gln Gln  Ala Ile Ser Ser Ser  Glu Lys Met
    1430                 1435                 1440

Arg Phe  Phe Gln Gly Arg His  Ser Ser Lys His Lys  Pro Arg Thr
    1445                 1450                 1455

Gln Ile  Thr Ala Leu Lys Glu  Glu Thr Glu Glu Glu  Val Gln Glu
    1460                 1465                 1470

Thr Arg  Leu
    1475
```

<210> SEQ ID NO 5
<211> LENGTH: 4449
<212> TYPE: DNA
<213> ORGANISM: Sus scrofa

<400> SEQUENCE: 5

```
atgcagaggt cgcctctgga aaaggccagc atcttctcca aacttttttt cagctggacc      60

agaccaattt tgagaaaagg atatagacag cgcctggaat tgtcagacat ataccatatc     120

tcttcttctg actctgctga caatctgtct gaaaaattgg aaagagaatg ggacagagaa     180

ctggcttcaa agaagaatcc caaactcatt aatgcccttc ggcgatgttt tttttggaga     240

tttatgttct atggaatcat attatattta ggggaagtca ccaaagcagt ccagcctctc     300

ttactgggaa gaatcatagc ttcctatgat ccagataaca aggcggaacg ctccattgcg     360

atttacctag gcgtaggctt atgtcttctc ttcatcgtga ggactctgct cctgcaccca     420

gccatttttg gcccccatca cattggcatg cagatgagaa tagctatgtt tagtttgatt     480

tacaaaaaga ctttgaagct gtcaagccgt gttctagata aaataagtat tggacaactt     540
```

-continued

```
gttagtctcc tttccaacaa cctgaacaag tttgatgaag gacttgcctt ggcgcacttc    600
gtgtggatcg ctcctctgca agtgacgctg ctgatggggc tgctgtggga gttgttgcag    660
gcctccgcct tctgtggact tgccttcctc gtagtcctcg ccctctttca agctgggttg    720
gggaaaatga tgatgaagta cagagatcag agagctggaa agatcaatga aagactggtg    780
attacctcag agatgattga aaatatccaa tcagttaaag catactgctg ggaagaagcg    840
atggaaaaaa tgattgaaaa cctaagacaa acggaactga aactgacccg gaaggcagcc    900
tatgtgagat acttcaatag ctcagccttc ttcttctctg ggctctttgt ggtgttttta    960
tctgtgcttc cctacgcact gctcaaagga atcatgcttc gaaaaatctt cacaaccatc   1020
tcattctgca ttgttctgcg catggcagtc acccggcaat tcccctgggc tgtacaaact   1080
tggtatgatt ctcttggagc aataaacaaa atacaggatt tcttacagaa gcaagaatat   1140
aagacactgg aatacaactt aacaactaca gaagtagtga tggagaatgt aacagccttc   1200
tgggaagagg gatttgggaa attatttgag aaagcaaaac aaaataataa cagtcgaaaa   1260
atttccaatg gtgataacag cctcttcttc agtaactttt cacttctcgg tactcctgtc   1320
ctgaaagata tcagtttcaa gatagaaaga ggacaattgt tggcagttgc tggatctact   1380
ggagcaggca agacatcact tctgatgatg attatgggag aactggagcc ttcagagggt   1440
aaaattaagc acagtggaag aatttcattc tgctctcagt tttcctggat catgccgggc   1500
accattaaag aaaacatcat ctttggtgtt tcctatgatg agtatagata caggagtgtc   1560
atcaaagcgt gccaactaga agaggacatc tccaagtttg cagagaaaga caacatagtt   1620
ctgggagaag gtggaatcac actgagtgga ggtcagcgag caagaatttc tttagcaaga   1680
gcagtatata aagatgctga tttgtaccta ttagactctc cttttggata cctagatgtt   1740
ttaacagaga aagaaatatt tgaaagctgt gtctgtaaat tgatggctaa caaaactagg   1800
attttggtca cttctaaaat ggaacattta aagaaagctg acaaaatact aattttacat   1860
gaaggtagca gctattttta tgggacattt tctgaattac aaagtcagcg gcccgacttc   1920
agttcaaagc ttatgggata tgatactttt gaccaattta ctgcagaacg gagaaattca   1980
atcataactg agactttacg gcgtttctca ttagaaggag atgcctctgt gtcctggaac   2040
gaaacaaaaa aacaatcctt taaacagact ggagagtttg gtgaaaaaag gaagaattcc   2100
attctcaatt caatcaactc tataaggaaa ttttcaattg tacaaaagac tcccttacaa   2160
atgaatggct ttgaagaaga ttctggcgag cctttagaga gaaggctgtc cttagttcct   2220
gattctgagc atggggaggc aattctacct cggagcaacg tgatcaacgc tggccccacg   2280
tttcagggac gacggaggca gtctgttctg aacctcatga cccgctcctc agtgaaccaa   2340
ggtcaaagca ttcaccgaaa gacagcgacg tccacacgga aaatgtcact ggtccctcaa   2400
gcaaacttaa ctgaaataga tatatattcc agacgattat cgcaagatac tggcttggaa   2460
ataagtgaag aaattaatga agaagattta agggagtgct tttttgatga cgtggagagc   2520
ataccaaccg tgactacctg gaacacatac ctccgatatg ttactgttca caagagctta   2580
atttttgtgc tgatttggtg cttagttgtt tttctggctg aggtggctgc ttgtttggtt   2640
gtgttgtgtt tgcttaaaaa aacatctcct caagacaaag ggaatagcac taagggtgca   2700
aataacagct atgcagtaat catcaccagc accagcgcat actatgtttt ttacatttac   2760
gtgggagtag ccgacggttt gcttgctctg ggactcttca gaggtttacc actggtgcat   2820
actctaatca cagtgtcgaa aattttacat cgcaaaatgt tacactctgt tcttcaagcc   2880
cctatgtcaa ccctcaacac attgaaagca ggtgggattc ttaatagatt ctccaaagat   2940
```

atagcagttt tggatgatct cctgcctctt actatatttg atttcatcca gttactatta 3000
attgtgattg gagctgtggc agttgtctca gttttaaaac cttacatctt cctggcaaca 3060
gtgccagtga tagtggcttt tattctactg agagcctact tcctccacac ttcacagcag 3120
ctcaaacagc tggaatctga aggcaggagt ccaattttca ctcatctcat tacaagctta 3180
aaaggactat ggacccttcg agcctttgga cgtcagcctt actttgaaac tttgttccac 3240
aaagctctta atttacatac tgccaactgg ttcttgtatc tgtcaacact acgctggttc 3300
caaatgcgaa tagaaatgat ttttgtcatc tttttcattg ccgttacctt catttccatt 3360
ttaacaacag gggaaggaga aggaacagtt gggattattc taacattagc catgaatatc 3420
atgagtacat tgcagtgggc tgtaaactcc agtatagatg tggatagctt gatgcgatct 3480
gtgagccgag tctttaagtt tattgatatg ccggcagaag gagatcaacc taacaggtcg 3540
ttcaaaccat ccaaggatgg ccagctttca aaggttatga ttattgagaa tcaacatgtg 3600
aagaaagatg acatctggcc ttcagggggc caaatgactg tcaaagacct cactgcgaaa 3660
tatgtagatg gtgggaacgc cgtattagag aacatttcct tctcaataag tcctggccag 3720
agggtgggcc tcttgggaag aactggatca gggaagagca ctttattatt ggctttttttg 3780 agactgctga acacagaagg agaaatacaa gtagatggtg tgtcttggga ttcaataact 3840
ttgcaacagt ggaggaaagc ttttggagtc ataccccaga aagtattcat cttttctgga 3900
acatttagaa aaaacctgga tccctatgga cagtggaatg atcaagaaat atggaaagtt 3960
gcagaggagg ttggactcag atctgtgata gagcagtttc ctgggaagct tgattttgtc 4020
cttgtagatg gggttgtgt tctaagccac ggccacaagc agttgatgtg cttggccaga 4080
tctgttcttg gtaaagcaaa gatcttgctg ctggatgaac ccagtgctca tttggatccc 4140
ataacgtacc aaatcattcg aagaaccctg aaacaagcat ttgctgattg cacagtaatc 4200
ctctctgaac acaggataga agcaatgttg gaatgtcaac gatttttggt catagaggag 4260
aacaaagtgc ggcagtatga ttccatccag aggctgctga gcgagaagag cctcttcagg 4320
caggcgatca gccccttgga ccgcctgaag ctcctcccac accggaactc tagcaagcag 4380
aggtctcggt ccaaaatcgc agctctgaag gaggaaacag aagaagaggt gcaagaaaca 4440
agactttag 4449

<210> SEQ ID NO 6
<211> LENGTH: 1482
<212> TYPE: PRT
<213> ORGANISM: Sus scrofa

<400> SEQUENCE: 6

```
Met Gln Arg Ser Pro Leu Glu Lys Ala Ser Ile Phe Ser Lys Leu Phe
1               5                   10                  15

Phe Ser Trp Thr Arg Pro Ile Leu Arg Lys Gly Tyr Arg Gln Arg Leu
            20                  25                  30

Glu Leu Ser Asp Ile Tyr His Ile Ser Ser Ser Asp Ser Ala Asp Asn
        35                  40                  45

Leu Ser Glu Lys Leu Glu Arg Glu Trp Asp Arg Glu Leu Ala Ser Lys
    50                  55                  60

Lys Asn Pro Lys Leu Ile Asn Ala Leu Arg Arg Cys Phe Phe Trp Arg
65                  70                  75                  80

Phe Met Phe Tyr Gly Ile Ile Leu Tyr Leu Gly Glu Val Thr Lys Ala
                85                  90                  95

Val Gln Pro Leu Leu Leu Gly Arg Ile Ile Ala Ser Tyr Asp Pro Asp
            100                 105                 110
```

-continued

```
Asn Lys Ala Glu Arg Ser Ile Ala Ile Tyr Leu Gly Val Gly Leu Cys
        115                 120                 125

Leu Leu Phe Ile Val Arg Thr Leu Leu Leu His Pro Ala Ile Phe Gly
    130                 135                 140

Pro His His Ile Gly Met Gln Met Arg Ile Ala Met Phe Ser Leu Ile
145                 150                 155                 160

Tyr Lys Lys Thr Leu Lys Leu Ser Ser Arg Val Leu Asp Lys Ile Ser
                165                 170                 175

Ile Gly Gln Leu Val Ser Leu Leu Ser Asn Asn Leu Asn Lys Phe Asp
            180                 185                 190

Glu Gly Leu Ala Leu Ala His Phe Val Trp Ile Ala Pro Leu Gln Val
        195                 200                 205

Thr Leu Leu Met Gly Leu Leu Trp Glu Leu Leu Gln Ala Ser Ala Phe
    210                 215                 220

Cys Gly Leu Ala Phe Leu Val Val Leu Ala Leu Phe Gln Ala Gly Leu
225                 230                 235                 240

Gly Lys Met Met Met Lys Tyr Arg Asp Gln Arg Ala Gly Lys Ile Asn
                245                 250                 255

Glu Arg Leu Val Ile Thr Ser Glu Met Ile Glu Asn Ile Gln Ser Val
            260                 265                 270

Lys Ala Tyr Cys Trp Glu Glu Ala Met Glu Lys Met Ile Glu Asn Leu
        275                 280                 285

Arg Gln Thr Glu Leu Lys Leu Thr Arg Lys Ala Ala Tyr Val Arg Tyr
    290                 295                 300

Phe Asn Ser Ser Ala Phe Phe Phe Ser Gly Leu Phe Val Val Phe Leu
305                 310                 315                 320

Ser Val Leu Pro Tyr Ala Leu Leu Lys Gly Ile Met Leu Arg Lys Ile
                325                 330                 335

Phe Thr Thr Ile Ser Phe Cys Ile Val Leu Arg Met Ala Val Thr Arg
            340                 345                 350

Gln Phe Pro Trp Ala Val Gln Thr Trp Tyr Asp Ser Leu Gly Ala Ile
        355                 360                 365

Asn Lys Ile Gln Asp Phe Leu Gln Lys Gln Glu Tyr Lys Thr Leu Glu
    370                 375                 380

Tyr Asn Leu Thr Thr Thr Glu Val Val Met Glu Asn Val Thr Ala Phe
385                 390                 395                 400

Trp Glu Glu Gly Phe Gly Lys Leu Phe Glu Lys Ala Lys Gln Asn Asn
                405                 410                 415

Asn Ser Arg Lys Ile Ser Asn Gly Asp Asn Ser Leu Phe Phe Ser Asn
            420                 425                 430

Phe Ser Leu Leu Gly Thr Pro Val Leu Lys Asp Ile Ser Phe Lys Ile
        435                 440                 445

Glu Arg Gly Gln Leu Leu Ala Val Ala Gly Ser Thr Gly Ala Gly Lys
    450                 455                 460

Thr Ser Leu Leu Met Met Ile Met Gly Glu Leu Glu Pro Ser Glu Gly
465                 470                 475                 480

Lys Ile Lys His Ser Gly Arg Ile Ser Phe Cys Ser Gln Phe Ser Trp
                485                 490                 495

Ile Met Pro Gly Thr Ile Lys Glu Asn Ile Ile Phe Gly Val Ser Tyr
            500                 505                 510

Asp Glu Tyr Arg Tyr Arg Ser Val Ile Lys Ala Cys Gln Leu Glu Glu
        515                 520                 525

Asp Ile Ser Lys Phe Ala Glu Lys Asp Asn Ile Val Leu Gly Glu Gly
    530                 535                 540
```

-continued

```
Gly Ile Thr Leu Ser Gly Gly Gln Arg Ala Arg Ile Ser Leu Ala Arg
545                 550                 555                 560

Ala Val Tyr Lys Asp Ala Asp Leu Tyr Leu Leu Asp Ser Pro Phe Gly
                565                 570                 575

Tyr Leu Asp Val Leu Thr Glu Lys Glu Ile Phe Glu Ser Cys Val Cys
            580                 585                 590

Lys Leu Met Ala Asn Lys Thr Arg Ile Leu Val Thr Ser Lys Met Glu
        595                 600                 605

His Leu Lys Lys Ala Asp Lys Ile Leu Ile Leu His Glu Gly Ser Ser
    610                 615                 620

Tyr Phe Tyr Gly Thr Phe Ser Glu Leu Gln Ser Gln Arg Pro Asp Phe
625                 630                 635                 640

Ser Ser Lys Leu Met Gly Tyr Asp Thr Phe Asp Gln Phe Thr Ala Glu
                645                 650                 655

Arg Arg Asn Ser Ile Ile Thr Glu Thr Leu Arg Arg Phe Ser Leu Glu
            660                 665                 670

Gly Asp Ala Ser Val Ser Trp Asn Glu Thr Lys Lys Gln Ser Phe Lys
        675                 680                 685

Gln Thr Gly Glu Phe Gly Glu Lys Arg Lys Asn Ser Ile Leu Asn Ser
    690                 695                 700

Ile Asn Ser Ile Arg Lys Phe Ser Ile Val Gln Lys Thr Pro Leu Gln
705                 710                 715                 720

Met Asn Gly Phe Glu Glu Asp Ser Gly Glu Pro Leu Glu Arg Arg Leu
                725                 730                 735

Ser Leu Val Pro Asp Ser Glu His Gly Glu Ala Ile Leu Pro Arg Ser
            740                 745                 750

Asn Val Ile Asn Ala Gly Pro Thr Phe Gln Gly Arg Arg Arg Gln Ser
        755                 760                 765

Val Leu Asn Leu Met Thr Arg Ser Ser Val Asn Gln Gly Gln Ser Ile
    770                 775                 780

His Arg Lys Thr Ala Thr Ser Thr Arg Lys Met Ser Leu Val Pro Gln
785                 790                 795                 800

Ala Asn Leu Thr Glu Ile Asp Ile Tyr Ser Arg Arg Leu Ser Gln Asp
                805                 810                 815

Thr Gly Leu Glu Ile Ser Glu Glu Ile Asn Glu Glu Asp Leu Arg Glu
            820                 825                 830

Cys Phe Phe Asp Asp Val Glu Ser Ile Pro Thr Val Thr Thr Trp Asn
        835                 840                 845

Thr Tyr Leu Arg Tyr Val Thr Val His Lys Ser Leu Ile Phe Val Leu
    850                 855                 860

Ile Trp Cys Leu Val Val Phe Leu Ala Glu Val Ala Ala Cys Leu Val
865                 870                 875                 880

Val Leu Cys Leu Leu Lys Lys Thr Ser Pro Gln Asp Lys Gly Asn Ser
                885                 890                 895

Thr Lys Gly Ala Asn Asn Ser Tyr Ala Val Ile Ile Thr Ser Thr Ser
            900                 905                 910

Ala Tyr Tyr Val Phe Tyr Ile Tyr Val Gly Val Ala Asp Gly Leu Leu
        915                 920                 925

Ala Leu Gly Leu Phe Arg Gly Leu Pro Leu Val His Thr Leu Ile Thr
    930                 935                 940

Val Ser Lys Ile Leu His Arg Lys Met Leu His Ser Val Leu Gln Ala
945                 950                 955                 960

Pro Met Ser Thr Leu Asn Thr Leu Lys Ala Gly Gly Ile Leu Asn Arg
                965                 970                 975
```

-continued

```
Phe Ser Lys Asp Ile Ala Val Leu Asp Asp Leu Leu Pro Leu Thr Ile
            980                 985                 990

Phe Asp Phe Ile Gln Leu Leu Leu  Ile Val Ile Gly Ala  Val Ala Val
        995                 1000                1005

Val Ser  Val Leu Lys Pro Tyr  Ile Phe Leu Ala Thr  Val Pro Val
    1010                 1015                 1020

Ile Val  Ala Phe Ile Leu Leu  Arg Ala Tyr Phe Leu  His Thr Ser
    1025                 1030                 1035

Gln Gln  Leu Lys Gln Leu Glu  Ser Glu Gly Arg Ser  Pro Ile Phe
    1040                 1045                 1050

Thr His  Leu Ile Thr Ser Leu  Lys Gly Leu Trp Thr  Leu Arg Ala
    1055                 1060                 1065

Phe Gly  Arg Gln Pro Tyr Phe  Glu Thr Leu Phe His  Lys Ala Leu
    1070                 1075                 1080

Asn Leu  His Thr Ala Asn Trp  Phe Leu Tyr Leu Ser  Thr Leu Arg
    1085                 1090                 1095

Trp Phe  Gln Met Arg Ile Glu  Met Ile Phe Val Ile  Phe Phe Ile
    1100                 1105                 1110

Ala Val  Thr Phe Ile Ser Ile  Leu Thr Thr Gly Glu  Gly Glu Gly
    1115                 1120                 1125

Thr Val  Gly Ile Ile Leu Thr  Leu Ala Met Asn Ile  Met Ser Thr
    1130                 1135                 1140

Leu Gln  Trp Ala Val Asn Ser  Ser Ile Asp Val Asp  Ser Leu Met
    1145                 1150                 1155

Arg Ser  Val Ser Arg Val Phe  Lys Phe Ile Asp Met  Pro Ala Glu
    1160                 1165                 1170

Gly Asp  Gln Pro Asn Arg Ser  Phe Lys Pro Ser Lys  Asp Gly Gln
    1175                 1180                 1185

Leu Ser  Lys Val Met Ile Ile  Glu Asn Gln His Val  Lys Lys Asp
    1190                 1195                 1200

Asp Ile  Trp Pro Ser Gly Gly  Gln Met Thr Val Lys  Asp Leu Thr
    1205                 1210                 1215

Ala Lys  Tyr Val Asp Gly Gly  Asn Ala Val Leu Glu  Asn Ile Ser
    1220                 1225                 1230

Phe Ser  Ile Ser Pro Gly Gln  Arg Val Gly Leu Leu  Gly Arg Thr
    1235                 1240                 1245

Gly Ser  Gly Lys Ser Thr Leu  Leu Leu Ala Phe Leu  Arg Leu Leu
    1250                 1255                 1260

Asn Thr  Glu Gly Glu Ile Gln  Val Asp Gly Val Ser  Trp Asp Ser
    1265                 1270                 1275

Ile Thr  Leu Gln Gln Trp Arg  Lys Ala Phe Gly Val  Ile Pro Gln
    1280                 1285                 1290

Lys Val  Phe Ile Phe Ser Gly  Thr Phe Arg Lys Asn  Leu Asp Pro
    1295                 1300                 1305

Tyr Gly  Gln Trp Asn Asp Gln  Glu Ile Trp Lys Val  Ala Glu Glu
    1310                 1315                 1320

Val Gly  Leu Arg Ser Val Ile  Glu Gln Phe Pro Gly  Lys Leu Asp
    1325                 1330                 1335

Phe Val  Leu Val Asp Gly Gly  Cys Val Leu Ser His  Gly His Lys
    1340                 1345                 1350

Gln Leu  Met Cys Leu Ala Arg  Ser Val Leu Gly Lys  Ala Lys Ile
    1355                 1360                 1365

Leu Leu  Leu Asp Glu Pro Ser  Ala His Leu Asp Pro  Ile Thr Tyr
    1370                 1375                 1380
```

```
Gln Ile  Ile Arg Arg Thr Leu  Lys Gln Ala Phe Ala  Asp Cys Thr
    1385                 1390                 1395

Val Ile  Leu Ser Glu His Arg  Ile Glu Ala Met Leu  Glu Cys Gln
    1400                 1405                 1410

Arg Phe  Leu Val Ile Glu Glu  Asn Lys Val Arg Gln  Tyr Asp Ser
    1415                 1420                 1425

Ile Gln  Arg Leu Leu Ser Glu  Lys Ser Leu Phe Arg  Gln Ala Ile
    1430                 1435                 1440

Ser Pro  Leu Asp Arg Leu Lys  Leu Leu Pro His Arg  Asn Ser Ser
    1445                 1450                 1455

Lys Gln  Arg Ser Arg Ser Lys  Ile Ala Ala Leu Lys  Glu Glu Thr
    1460                 1465                 1470

Glu Glu  Glu Val Gln Glu Thr  Arg Leu
    1475                 1480


<210> SEQ ID NO 7
<211> LENGTH: 21
<212> TYPE: DNA
<213> ORGANISM: Artificial Sequence
<220> FEATURE:
<223> OTHER INFORMATION: Primer

<400> SEQUENCE: 7

tttctcttct gcctatttcc c                                          21


<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8

agaaaacact gaaggatgcc t                                          21


<210> SEQ ID NO 9
<211> LENGTH: 24
<212> TYPE: DNA
<213> ORGANISM: Artificial Sequence
<220> FEATURE:
<223> OTHER INFORMATION: Primer

<400> SEQUENCE: 9

gtttcaaata gttactcagt ttga                                       24


<210> SEQ ID NO 10
<211> LENGTH: 25
<212> TYPE: DNA
<213> ORGANISM: Artificial Sequence
<220> FEATURE:
<223> OTHER INFORMATION: Primer

<400> SEQUENCE: 10

cctccaactg acactaatct tctca                                      25


<210> SEQ ID NO 11
<211> LENGTH: 21
<212> TYPE: DNA
<213> ORGANISM: Artificial Sequence
<220> FEATURE:
<223> OTHER INFORMATION: Primer

<400> SEQUENCE: 11

gtagagctgt cagagaagta a                                          21
```

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
aagccacaga agcatatgca t 21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
aatcactctc aggatgcaca t 21

<210> SEQ ID NO 14
<211> LENGTH: 21
<212> TYPE: DNA
<213> ORGANISM: Artificial Sequence
<220> FEATURE:
<223> OTHER INFORMATION: Primer

<400> SEQUENCE: 14
atactcagaa caggaagtgc t 21

<210> SEQ ID NO 15
<211> LENGTH: 21
<212> TYPE: DNA
<213> ORGANISM: Artificial Sequence
<220> FEATURE:
<223> OTHER INFORMATION: Primer

<400> SEQUENCE: 15
atagcataag cttcactgtg c 21

<210> SEQ ID NO 16
<211> LENGTH: 23
<212> TYPE: DNA
<213> ORGANISM: Artificial Sequence
<220> FEATURE:
<223> OTHER INFORMATION: Primer

<400> SEQUENCE: 16
tgtcagtaga gaattagaga tta 23

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
gcactactca cctacatcca 20

<210> SEQ ID NO 18
<211> LENGTH: 21
<212> TYPE: DNA
<213> ORGANISM: Artificial Sequence
<220> FEATURE:
<223> OTHER INFORMATION: Primer

<400> SEQUENCE: 18
acctggaagt tggaacactc a 21

<210> SEQ ID NO 19
<211> LENGTH: 22
<212> TYPE: DNA
<213> ORGANISM: Artificial Sequence
<220> FEATURE:
<223> OTHER INFORMATION: Primer

<400> SEQUENCE: 19
gaagaccctt taccttcttc ta 22

<210> SEQ ID NO 20
<211> LENGTH: 21
<212> TYPE: DNA
<213> ORGANISM: Artificial Sequence
<220> FEATURE:
<223> OTHER INFORMATION: Primer

<400> SEQUENCE: 20
catccagctg caaacaacat t 21

<210> SEQ ID NO 21
<211> LENGTH: 23
<212> TYPE: DNA
<213> ORGANISM: Artificial Sequence
<220> FEATURE:
<223> OTHER INFORMATION: Primer

<400> SEQUENCE: 21
aattatgcca aactccatct tat 23

<210> SEQ ID NO 22
<211> LENGTH: 22
<212> TYPE: DNA
<213> ORGANISM: Artificial Sequence
<220> FEATURE:
<223> OTHER INFORMATION: Primer

<400> SEQUENCE: 22
agaatttcat tctgctctca gt 22

<210> SEQ ID NO 23
<211> LENGTH: 25
<212> TYPE: DNA
<213> ORGANISM: Artificial Sequence
<220> FEATURE:
<223> OTHER INFORMATION: Primer

<400> SEQUENCE: 23
agtgggctgt aaactccagt ataga 25

<210> SEQ ID NO 24
<211> LENGTH: 25
<212> TYPE: DNA
<213> ORGANISM: Artificial Sequence
<220> FEATURE:
<223> OTHER INFORMATION: Primer

<400> SEQUENCE: 24
ccttctgccg gcatatcaat aaact 25

<210> SEQ ID NO 25
<211> LENGTH: 17
<212> TYPE: DNA
<213> ORGANISM: Artificial Sequence
<220> FEATURE:
<223> OTHER INFORMATION: Primer

<400> SEQUENCE: 25
atcgcatcaa gctatcc 17

<210> SEQ ID NO 26
<211> LENGTH: 24
<212> TYPE: DNA
<213> ORGANISM: Artificial Sequence
<220> FEATURE:
<223> OTHER INFORMATION: Primer

<400> SEQUENCE: 26
aagctcattt cctcgtacga caat 24

<210> SEQ ID NO 27
<211> LENGTH: 18
<212> TYPE: DNA
<213> ORGANISM: Artificial Sequence
<220> FEATURE:
<223> OTHER INFORMATION: Primer

<400> SEQUENCE: 27
ggaggccatg tggaccat 18

<210> SEQ ID NO 28
<211> LENGTH: 17
<212> TYPE: DNA
<213> ORGANISM: Artificial Sequence
<220> FEATURE:
<223> OTHER INFORMATION: Primer

<400> SEQUENCE: 28
tccaccaccc tgttgct 17

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
tcatgccggg caccattaaa 20

<210> SEQ ID NO 30
<211> LENGTH: 25
<212> TYPE: DNA
<213> ORGANISM: Artificial Sequence
<220> FEATURE:
<223> OTHER INFORMATION: Primer

<400> SEQUENCE: 30
cgctttgatg acactcctgt atcta 25

<210> SEQ ID NO 31
<211> LENGTH: 20
<212> TYPE: DNA
<213> ORGANISM: Artificial Sequence
<220> FEATURE:
<223> OTHER INFORMATION: Primer -continued

<400> SEQUENCE: 31
acaccaaaga tgatgttttc 20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
tcatgccggg caccattaaa 20

<210> SEQ ID NO 33
<211> LENGTH: 25
<212> TYPE: DNA
<213> ORGANISM: Artificial Sequence
<220> FEATURE:
<223> OTHER INFORMATION: Primer

<400> SEQUENCE: 33
cgctttgatg acactcctgt atcta 25

<210> SEQ ID NO 34
<211> LENGTH: 20
<212> TYPE: DNA
<213> ORGANISM: Artificial Sequence
<220> FEATURE:
<223> OTHER INFORMATION: Primer

<400> SEQUENCE: 34
gaaacaccaa tgatgttttc 20